United States Patent
Li et al.

(10) Patent No.: US 11,352,630 B2
(45) Date of Patent: Jun. 7, 2022

(54) SBE APTAMERS FOR TREATING IL-17A RELATED DISEASES AND CONDITIONS

(71) Applicant: The Cleveland Clinic Foundation, Cleveland, OH (US)

(72) Inventors: Xiaoxia Li, Cleveland, OH (US); Tomasz Herjan, Beachwood, OH (US); Lingzi Hong, Cleveland Heights, OH (US); Donna Marie Driscoll, Cleveland, OH (US); Caini Liu, Solon, OH (US)

( * ) Notice: Subject to any disclaimer, the term of this patent is extended or adjusted under 35 U.S.C. 154(b) by 31 days.

(21) Appl. No.: 16/632,757

(22) PCT Filed: Jul. 19, 2018

(86) PCT No.: PCT/US2018/042899
§ 371 (c)(1),
(2) Date: Jan. 21, 2020

(87) PCT Pub. No.: WO2019/018652
PCT Pub. Date: Jan. 24, 2019

(65) Prior Publication Data
US 2020/0157544 A1    May 21, 2020

Related U.S. Application Data

(60) Provisional application No. 62/535,559, filed on Jul. 21, 2017.

(51) Int. Cl.
| | | |
|---|---|---|
| C12N 15/115 | (2010.01) | |
| A61P 37/06 | (2006.01) | |
| A61K 31/713 | (2006.01) | |

(52) U.S. Cl.
CPC .......... *C12N 15/115* (2013.01); *A61K 31/713* (2013.01); *A61P 37/06* (2018.01)

(58) Field of Classification Search
None
See application file for complete search history.

(56) References Cited

U.S. PATENT DOCUMENTS

| 2015/0158912 A1* | 6/2015 | Li | A61P 29/00 |
| | | | 514/1.7 |
| 2015/0337309 A1* | 11/2015 | Suh | C12N 15/115 |
| | | | 514/44 R |
| 2018/0258431 A1* | 9/2018 | Yang | C12N 15/115 |

FOREIGN PATENT DOCUMENTS

| WO | WO 2012/075326 A2 | 6/2012 |
| WO | WO 2013/063557 A1 | 5/2013 |

OTHER PUBLICATIONS

Aizer, et al., The P body protein Dcp1a is hyper-phosphorylated during mitosis. PloS One. 2013;8(1):e49783.
Anderson, et al., Stress granules, P-bodies and cancer. Biochim Biophys Acta. Jul. 2015;1849(7):861-70.
Arribas-Layton, et al., Structural and functional control of the eukaryotic mRNA decapping machinery. Biochim Biophys Acta. Jun.-Jul. 2013;1829(6-7):580-9.
Brannan, et al. mRNA decapping factors and the exonuclease Xrn2 function in widespread premature termination of RNA polymerase II transcription. Mol Cell. May 11, 2012;46(3):311-24.
Brennan, et al., HuR and mRNA stability.Cell Mol Life Sci. Feb. 2001;58(2):266-77.
Bresson, et al., Nuclear RNA Decay Pathways Aid Rapid Remodeling of Gene Expression in Yeast. Mol Cell. Mar. 2, 2017;65(5):787-800.e5.
Bulek, et al. The inducible kinase IKKi is required for IL-17-dependent signaling associated with neutrophilia and pulmonary inflammation. Nat Immunol. Aug. 7, 2011;12(9):844-52.
Cao, et al., Both phosphorylation and dephosphorylation of ASF/SF2 are required for pre-mRNA splicing in vitro. RNA. Dec. 1997;3(12):1456-67.
Chang, et al., Act1 adaptor protein is an immediate and essential signaling component of interleukin-17 receptorJ Biol Chem. Nov. 24, 2006;281(47):35603-7.
Chen, et al., Mechanisms of deadenylation-dependent decay. Wiley Interdiscip Rev RNA. Mar.-Apr. 2011;2(2):167-83.
Chesné, et al., Prime role of IL-17A in neutrophilia and airway smooth muscle contraction in a house dust mite-induced allergic asthma model. J Allergy Clin Immunol. Jun. 2015;135(6):1643-1643.e3.
Cho, et al. IL-17 is essential for host defense against cutaneous *Staphylococcus aureus* infection in mice.J Clin Invest. May 2010;120(5):1762-73.
Conti, et al. Th17 cells and IL-17 receptor signaling are essential for mucosal host defense against oral candidiasis. J Exp Med. Feb. 16, 2009;206(2):299-311.
Cua, et al., Innate IL-17-producing cells: the sentinels of the immune system. Nat Rev Immunol. Jul. 2010;10(7):479-89.
Datta, et al., Tristetraprolin regulates CXCL1 (KC) mRNA stability. J Immunol. Feb. 15, 2008;180(4):2545-52.
Datta, et al., IL-17 regulates CXCL1 mRNA stability via an AUUUA/tristetraprolin-independent sequence. J Immunol. Feb. 1, 2010;184(3):1484-91.
Deng, et al., An improved protocol for rapid freezing of protein samples for long-term storage. Acta Crystallogr D Biol Crystallogr. Jan. 2004;60(Pt 1):203-4.
Deng, et al., Structure of the ROC domain from the Parkinson's disease-associated leucine-rich repeat kinase 2 reveals a dimeric GTPase. Proc Natl Acad Sci U S A. Feb. 5, 2008;105(5):1499-504.
Erickson, et al., Cytoplasmic mRNP granules at a glance. J Cell Sci. Feb. 1, 2011;124(Pt 3):293-7.
Extended European Search Report. dated Mar. 25, 2021. 10 Pages.
Franks, et al., The control of mRNA decapping and P-body formation. Mol Cell. Dec. 5, 2008;32(5):605-15.

(Continued)

*Primary Examiner* — Tracy Vivlemore
(74) *Attorney, Agent, or Firm* — Casimir Jones, S.C.; Jason R. Bond

(57) ABSTRACT

Provided herein are compositions, systems, kits, and methods for treating IL-17a related diseases and conditions using an SBE nucleic acid sequence that binds a SEFIR domain of an ACT1 protein.

20 Claims, 22 Drawing Sheets

Specification includes a Sequence Listing.

(56) References Cited

OTHER PUBLICATIONS

GenBank Accession No. BC037997, Mus musculus chemokine (C—X—C motif) ligand 1, mRNA (cDNA cloe image:5321155_partial cds, Strausberg et al., Oct. 29, 2004, online retrieved on Nov. 27, 2018, 2 pages.
Gu, et al., IL-17 family: cytokines, receptors and signaling. Cytokine. Nov. 2013;64(2):477-85.
Gudipati, et al., Extensive degradation of RNA precursors by the exosome in wild-type cells. Mol Cell. Nov. 9, 2012;48(3):409-21.
Harrington, et al., Interleukin 17-producing CD4+ effector T cells develop via a lineage distinct from the T helper type 1 and 2 lineages. Nat Immunol. Nov. 2005;6(11):1123-32.
Hartupee, et al., IL-17 enhances chemokine gene expression through mRNA stabilization. J Immunol. Sep. 15, 2007;179(6):4135-41.
Herjan et al., IL-17-receptor-associated adaptor Act1 directly stabilizes mRNAs to mediate IL-17 inflammatory signaling. Nat Immunol. Apr. 2018;19(4):354-365.
Herjan, et al. HuR is required for IL-17-induced Act1-mediated CXCL1 and CXCL5 mRNA stabilization. J Immunol. Jul. 15, 2013;191(2):640-9.
Hu, et al, Co-translational mRNA decay in *Saccharomyces cerevisiae*. Nature. Sep. 10, 2009;461(7261):225-9.
Huynh, et al., Allosteric Interactions Direct Binding and Phosphorylation of ASF/SF2 by SRPK1. Biochemistry. Dec. 8, 2009;48(48):11432-40.
International Search Report and Written Opinion, PCT/US 18/42899, dated Dec. 10, 2018, 12 pgs.
Jackson, et al., The balance sheet for transcription: an analysis of nuclear RNA metabolism in mammalian cells. FASEB J. Feb. 2000;14(2):242-54.
Kang, et al. Astrocyte-restricted ablation of interleukin-17-induced Act1-mediated signaling ameliorates autoimmune encephalomyelitis. Immunity. Mar. 26, 2010;32(3):414-25.
Kolls, et al. The role of Th17 cytokines in primary mucosal immunity. Cytokine Growth Factor Rev. Dec. 2010;21(6):443-8.
Krainer, et al., The essential pre-mRNA splicing factor SF2 influences 5' splice site selection by activating proximal sites. Cell. Jul. 13, 1990;62(1):35-42.
Lemaire, et al., Stability of a PKCI-1-related mRNA is controlled by the splicing factor ASF/SF2: a novel function for SR proteins. Genes Dev. Mar. 1, 2002;16(5):594-607.
Leppek, et al., Roquin promotes constitutive mRNA decay via a conserved class of stem-loop recognition motifs. Cell. May 9, 2013;153(4):869-81.
Li, et al., Act1, an NF-kappa B-activating protein. Proc Natl Acad Sci U S A. Sep. 12, 2000;97(19):10489-93.
Liu, et al. A CC' loop decoy peptide blocks the interaction between Act1 and IL-17RA to attenuate IL-17- and IL-25-induced inflammation. Sci Signal. Nov. 1, 2011;4(197):ra72.
Liu, et al. The flavonoid cyanidin blocks binding of the cytokine interleukin-17A to the IL-17RA subunit to alleviate inflammation in vivo. Sci Signal. Feb. 21, 2017;10(467):eaaf8823.
Milner, et al., The cup runneth over: lessons from the ever-expanding pool of primary immunodeficiency diseases. Nat Rev Immunol. Sep. 2013;13(9):635-48.
Mino, et al. Regnase-1 and Roquin Regulate a Common Element in Inflammatory mRNAs by Spatiotemporally Distinct Mechanisms. Cell. May 21, 2015;161(5):1058-1073.
Mitchell, et al., Principles and properties of eukaryotic mRNPs. Mol Cell. May 22, 2014;54(4):547-58.
Mukherjee, et al., Integrative regulatory mapping indicates that the RNA-binding protein HuR couples pre-mRNA processing and mRNA stability. Mol Cell. Aug. 5, 2011;43(3):327-39.
Mukherjee, et al., Identification of cytoplasmic capping targets reveals a role for cap homeostasis in translation and mRNA stability. Cell Rep. Sep. 27, 2012;2(3):674-84.
Novatchkova, et al., The STIR-domain superfamily in signal transduction, development and immunity. Trends Biochem Sci. May 2003;28(5):226-9.
Park, et al. A distinct lineage of CD4 T cells regulates tissue inflammation by producing interleukin 17. Nat Immunol. Nov. 2005;6(11):1133-41.
Patel, et al., Effect of IL-17A blockade with secukinumab in autoimmune diseases. Ann Rheum Dis. Apr. 2013;72 Suppl 2:ii116-23.
Qian, et al. The adaptor Act1 is required for interleukin 17-dependent signaling associated with autoimmune and inflammatory disease. Nat Immunol. Mar. 2007;8(3):247-56.
Qu, et al., TRAF6-Dependent Act1 Phosphorylation by the IκB Kinase-Related Kinases Suppresses Interleukin-17-Induced NF-κB Activation. Mol Cell Biol. Oct. 2012;32(19):3925-37.
Reed, et al., TREX, SR proteins and export of mRNA. Curr. Opin. Curr Opin Cell Biol. Jun. 2005;17(3):269-73.
Ruzankina, et al., Deletion of the developmentally essential gene ATR in adult mice leads to age-related phenotypes and stem cell loss. Cell Stem Cell. Jun. 7, 2007;1(1):113-26.
Rzeczkowski, et al., c-Jun N-terminal kinase phosphorylates DCP1a to control formation of P bodies. J Cell Biol. Aug. 22, 2011;194(4):581-96.
Schoenberg, et al., Regulation of cytoplasmic mRNA decay. Nat Rev Genet. Mar. 6, 2012;13(4):246-59.
She, et al., Structural basis of dcp2 recognition and activation by dcp1. Mol Cell. Feb. 15, 2008;29(3):337-49.
Shen, et al., Structure-function relationships in the IL-17 receptor: implications for signal transduction and therapy. Cytokine. Feb. 2008;41(2):92-104.
Stoecklin, et al., ARE-mRNA degradation requires the 5'-3' decay pathway. EMBO Rep. Jan. 2006;7(1):72-7.
Stumpo, et al., Inflammation: cytokines and RNA-based regulation. Wiley Interdiscip Rev RNA. Jul.-Aug. 2010;1(1):60-80.
Sun, et al., Treatment with IL-17 prolongs the half-life of chemokine CXCL1 mRNA via the adaptor TRAF5 and the splicing-regulatory factor SF2 (ASF). Nat Immunol. Aug. 7, 2011;12(9):853-60.
Swaidani, et al., The critical role of epithelial-derived Act1 in IL-17-and IL-25-mediated pulmonary inflammation. J Immunol. Feb. 1, 2009;182(3):1631-40.
Tiedje, et al., The p38/MK2-driven exchange between tristetraprolin and HuR regulates AU-rich element-dependent translation. PLoS Genet. Sep. 2012;8(9):e1002977.
Toy, et al., Cutting edge: interleukin 17 signals through a heteromeric receptor complex. J Immunol. Jul. 1, 2006;177(1):36-9.
Velichko, et al., A Novel Nuclear Function for the Interleukin-17 Signaling Adaptor Protein Act1. PLoS One. Oct. 10, 2016;11(10):e0163323.
Wang, et al., The hDcp2 protein is a mammalian mRNA decapping enzyme. Proc Natl Acad Sci U S A. Oct. 1, 2002;99(20):12663-8.
Xiao, et al., Phosphorylation of the ASF/SF2 RS domain affects both protein-protein and protein-RNA interactions and is necessary for splicing. Genes Dev. Feb. 1, 1997;11(3):334-44.
Xu et al., Anti-peptide aptamers recognize amino acid sequence and bind a protein epitope. Proc Natl Acad Sci U S A. Jul. 23, 1996;93(15):7475-80.
Zhang, et al., Structure of the unique SEFIR domain from human interleukin 17 receptor A reveals a composite ligand-binding site containing a conserved α-helix for Act1 binding and IL-17 signaling. Acta Crystallogr D Biol Crystallogr. May 2014;70(Pt 5):1476-83.
Zhong, et al., SR proteins in Vertical Integration of Gene Expression from Transcription to RNA Processing to Translation. Mol Cell. Jul. 10, 2009;35(1):1-10.

* cited by examiner

Consensus Structure of an Exemplary SBE Aptamer (SEQ ID NO:1)

Consensus Structure of an Exemplary SBE Aptamer (SEQ ID NO:2)

Consensus Structure of an Exemplary SBE Aptamer (SEQ ID NO:103)

FIG. 16

1. GGAAGAGAACACCUCUUUAUGGCUUACCCUCUAGAAUUUCUAAUUUAUGUGUUCUGUUGAAAUUUUUGUUU
   UUUUACCUUUAUUGAAACAACAAAAAGUCAGUAUUGAAACAUAUCUUCCUGUUUUCUGUUGUCAAAUGAUG
   AUAAUGUGCC  (SEQ ID NO:104)

2. GAGCUGUACCCAGAGAGUCCUGUGCUGAAUGUGGACUCAAUCCCUAGGGCUGGCAGAAAGGGAACAGAAAG
   GUUUUUGAGUACGGCUAUAGCCUGGACUUUCCUGUUGUCUACACCAAUGCCCAACUGCCUGCCUUAGGGUA
   GUGCUAAGAGGAUCUCCUGUCCAUCAGCCAGGACAGUCAGCUCUCUCCUUUCAGGGCCAAUCCCCAGCCCU
   UUUGUUGAGCCAGGCCUCUCUCACCUCUCCUACUCACUUAAAGCCCGCCUGACAGAAACCACGGCCACAUU
   UGGUUCUAAGAAACCCUCUGUCAUUCGCUCCC  (SEQ ID NO:105)

3. CCCUCUGUCAUUCGCUCCCACAUUCUGAUGAGCAACCGCUUCCCUAUUUAUUUAUUUAUUUGUUUGUUUGU
   UUUAUUCAUGGUCUAAUUUAUUCAAAGGGGGCAAGAAGUAGCAGUGUCUGUAAAAGAGCCUAGUUUUUAA
   UAGCUAUGGAAUCAAUUCAAUUUGGACUGGUGUGCUCUCUUUAAAUCAAGUCCUUUAAUUAAGACUGAAAA
   UAUAUAAGCUCAGAUUAUUUAAAUGGGAAUAUUUAUAAAUGAGC  (SEQ ID NO:106)

4. CAUGUAUUUGUUUGCAUAGGUGAUCUCAUUUAAUCCUCUCAACCACCUUUCAGAUAACUGUUAUUUAUAAU
   CACUUUUUUCCACAUAAGGAAACUGGGUUCCUGC  (SEQ ID NO:107)

5. CACAGAGGCAAAAGGAGAAAAUCAUGUUGAAACAAACCGAAAAUGGACAUUGAGAUACUAUCAUUAACAUU
   AGGACCUUAGAAUUUUGGGUAUUGUAAUCUGAAGUAUGGUAUUACAAAACAAACAAACAAACAAAAAACCC
   AUGUGUUAAAAUACUCAGUGCUAAACAUGGCUUAAUCUUAUUUUAUCUUCUUUCCUCAAUAUAGGAGGGAA
   GAUUUUUCC  (SEQ ID NO:108)

6. GGAACUUAAAUAAUGUGAAACUGGAUUAAACUUAAUCUAAAUGGAACCACUCUAUCAAGUAUUAUACCUUU
   UUUAGAGUUGAUACUACAGUUUGUUAGUAUGAGGCAUUUGUUUGAACUGAUAAAGAUGAGUGAGCAUGCCC
   C  (SEQ ID NO:109)

7. CACCUGCAGUGUGUAUUGAGUCUGCUGGACUCCAGGACCUAGACAGAGCUCUCUAAAUCUGAUCCAGGGAU
   CUUAGCUAACGGAAACAACUCCUUGGAAAACCUCGUUUGUACCUCUCUCCGAAAUAUUUAUUACCUCUGAU
   ACCUCAGUUCCCAUUCUAUUUAUUCACUGAGCUUCUCUGUGAACUAUUUAGAAAGAAGCCCAAUAUUAUAA
   UUUUACAGUAUUUAUUAUUUUUAACCUGUGUUUAAGCUGUUUCCAUUGGGGACA  (SEQ ID NO:110)

8. CUCUUUGACCAAUUAAUUAUUCUUUCUGACUAAUUAGCCAAGACUGUGAUUGCGGGGUUGUAUCUGGGGGU
   GGGGGACAGCCAAGCGGCUGACUGAACUCAGAUUGUAGCUUGUACCUUUACUUCACUGACCAAUAAGAAAC
   AUUCAGAGCUGCAGUGACCCCGGGAGGUGCUGCUGAUGGGAGGAGAUGUCUACACUCCGGGCCAGCGCUUU
   AACAGCAGGCCAGACAGC  (SEQ ID NO:111)

SBE APTAMERS FOR TREATING IL-17A RELATED DISEASES AND CONDITIONS

The present application claims priority to U.S. Provisional application 62/535,559, filed Jul. 21, 2017, which is herein incorporated by reference in its entirety.

STATEMENT REGARDING FEDERAL FUNDING

This invention was made with government support under HL103453, CA062220, HL029582 awarded by the National Institutes of Health and RG5130A2/1 awarded by National Multiple Sclerosis Society. The government has certain rights in the invention.

FIELD

Provided herein are compositions, systems, kits, and methods for treating IL-17a related diseases and conditions using an SBE nucleic acid sequence that binds a SEFIR domain of an ACTT protein.

BACKGROUND

Interleukin 17 (IL-17, also known as IL-17A) is a key signature cytokine of Th17 cells and is also produced by innate immune cells (Harrington et al., 2005; Park et al., 2005; Cua and Tato, 2010). While IL-17 is required for host defense against extracellular microorganisms (Cho et al., 2010; Conti et al., 2009; Kolls and Khader, 2010; Milner and Holland, 2013), IL-17 plays a critical role in the pathogenesis of autoimmune and inflammatory diseases, including psoriasis, rheumatoid arthritis, multiple sclerosis, and asthma (Swaidani et al., 2009; Kang et al., 2010; Bulek et al., 2011; Patel et al., 2013).

IL-17 signals through a heterodimeric receptor complex composed of IL-17RA and IL-17RC (Shen and Gaffen, 2008; Toy et al., 2006). Both IL-17RA and IL-17RC belong to a SEFIR protein family, which is defined by the presence of a conserved cytoplasmic SEFIR domain (Novatchkova et al., 2003). Act1 (also known as CIKS) is an essential component in IL-17 signaling and also a member of the SEFIR protein family (Li et al., 2000; Chang et al., 2006; Qian et al., 2007). Upon IL-17 stimulation, Act1 is recruited to IL-17R through a SEFIR-dependent interaction. Act1 in turn engages members of the TRAF family, activating NFkB, C/EBP, and MAPK pathways. IL-17-Act1-mediated signaling results in transcription of pro inflammatory and neutrophil-mobilizing cytokines and chemokines, including CXCL1, TNF, IL-6 and GM-CSF (Gu et al., 2013).

While IL-17 activates gene transcription of cytokines and chemokines, it is equally important for IL-17 to stabilize otherwise unstable mRNAs for the induction of the pro-inflammatory genes. Cytokine and chemokine mRNAs have short half-lives because of conserved cis-elements, including AU-rich elements (AREs) and stem-loop (SL) structures in their 3' UTRs (Leppek et al., 2013; Stoecklin et al., 2006a). The AREs within the 3' UTR can be recognized by RNA binding proteins (including TTP, AUF1, KSRP and SF2) that function to mediate the sequential deadenylation, decapping, and ultimately exonucleolytic degradation of the RNA (Schoenberg and Maquat, 2012; Stumpo et al., 2010). Notably, P-bodies are sites of mRNA degradation. Stress granules form in response to stress, are sites of RNA triage, and can deliver mRNAs to P-bodies for decay. Recent studies have reported that SLs present in immune-related mRNAs, including TNF and IL-6, are destabilized by RNA binding proteins Roquin and Regnase-1. Roquin destabilizes translationally inactive mRNAs that are accumulated in processing-bodies (P-bodies) and stress granules. Regnase-1 specifically cleaves and degrades translationally active mRNAs bound to polysomes (Mino et al., 2015). Although multiple mRNA destabilizing mechanisms have been discovered, there is still a significant gap in knowledge as to how the mRNAs of inflammatory genes are selectively stabilized and successfully translated in response to an inflammatory stimulus, e.g. IL-17 stimulation.

SUMMARY

Provided herein are compositions, systems, kits, and methods for treating IL-17a related diseases and conditions using an SBE nucleic acid sequence that binds a SEFIR domain of an ACT1 protein.

In some embodiments, provided herein are methods of treating an IL-17a related disease or condition comprising: treating a subject with an IL-17a related disorder or condition with a composition, wherein the composition comprises a first nucleic acid sequence, wherein the first nucleic acid sequence comprises an SBE nucleic acid sequence that binds a SEFIR domain of an ACT1 protein. In certain embodiments, the treating reduces or eliminates at least one symptom related to the IL-17a related disease or condition. In further embodiments, the IL-17a related disease is selected from the group consisting of: psoriasis, chronic plaque, asthma, an autoimmune disease, an inflammatory condition, rheumatoid arthritis, and multiple sclerosis. In particular embodiments, the subject is a human or other mammal.

In additional embodiments, provided herein are compositions comprising a first nucleic acid sequence, wherein the first nucleic acid sequence comprises an SBE nucleic acid sequence that binds a SEFIR domain of an ACT1 protein, and wherein the first nucleic acid sequence comprises modified bases to improve stability in vivo.

In particular embodiments, provided herein are compositions comprising a first nucleic acid sequence, wherein the first nucleic acid sequence comprises an SBE nucleic acid sequence that binds a SEFIR domain of an ACT1 protein, and wherein the SBE nucleic acid sequence comprises a sequence shown in SEQ ID NO:1, 2, or 103, but which is not naturally occurring.

In further embodiments, at least a portion of the SBE nucleic acid sequence is from a gene selected from CXCL1, GM-CSF, IL-6, and TNF. In further embodiments, the SBE nucleic acid sequence comprises a sequence shown in SEQ ID NOs:1-2, 49-61, 88-94, and 99-129. In regard to SEQ ID NOS:1 and 2, the N's in these sequences are independently selected from A, G, C, T, U, as well as modified and non-canonical nucleotide bases. Candidate sequences that are constructed based on the variability in SEQ ID NOS:1, 2, and 103 may be screened in the same assays employed in Example 1 to determine if they bind a SEFIR domain of an ACT1 protein.

In certain embodiments, the SBE nucleic acid sequence comprises RNA bases (e.g., all or most of the SBE nucleic acid sequence is composed of RNA bases). In other embodiments, the SBE nucleic acid sequence comprises DNA bases (e.g., all or most of the SBE nucleic acid sequence is composed of DNA bases). In some embodiments, the SBE nucleic acid sequence comprises, consist of, or consists essentially of: nucleotides 810-857 of the CXCL1 gene, ii) nucleotides 830-856 of the CXCL1 gene, or iii) nucleotides 800-835 of the CXCL1 gene. In further embodiments, the SBE nucleic acid sequence is from a human gene, or has 1 or 2 conservative amino acid substitutions compared to the SBE sequence from a human gene.

In some embodiments, the ACT1 protein is human ACT1 protein or other mammalian ACT1 protein. In further embodiments, the first nucleic acid sequence is between 12 and 70 nucleotides in length. In additional embodiments, the first nucleic acid is present in the composition at a level that is therapeutic when administered to a subject with an IL-17a related disease or condition (e.g., for administration to a human).

RNA decay in HeLa cells transfected with or without 100 pmoles/ml of SBE RNA aptamers (WT or mutant C), pre-treated with TNF (10 ng/ml) for 1 hour and then treated with Actinomycin D alone (NT) or in the presence of IL-17 (50 ng/ml) for 45 and 90 minutes. Human CXCL1, GM-CSF and TNF mRNAs were measured by RT-PCR, normalized to GAPDH and presented as half-life. F. HeLa cells transfected with or without 100 pmoles/ml of SBE RNA aptamers (WT or mutant C) were pre-treated with TNF (10 ng/ml) for 1 hour followed by stimulation with IL-17A (50 ng/ml) for 6, 8 or 24 hours. Supernatants of the treated cells were then analyzed by ELISA. Data are representative of two independent experiments, and analyzed by two-tailed Student's t-test. Data represent mean±SD; *, p<0.05, **, p<0.01.

Figure 7:
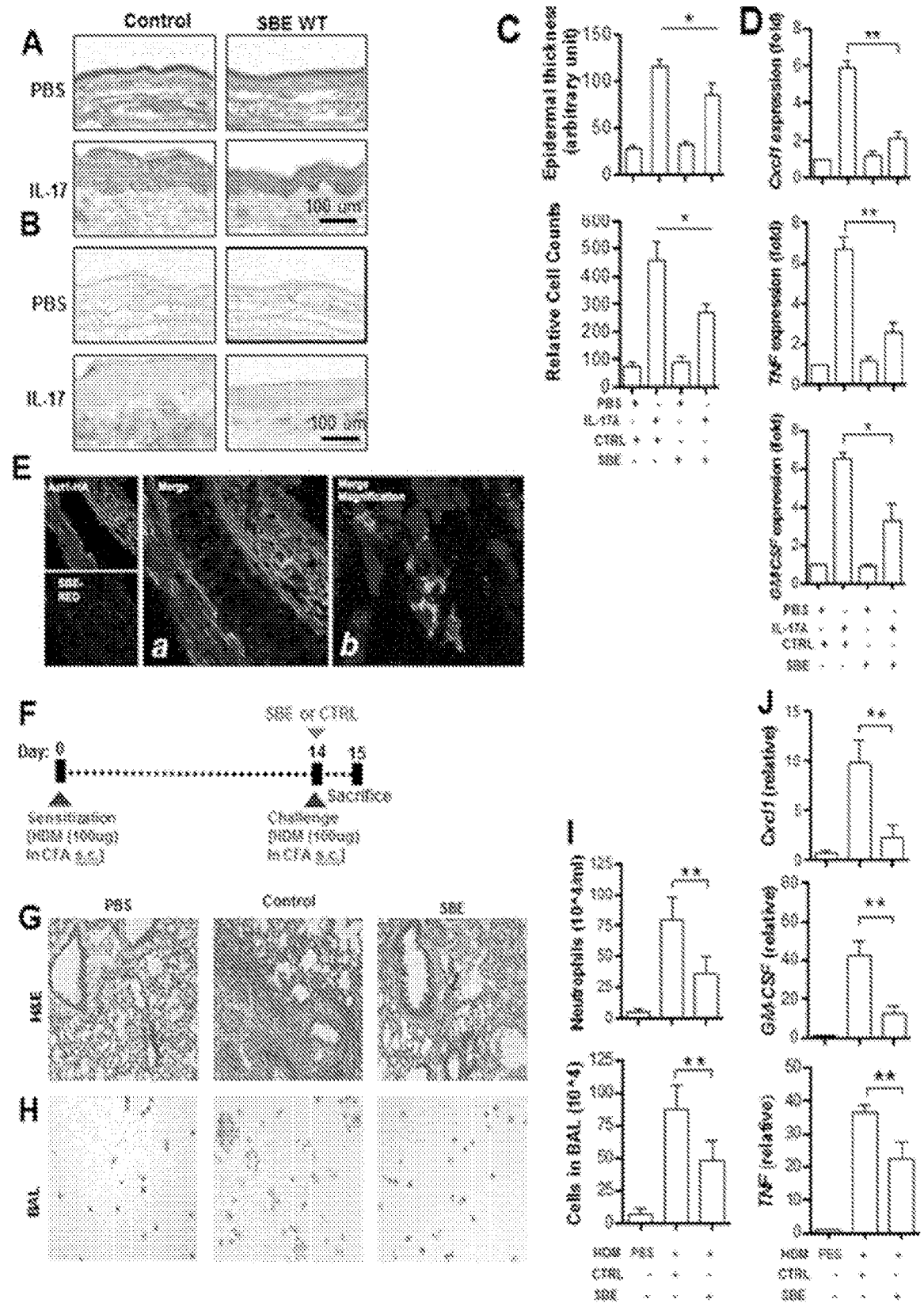

FIG. 7. SBE RNA aptamers inhibited IL-17-dependent skin hyperplasia A. H&E staining of ear skin tissue from C57BL/6J mice injected intradermally with IL-17A (500 ng) or PBS together with methylated (Materials and methods) SBE RNA aptamers [SBE mutant C (1 nmol) as a negative control or SBE WT aptamer (1 nmol)] for 6 consecutive days. B. Paraffin sections of the ear skin from A were subjected to immunohistochecmitry staining for Ly6G. C. Epidermal thickness of ear skin from A were measured in arbitrary units and the average number of Ly6G+ cells per section from B were counted. 5 fields were analyzed for each mouse under 20× magnification. Scale bar is 100 µm. Data are analyzed by two-tailed Student's t-test; *, p<0.05, t-test. Data represent mean±S.E.M of biological replicates (n=6 mice/group). D. RT-PCR analysis of mRNA isolated from the ear skin tissue as described in A. Expression of Act1-target genes was graphed as mean fold induction over PBS+ control aptamer treated group. Data represent mean±SEM of biological replicates (n=6 mice/per group) and. Two-tailed Student's t-test were used to analyze the data. **, p<0.01, *, p<0.05.

Figure 8:
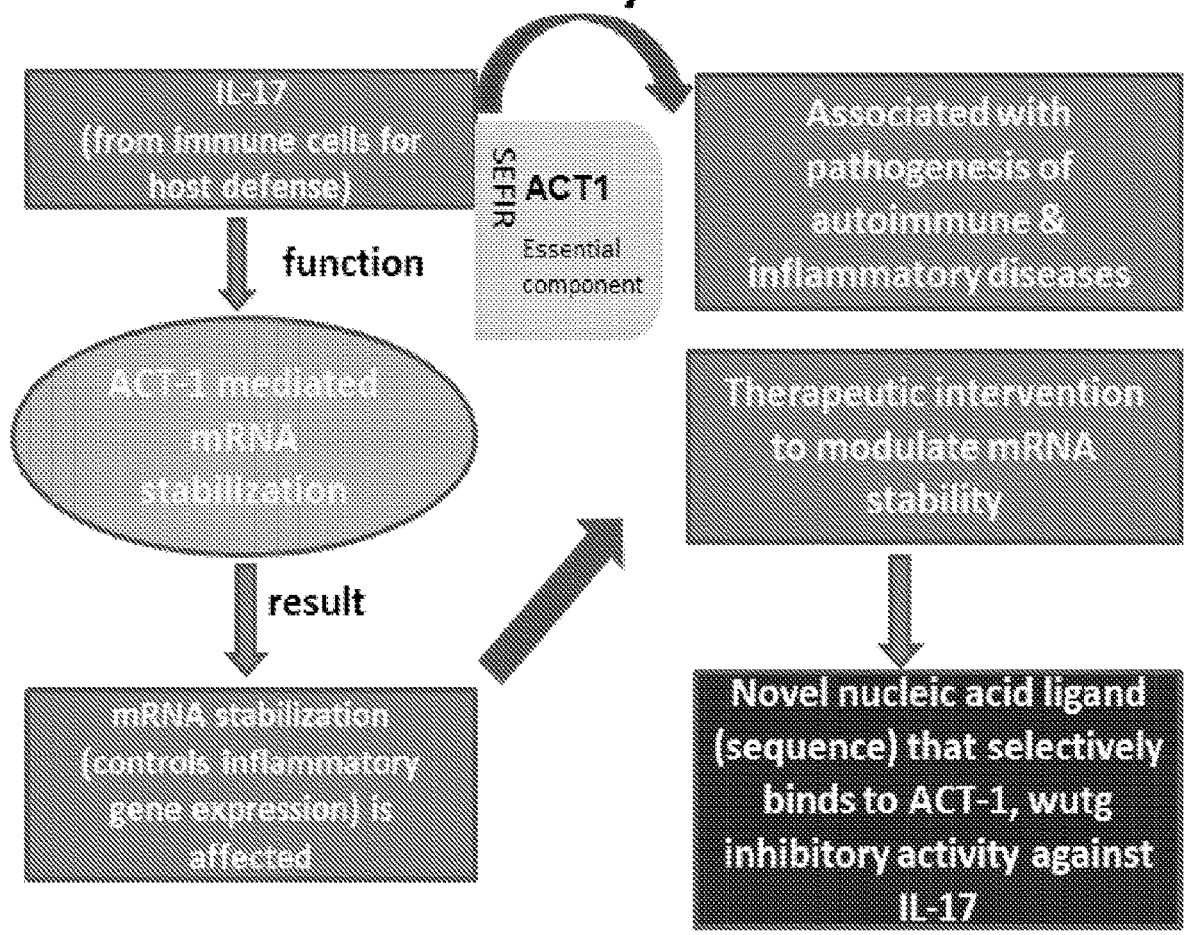

FIG. 8 shows a hypothetical, non-limiting, mechanism of ACT-1 mediated mRNA stabilization affecting inflammatory gene expression in pathogenesis of autoimmune and inflammatory diseases, and therapeutic intervention with nucleic acid sequences that selectively binding ACT1 with inhibitory activity against IL-17.

Figure 9:
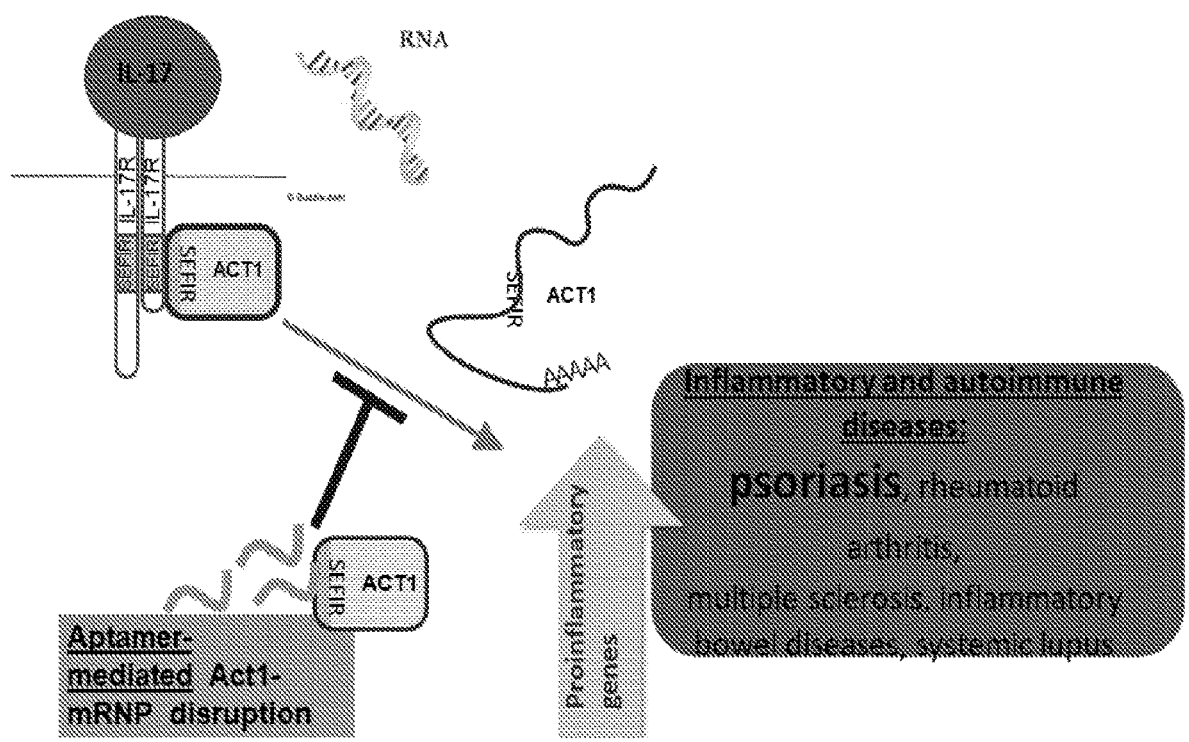

FIG. 9 shows a hypothetical, non-limiting, mechanism of using aptamer-mediated Act1-mRNA disruption, to treat inflammatory and autoimmune diseases, such as psoriasis, rheumatoid arthritis, multiple sclerosis, inflammatory bowel diseases, and systemic lupus.

Figure 10:
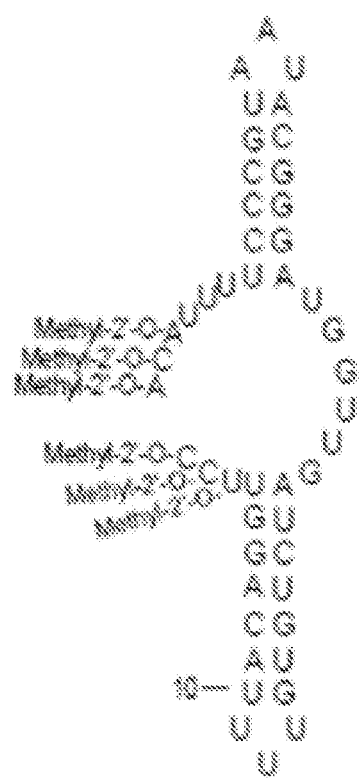

FIG. 10 shows an SBE from the mouse CXCL1 mRNA that is 2'-O-methylated (SEQ ID NO:80), including the step and loop secondary structure formed by this sequence.

Figure 11:
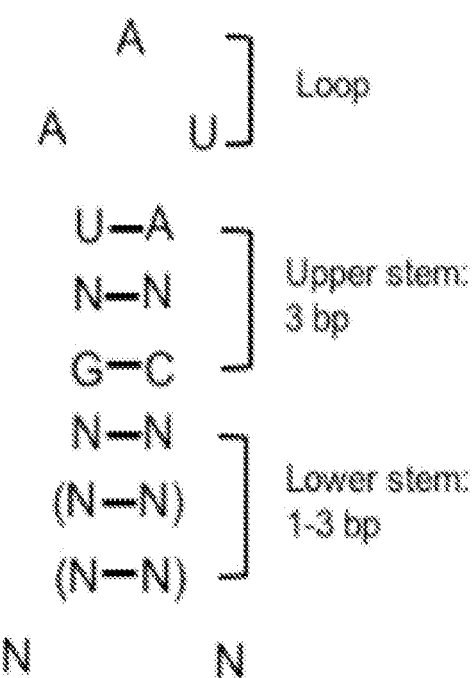

FIG. 11 shows a consensus structure of an exemplary SBE nucleic acid aptamer (SEQ ID NO:1). The N's in these sequences are independently selected from A, G, C, T, U, as well as modified and non-canonical nucleotide bases. As can be seen, if a particular N is chosen, the base it is hybridized to must be a corresponding base (e.g., if "G" is chosen, the hybridized base will be "C").

Figure 12:
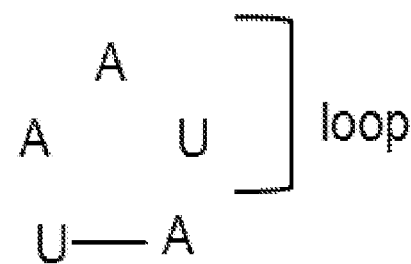

FIG. 12 shows a consensus structure of an exemplary SBE nucleic acid aptamer (SEQ ID NO:2). The N's in these sequences are independently selected from A, G, C, T, U, as well as modified and non-canonical nucleotide bases.

Figure 13:
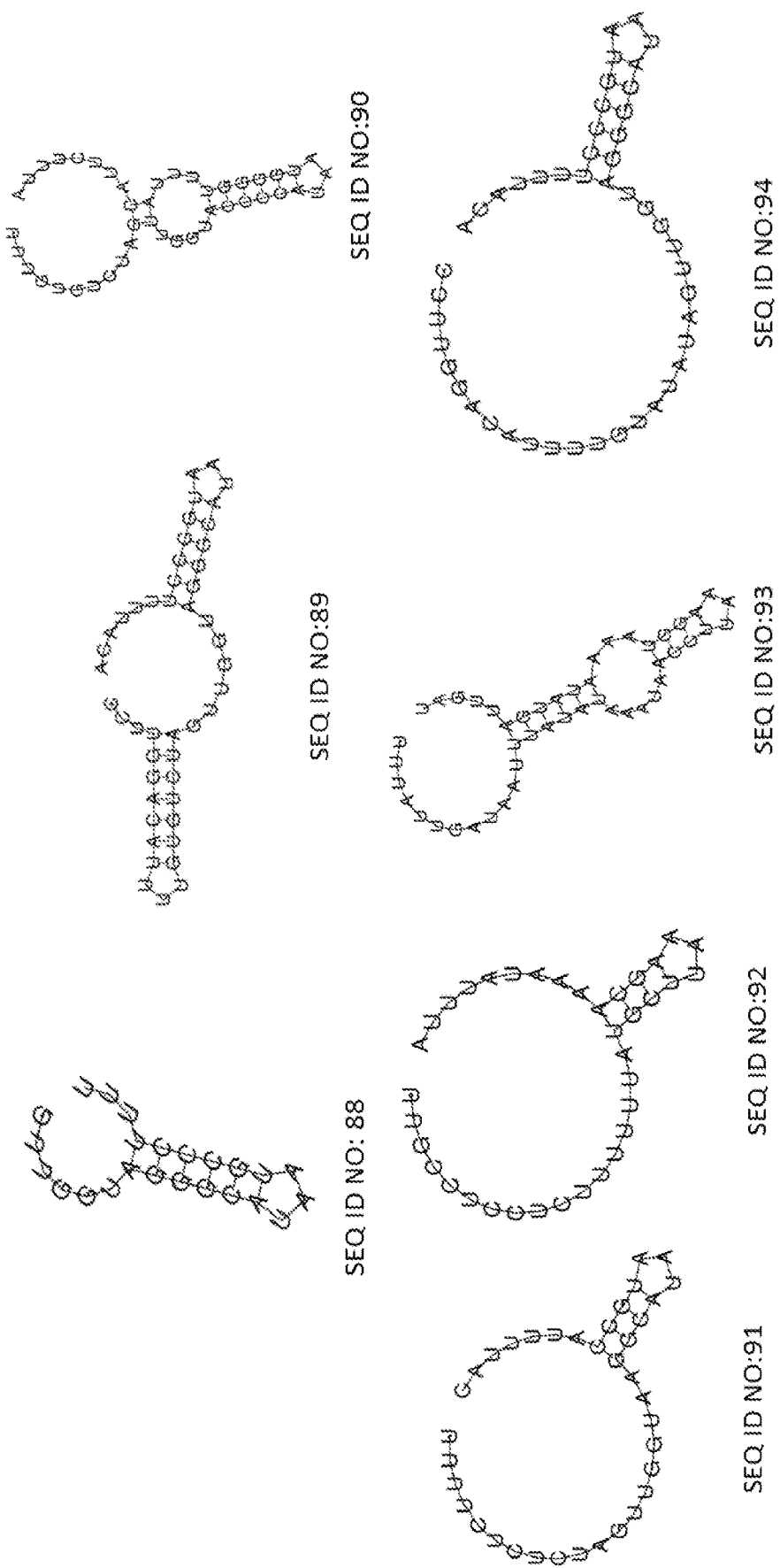

FIG. 13 shows seven exemplary SBE nucleic acid aptamers (SEQ ID NOS:88-94).

Figure 14:
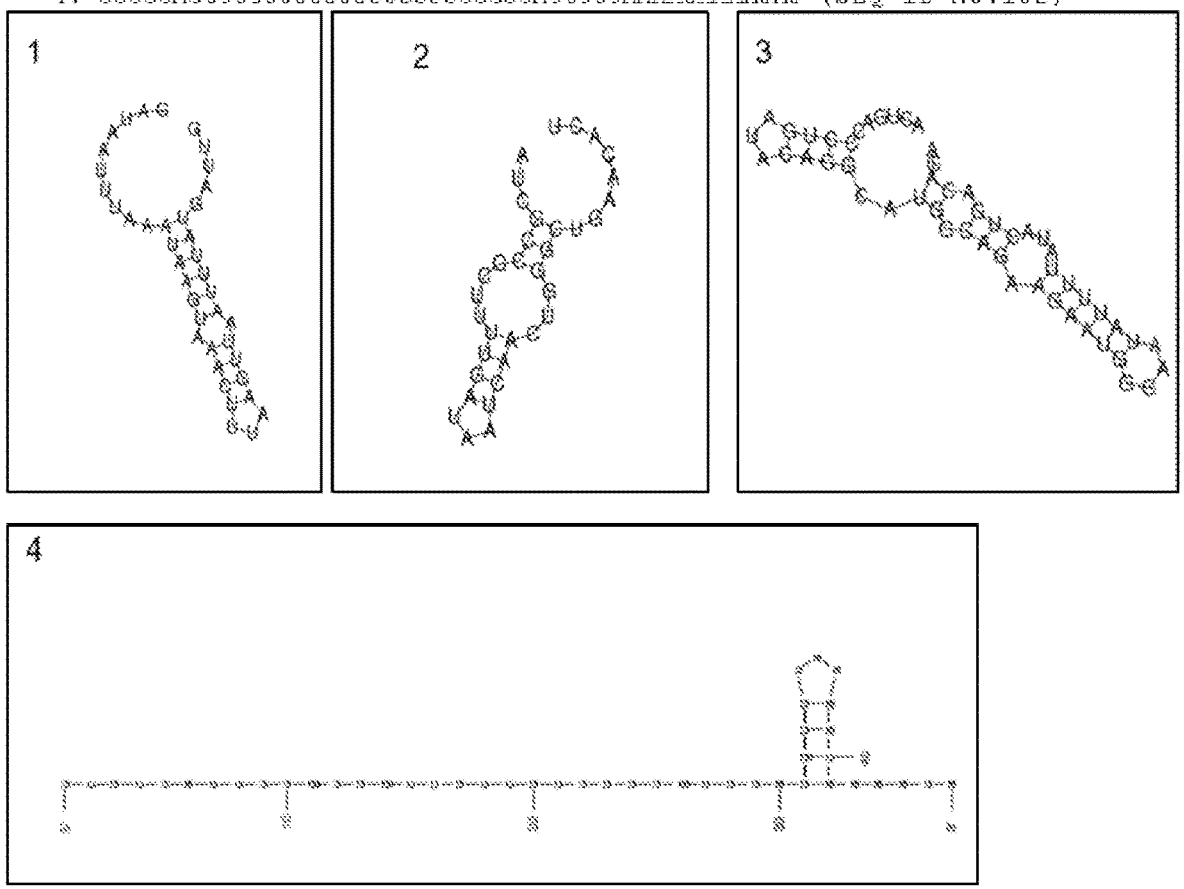

FIG. 14 shows four exemplary SBE nucleic acid aptamers (SEQ ID NOS:99-102).

FIG. 15 shows a consensus structure of an exemplary SBE nucleic acid aptamer (SEQ ID NO:103), where the three "Ws" are either A or U (e.g., AAA, AUA, UUA, UUU, UAU, etc.).

FIG. 16 shows eight exemplary SBE nucleic acid sequences (SEQ ID Nos:104-111) that showed positive results when tested by EMSA in work conducted during development of embodiments of the present disclosure.

DETAILED DESCRIPTION

Provided herein are compositions, systems, kits, and methods for treating IL-17a related diseases and conditions using an SBE nucleic acid sequence that binds a SEFIR domain of an ACT1 protein. In certain embodiments, the SBE nucleic acid sequences (aptamers) comprise RNA and/or DNA, and are between 10 and 65 nucleotides in length. In certain embodiments, the SBE aptamer forms a stem and loop type structure.

Proinflammatory cytokine IL-17, a major driver of autoimmunity, signals through a heterodimeric receptor complex (IL-17RA and IL-17RC), which interacts with the SEFIR-containing adaptor, Act1. Work conducted during the development of embodiments descried herein found that Act1 has a non-canonical function as an RNA binding protein that stabilizes otherwise unstable mRNAs of the pro-inflammatory genes in response to IL-17 stimulation including CXCL1, TNF, GM-CSF, as well as IL-6. Structure-functional analysis showed that the SEFIR domain is necessary and sufficient for the RNA binding activity of Act1. While the present invention is not limited to any particular mechanism, and an understanding of the mechanism is not necessary to practice the invention, it is believed that Act1 directly binds to a stem-loop structure in the 3'UTR of the mRNAs in P-bodies, inhibiting their decapping by bringing a kinase, TBK1 to phosphorylate and disrupt Dcp1/Dcp2 complex. RNA oligos containing the Act1 RNA binding motif abolished Act1's localization in P-bodies and prevented Act1-mediated mRNA stabilization. Taken together, these results support a new paradigm in which the receptor-proximal adaptor Act1 directly controls mRNA metabolism, providing a mechanism for receptor-mediated selectivity of mRNA stabilization during inflammation.

Work conduced herein has shown that Act1, an interleukin-17 (IL-17) receptor complex adaptor, binds and stabilizes mRNAs encoding key inlammmatory proteins. The Act1 SEFIR domain binds a stem-loop structure, SBE (SEFIR-binding element), in the CXCL1 3'UTR. Remarkably, mRNA-bound Act1 directs formation of three compartmentally-distinct RNPs that regulate three disparate events in inflammatory mRNA metabolism, preventing SF2-mediated mRNA decay in the nucleus, inhibiting Dcp1/2-mediated mRNA decapping in P-bodies, and facilitating HuR binding to polysomal mRNA to promote translation. SBE RNA aptamers reduced IL-17-mediated mRNA stabilization in vitro, and IL-17-induced skin inflammation, providing a new therapeutic strategy for autoimmune diseases and related conditions. While the present invention is not limited to any particular mechanism, and an understanding of the mechanism is not necessary to practice the invention, it is believed, taken together, these results reveal an extraordinary network in which Act1 assembles RNPs on the 3'UTRs of select mRNAs to control receptor-mediated mRNA stabilization and translation during inflammation.

In certain embodiments, provided herein are SBE aptamers, which may be used to treat IL-17a disease or conditions. In certain embodiments, the SBE aptamer is a single stranded RNA or DNA oligonucleotide (e.g., 12mer-70mer, such as a 56-mer) that binds to ACT1 and inhibits the activity of IL-17a. In certain embodiments, the SBE aptamers are, compared to antibodies, are smaller in size, lipophilic and enter cells more easily, and have lower immunogenicity. In particular embodiments, the SBE aptamers inhibit IL-17 mediated mRNA stabilization. In particular embodiments, the SBE aptamers recognize ACT-1 (through binding) with specificity. In certain embodiments, the SBE aptamers inhibit IL-17 in vivo without losing the antibacterial and anti-fungal function of IL-17. In certain embodiments, the SBE aptamers are further chemically modified to improve affinity and/or increase stability (e.g., 2'-O-methylation). In some embodiments, the SBE aptamers, at one or more pyrimidine nucleotides, modifications are made at the 2'-sugar or base for improved affinity and/or stability.

IL-17a is a known target in the pathogenesis of many inflammatory and autoimmune diseases. COSENTYX (secukinumab) is a selective binding to IL-17 which is approved in the EU for the treatment of Psoriasis. The SBE aptamers herein may be used as alternative therapy to secukinumab to treat Psoriasis or other autoimmune diseases.

In certain embodiments, the SBE nucleic acid aptamer sequence is selected from SEQ ID NOS:2 and 88-94, which are shown in FIGS. 12 and 13, and in Table 4 below.

TABLE 4

| | |
|---|---|
| N1GN2UAAUAN3CN4 (N1/N4, N2/N3 = G/C or A/U) | SEQ ID NO: 2 |
| GUUGGUAGGGCAUAAUGCCCUUUU | SEQ ID NO: 88 |
| CCUUGGACAUUUUGUGUCUAGUUGGUAGGGCAUAAUGCCCUUUUACA | SEQ ID NO: 89 |
| UUUGUGUCUAGUUGGUACCCCAUAAUGGGGUUUUACAUUCUUUA | SEQ ID NO: 90 |
| UUUUCUCUCUAGUUGGUAAGGCAUAAUGCCAUUUUAC | SEQ ID NO: 91 |
| UUGCCUCCUCUUUUUUAUGCUUAAAGCAAAAUAUUUA | SEQ ID NO: 92 |
| UUUAUUGAUAAUUUAUAUAAAUAACCUUAAAGGUAAAAUAUGAUUGAU | SEQ ID NO: 93 |
| CCUUGGACAUUUUGUAUAUAGUUGGUAGGGCAUAAUGCCCUUUUACA | SEQ ID NO: 94 |

In certain embodiments, the SBE nucleic acid aptamer sequence is selected from SEQ ID NOS:112-129, which are shown in Table 7 below (where N is selected from A, T, G, C, and U).

TABLE 7

| | |
|---|---|
| NNNNNNNNNNNNAGAUAAUAUCUNNNNNNNNNNNNNN | SEQ ID NO: 112 |
| NNNNNNNNNNNNCGAUAAUAUCGNNNNNNNNNNNNNN | SEQ ID NO: 113 |
| NNNNNNNNNNNNAGCUAAUGUCUNNNNNNNNNNNNNN | SEQ ID NO: 114 |
| NNNNNNNNNNNNCGCUAAUAGCGNNNNNNNNNNNNNN | SEQ ID NO: 115 |
| NNNNNNNNNNNNUGAUAAUAUCANNNNNNNNNNNNNN | SEQ ID NO: 116 |
| NNNNNNNNNNNNUGUUAAUAACANNNNNNNNNNNNNN | SEQ ID NO: 117 |
| NNNNNNNNNNNNGGAUAAUAUCCNNNNNNNNNNNNNN | SEQ ID NO: 118 |
| NNNNNNNNNNNNAGGUAAUACCUNNNNNNNNNNNNNN | SEQ ID NO: 119 |
| NNNNNNNNNNNNGGGUAAUACCCNNNNNNNNNNNNNN | SEQ ID NO: 120 |
| NNNNNNNNNNNNAGUUAAUAACUNNNNNNNNNNNNNN | SEQ ID NO: 121 |
| NNNNNNNNNNNNAAGAAAAUCUNNNNNNNNNNNN | SEQ ID NO: 122 |
| NNNNNNNNNNNNAAGAAUAUCUUNNNNNNNNNNNN | SEQ ID NO: 123 |
| NNNNNNNNNNNNAAGAAAUUCUUNNNNNNNNNNNN | SEQ ID NO: 124 |

TABLE 7-continued

| | |
|---|---|
| NNNNNNNNNNNNAAGAAUUUCUUNNNNNNNNNNNN | SEQ ID NO: 125 |
| NNNNNNNNNNNNAAGAUAAUCUUNNNNNNNNNNNN | SEQ ID NO: 126 |
| NNNNNNNNNNNNAAGAUAUUCUUNNNNNNNNNNNN | SEQ ID NO: 127 |
| NNNNNNNNNNNNAAGAUUAUCUUNNNNNNNNNNNN | SEQ ID NO: 128 |
| NNNNNNNNNNNNAAGAUUUUCUUNNNNNNNNNNNN | SEQ ID NO: 129 |

In certain embodiments, one, two, or three nucleotide substitutions are made to SEQ ID NOS:88-94 and 99-129, such as a conservative substitution that does not substantially change the stem and loop structures shown in FIG. 13 or 14. In other embodiments, one, two, or three nucleotides are deleted from the 5' end, the 3' end, or both the 5' and 3' ends of SEQ ID NOS:88-94 and 99-129 to generate truncated versions thereof.

In some embodiments, the additional SBE nucleic acid sequence aptamers that bind ACT1 SEFIR domain can be identified. Provided in Table 6 below is 644 transcripts that are stabilized by IL-17 stimulation in cultured keratinocytes. These transcripts, as well as mutated versions of SEQ ID NOS:88-94 and 99-129, could be screened for SBE sequences that bind ACT1 SEFIR domain. For example, one identify SBE aptamers from the 3'UTRs of the transcripts in the gene list in Table 6 by measuring the binding of an RNA aptamer containing sequence derived from the aforementioned 3' UTRs to purified Act1 SEFIR protein (SEQ ID NO:95, rkvfitysmdtamevvkfvnfllvngfqtaidifedrirgidiikwm erylrdktvmiivaispkykqdvegaesqldedehglhtkyihrmmqiefisqgsmnfrfipvlfpnakkeh vptwlqnthvyswpknkknillrllree) using electrophoretic mobility shift assay (EMSA), surface plasmon resonance assay or microscale thermophresis assay (see Example 1 further below for conditions and procedures). Candidate RNA aptamers that bind to Act1-SEFIR protein are considered SBE aptamers, which have the potential of ameliorating IL-17 mediated diseases.

The identified SBE can be further tested for their ability to inhibit IL-17 induced mRNA stability. To this end HeLa cells could be transfected with or without 100 pmoles/ml of SBE RNA aptamers, pre-treated with TNF (10 ng/ml) for 1 hour and then treated with Actinomycin D alone (NT) or in the presence of IL-17 (50 ng/ml) for 45 and 90 minutes. Human CXCL1, GM-CSF and TNF mRNAs could be measured by RT-PCR, normalizedto GAPDH and presented as half-life. Supernatants of the treated cells are analyzed by ELISA. SBE aptamers that can reduce the half-life of CXCL1, GM-CSF, and TNF transcripts and blunt their protein expression are bona fide SBE aptamers that can be used to treat IL-17 mediated diseases such as psoriasis, severe asthma and cancer.

TABLE 5

Example SBE element identified from 3'UTRs of transcripts in Table 6

| | |
|---|---|
| CTTTTGCTTATGTTTAAAACAAAAT (SEQ ID NO: 96) | TNF derived SBE |
| AGTAAACTTTAAGTTAATTTAUG (SEQ ID NO: 97) | GMCSF derived SBE |
| CTGACCCTGATACAGGCATGGCA (SEQ ID NO: 98) | IL-6 derived SBE |

TABLE 6

| GENE NAME | | | | | |
|---|---|---|---|---|---|
| Cxcl1 | Il13ra2 | Gzmf | Klrb1f | Trim50 | Fgd5 |
| Tnf | Arl9 | Tmem125 | Stoml3 | Tmem52 | Gsdmcl1 |
| Csf2 | Opn1mw | Nobox | Apeg3 | Atp6v1b1 | H2-Q7 |
| Il6 | Dppa3 | Zg16 | Igll1 | Rab33a | Stmn3 |
| Saa3 | Hs3st6 | Fcamr | Ifnk | Bpifa2e | Tcfap2c |
| Camp | Il17c | Sprr2k | Efcab3 | Glp2r | Pnma5 |
| Serpina3i | Lect2 | Ccl24 | Gtsf1l | Olfr1450 | Tmem145 |
| Mir16-2 | Al428936 | Niacr1 | Smtnl1 | Cacng4 | Cdr1 |
| Mir345 | Atp6v1c2 | Clec2f-ps | Mospd4 | Nos2 | Gpr87 |
| Hist1h2ad | Cd300c | Lce1l | Cplx4 | Spata21 | Cidea |
| Mir350 | Olfr1420 | C2cd4b | Ctf2 | H2-Q8 | H2-Bl |
| Hils1 | Gzmc | Dleu7 | Syce1l | Avp | Tmem196 |
| Mir674 | Capsl | Cyp1a1 | Prl8a8 | Pxt1 | Alms1-ps2 |
| Mir1970 | Dnajc5b | Treh | Vmn1r38 | Tceal5 | Olfr1182 |
| Mir297b | Gngt1 | Ltb4r1 | Igfbpl1 | Lhb | Mmel1 |
| Mir449c | Gpx2-ps1 | Ascl3 | Nepn | H2-M9 | Serpina7 |
| Mir199b | Apoc1 | C1ql4 | Olfr992 | Cxcl3 | Xlr4a |
| Rfpl3s | Krt23 | Tmem163 | Faim2 | Tcl1b4 | Gstm3 |
| Olfr1314 | Msmb | Iapp | Prl8a9 | Tssk3 | Ssxb5 |
| Bglap2 | Mmp21 | Cd300lh | Tas2r140 | Ms4a10 | Cpne7 |
| Scarna8 | Pkp3 | Vgll2 | Olfr577 | Hrasls5 | Cldn27 |
| Lcn2 | Gpr84 | Fbxw13 | Spaca3 | Trem3 | Iqub |
| Mir1192 | Taar7d | Plcd4 | Olfr1278 | Olfr421 | Slc6a19 |
| Mir669h | Tcte3 | Lipn | Olfr457 | Nctc1 | Lypd6 |
| Snora62 | Olfr419 | Ppef2 | Morn3 | Slc4a9 | Marveld3 |
| Otor | BC024582 | Unc93a | Tnip3 | St8sia5 | Slc25a41 |
| Vmn1r40 | Csn2 | C4a | Olfr429 | Tmprss2 | Trpc3 |
| Gng13 | Serpina3f | Helt | Atp6v1g3 | Nkx2-4 | Btnl9 |
| Cd83 | Tpte | Slc5a11 | Olfr1474 | Olfr374 | Myh7b |
| Cited4 | Wisp3 | Cacng6 | Olfr1475 | Sox7 | Zfhx2as |
| Kcnk15 | Oaz3 | Tuba3b | Cma2 | Olfr172 | Fcgr4 |
| Morn5 | Darc | Slc2a7 | Slc6a20a | Kcng4 | Trim63 |
| Colec11 | Otud6a | Prss42 | Vmn1r205 | Rlbp1 | Foxl2 |
| Ly6d | Cxcl5 | Slc15a2 | Olfr1418 | A4gnt | Olfr225 |
| Art1 | Krt8 | Tdrd12 | Olfr572 | Spata3 | Gpx6 |
| Tmem212 | Npw | Gp9 | Fmr1nb | Speer1-ps1 | Rnf186 |
| Ppbp | Mx2 | Cyp2d26 | Olfr1347 | Pate2 | Spata22 |
| Trp53tg5 | Gabrr2 | Ribc2 | Xkr9 | Elf5 | Tekt5 |
| Catsper3 | Gpr97 | Myo1g | Serpinb9c | Nsg2 | Fcrlb |
| Rpp25 | Prrt1 | Pnpla3 | Olfr726 | Hs3st1 | Prss40 |
| Il12a | Apobec4 | Fam151a | Wnt9b | Hes5 | Wnt3 |
| Fam50b | Dpf3 | Cct8l1 | Zfp352 | Srms | Fstl4 |
| C2cd4d | Zdhhc22 | Olfml1 | Apol11a | Vmn2r21 | Oca2 |
| Hrh3 | Hsd3b5 | Hoxd11 | Kif2b | Vmn2r15 | Sox17 |
| Itgad | Amph | Inhbc | Pabpn1l | Pabpc2 | Ptpn5 |
| Ccdc54 | Pnliprp1 | Sigirr | Dgki | Vmn2r38 | Igdcc3 |
| Il1b | Prb1 | Mmp1b | BB123696 | Ly6h | Ntn5 |
| Clec4a3 | Kbtbd12 | Prss55 | Slc27a2 | Pcdha7 | Prdm13 |
| Nat1 | Lrrc3b | Zp3r | Asb10 | Pcdha6 | Samd7 |
| Serpina4-ps1 | Kcng3 | H2-Q1 | Wfdc5 | Ppp1r1c | Il7r |
| Fam123a | Fbxo40 | Tex19.2 | Barhl2 | Slfn4 | Hoxa9 |
| Rpl31 | Mcoln3 | Prf1 | Sec14l5 | Scnn1b | Foxo6 |
| Gdf3 | Plcb2 | Hapln2 | Spock1 | Gpr128 | Lst1 |
| Il27 | Steap4 | Il4i1 | Capn9 | Dmbx1 | Ptchd3 |
| Abp1 | Hsd17b13 | Cyp3a41b | Adam30 | Cwh43 | Ankmy1 |
| Lta | Bpifb2 | Fam115e | Fam43b | Csprs | Nefm |
| Batf2 | Lim2 | Mrap2 | Slc47a2 | Tyrp1 | Ffar3 |
| Tlx2 | Epb4.2 | Kcne1 | Ccl20 | Adam29 | Cd101 |
| Fam19a4 | Treml4 | Plk5 | Cldn10 | Zfp957 | Klhl4 |
| Prss32 | Slc22a3 | Dyrk4 | Mageb4 | D6Ertd474e | Gabrp |
| Aanat | Tacstd2 | Vax2os1 | Pou6f2 | Slc35f3 | Ccdc129 |
| H2-Q10 | P2ry4 | Il25 | Clcnka | Slco1a6 | Clec9a |
| Cldn14 | Oxct2a | Tgm7 | Syt1 | Nell1 | Frem3 |
| Atp1b2 | Itpka | Asb15 | Gpr132 | Pglyrp2 | Car10 |
| Zic2 | Dlx4 | Bpifb9a | Rbpjl | Tnfrsf9 | BC147527 |

TABLE 6-continued

| GENE NAME | | | | | |
|---|---|---|---|---|---|
| Fam187b | Klk14 | Snap25 | Krt1 | Cacng2 | Nlrp4e |
| Klf14 | Ggt6 | Fam19a3 | Speer4f | Serpinc1 | Syt2 |
| Grin2a | Uox | Serpina5 | Clec2g | Aurkc | Ccdc146 |
| Arl11 | Rit2 | Hpse2 | Il22ra2 | Ubxn10 | Ms4a15 |
| Tssk5 | Alx3 | Tbc1d21 | Prss38 | Cckar | Krt78 |
| Camkv | Epsti1 | H2-Q2 | Capn8 | Fam163b | Oasl2 |
| Wnt8a | Padi1 | Zcchc12 | Tmem90a | Foxb1 | Il1a |
| Fbxw15 | Olfr1310 | Lhx3 | Nrl | Ccbp2 | Neurl3 |
| Chrd12 | Cd244 | Slc22a29 | Acsm5 | Accn1 | Tchh |
| Igfbp1 | Timm8a2 | Dspp | Dnaic1 | Kcnk18 | Odf4 |
| Tph1 | Crtam | Nlrp6 | Hes2 | Fbxw16 | Tlr9 |
| Tlx3 | Plcxd3 | Tnfaip8l3 | Pou2f3 | Fer1l4 | Inpp5j |
| Slco2b1 | Cyp8b1 | Olfr1300-ps1 | Tgm5 | Lax1 | Lrrn4 |
| Wt1 | Kif17 | G6pc | Kcnh7 | Htr7 | Emr4 |
| Lrrc66 | Tm4sf5 | Trim31 | Lrrtm1 | Ccdc33 | Xpnpep2 |
| Ybx2 | Slc36a2 | Crxos1 | Dpysl5 | Kcnj11 | Kcnk4 |
| Tdrd6 | Acvr1c | Nlrp3 | E330023G01 | Ikzf3 | Vmn2r28 |
| Ermn | Dlgap2 | Otx1 | Bcl3 | Zfp804a | Slc39a12 |
| Naip1 | Ccnb3 | Rd3 | Lce1g | Igj | Hlf |
| Cdh22 | Scn4a | Nppc | Clstn3 | Gja6 | Dydc2 |
| Serpina3h | ligp1 | Vipr1 | Spem1 | Lhfpl3 | Kbtbd5 |
| Spag16 | Ccr5 | Nlrp2 | Il1rapl1 | Tmem132d | Cp |
| Pcnxl2 | Masp2 | Slc22a2 | Cryba1 | Krt73 | Ccl7 |
| Prodh2 | Ctrl | Plg | Dub1 | Pnoc | Zc3h12a |
| Dnase1l3 | Ncam2 | Brs3 | H28 | Dll3 | Fzd10 |
| Nr5a2 | Hrc | Sv2b | Cgn | Nkx2-2as | Zmynd10 |
| Hcrtr2 | Dnahc2 | Gck | Tdrd9 | Rny3 | Fscn3 |
| Eomes | Gria1 | Creg2 | Ppp1r3a | Ehf | Scn10a |
| C3 | Sucnr1 | Kcnn3 | Glra4 | Best2 | Hhatl |
| Dsc1 | Eps8l3 | Ttc9b | Prokr2 | Dmrt1 | Atp2c2 |
| Fn3k | Vwc2l | Serpina3g | Cidec | Tacr2 | Myo5c |
| Olfr536 | Padi6 | AU022754 | Mettl7b | Sall4 | Zswim5 |
| Rasd2 | Cps1 | Rny1 | Hc | Cd86 | Robo3 |
| B4galnt4 | Crym | Cacna1f | Nhlrc4 | Ifi203 | Ccdc147 |
| Cpne4 | Nfkbiz | Myh6 | H60b | Fabp12 | Kcnk10 |
| Clca4 | Pak7 | Ugt2b34 | Rimklb | Vmn2r24 | Mmp25 |
| Tcp11 | Fstl5 | Ccdc63 | BC030870 | Rbp3 | Acap1 |
| Cacna1e | Glb1l3 | Slamf8 | Ttc34 | Gys2 | Ccdc67 |
| Piwil1 | Slc17a4 | Hoxa10 | C8g | Lrat | Fam24a |
| Catsperg2 | Vmn2r2 | Atp7b | Rab44 | Pgr15l | Papln |
| Ccl2 | Tmem229a | Gabbr2 | Atp1a4 | Pcdha2 | Kng1 |
| Arhgap40 | Zfl2 | Psapl1 | Clvs2 | C87414 | Fxyd2 |
| | | | | | Apol10b |

EXAMPLES

Example 1

In this Example, an exciting and novel role of Act1 is reported, which functions as a direct RNA binding protein to stabilize otherwise unstable mRNAs of pro-inflammatory genes in response to IL-17 stimulation, including CXCL1, TNF and GM-CSF. Mutagenesis studies indicate that Act1 directly binds to a stem-loop structure in the 3' UTR of CXCL1, and the SEFIR domain in Act1 is necessary and sufficient for the RNA binding activity. In support of this, exemplary RNA aptamers containing the stem-loop structure (referred as SBE), inhibited Act1's binding to the target mRNAs and attenuated IL-17-mediated mRNA stabilization. Moreover, while SBE RNA aptamers inhibited IL-17-induced skin inflammation.

While the present invention is not limited to any particular mechanism, and an understanding of the mechanism is not necessary to practice the invention, it is believed that mechanistically, Act1 directly binds to the mRNAs of inflammatory genes to form multiple RNPs (protein-RNA complexes) controlling different steps of mRNA metabolism. Act1 binds to the mRNAs in the nucleus (RNP1) preventing SF2-mdiated mRNA decay by competing off SF2's binding to mRNAs, and Act1 follows the mRNAs to the P-bodies (RNP2) inhibiting Dcp1/2-mediated mRNA decapping by employing TBK1 to phosphorylate Dcp1. Finally, Act1-bound mRNAs are shifted to the polysomes by facilitating HuR's binding to mRNAs (RNP3) for protein translation. Taken together, this Example provides the first example of a receptor-interacting adaptor molecule, Act1, playing a direct role in mRNA metabolism, and elucidates a new mechanism for receptor-mediated selectivity of mRNA stabilization and translation.

Materials and Methods:

Animals: IKKi-deficient mice were a gift from T. Maniatis. TBK1 flox mice were obtained from Millenium Pharmaceuticals, Inc., Mice 6 weeks of age were used for primary kidney cells isolation. LSL-HA-Act1 knock-in mice were bred onto UBC-Cre-ERT2 mice (Ruzankina et al., 2007). The Cleveland Clinic Institutional Animal Care and Use Committee reviewed and approved the animal experiments.

Cell culture and Reagents: Antibodies against Act1, GAPDH and β-actin were from Santa Cruz Biotechnology. Anti-hemagglutinin (HA) was from Sigma; TBK1 antibody, M2, V5, p-JNK, JNK, p-IkBa, p-p65, p65, IKKi, IKKα/β, pERK and pIkB antibodies were purchased from Cell Signaling Technology. p-S315 Dcp1a antibody was a kind gift from Dr. Elisa Izaurralde. Dcp1 antibody was a kind gift from Dr. Jens-Lykke Andersen. TBK1 inhibitor MRT67307 was purchased from Sigma Aldrich. Cell culture of mouse embryonic fibroblasts (MEFs), HeLa Tet-Off cells and primary kidney epithelial cells were isolated as previously described (Herjan et al., 2013). Act1−/− MEFs were reconstituted with either empty vector, flag-tagged mAct1, or flag-tagged deletion mutants of mAct1 by retroviral infection as described before (Liu et al., 2011). Proximity-based ligation assays were performed in Hela cells according to the manufacturer's instructions (Duolink™ Assay, Sigma Aldrich).

Transfection, adenoviral and retroviral infection: All transfections were conducted with Lipofectamine 2000 (Invitrogen) according to the manufacturer's instructions. For Act1 reconstitution into Act1−/− MEFs, cells were infected by retroviral supernatant as described previously (Qian et al., 2007). Briefly, viral supernatant was obtained by transfecting Phoenix cells with 5 µg of retroviral construct derived from pMSCV-IRES-GFP for 48 hours. MEFs were infected with viral supernatant for 24 hours and GFP-positive cells were sorted out to establish stable cell lines for downstream assay. Adenoviral infection: primary kidney epithelial cells were divided into 60-mm dishes and infected by exposing them to media containing $2 \times 10^5$ infectious units/plaque formation units of adenovirus/ml overnight.

Quantitative real-time PCR: Total RNA was isolated with TRIzol reagent (Invitrogen). The cDNA was synthesized with random hexamers (Applied Biosystems) and M-MLV reverse transcriptase (Promega). Real-time PCR was performed using a SYBR Green PCR Master Mix kit (Applied Biosystems). All gene expression results were calculated by the change-in-cycling-threshold ($\Delta$CT) method, where $\Delta$CT=CT of target gene−CT of Actb (encoding β-actin), and are presented as 2-$\Delta$CT. The primers used for qPCR are listed in Table 3.

Constructs: For GFP reporter constructs, full-length cDNAs of hAct1, hDcp1a, hIKKi, hTBK1 and hTIA1 were cloned into pEGFP-N1 vector (Clontech). For RFP reporter constructs, full-length cDNAs of hAct1, hIRAK1, and hDcp1a were cloned into pDsRed-Monomer-Hyg-N1 vector (Clontech). For constructs V5-hDcp1a, FLAG-hDcp1a, FLAG-hDcp2, FLAG-hIRAK1, V5-IL-17RA, HA-hAct1 and HA-hAct1 ΔSEFIR, the cDNAs with the corresponding tag were cloned into pcDNA3.1 vector. Wild-type (FLAG-hAct1) and Act1 deletion mutants (ΔSEFIR1, deletion of amino acid residues 391 to 420; ΔSEFIR, deletion of amino acid residues 391 to 537) were flag-tagged and cloned into pcDNA3.1.

Constructs for in vitro transcription: Fragments containing the 3'UTR sequences of CXCL1 220 (nt 720-940) and the truncated fragments CXCL1 120 (nt 780-900), CXCL1 110 (nt 780-890), CXCL1 90 (nt 790-880), CXCL1 80 (nt 800-880), CXCL1 70 (nt 800-870); SBE WT (CXCL1 47, nt 810-857), SBE mutant B (CXCL1 47, nt 810-857 with altered sequence shown in Table 2), SBE mutant C (CXCL1 47, nt 810-857 with altered sequence shown in Table 2), Stem-loop B (CXCL1, 800-835) and Stem-loop C (CXCL1, 830-856) and as well as 3'UTR sequences of TNF (nt 1361-1507), GM-CSF (nt 513-785) and GPx1 (nt 775-962) were generated by PCR and cloned into pGEM-3ZF(+) vector (Promega) using EcoRI and BamHI sites. The plasmid containing 3'UTR of mouse TNF were kind gift of Dr. Vigo Heissmeyer. All mutations were introduced using QuikChange II Site Directed Mutagenesis Kit (Stratagene) according to the manufacturer's instructions. Primers used for generating all constructs are listed in Table 1.

TABLE 1

Primers used for PCR

| | | | SEQ ID NO: |
|---|---|---|---|
| CXCL1 220 | F: | GGAAGAATTCCTGTGTTTGTATGTCTTG | 3 |
| | R: | GGAAGGATCCCTTTTATTTTTACTTCATTT | 4 |
| CXCL1 120 | F: | GGAAGAATTCGTATGGTCAACACGCACGTGT | 5 |
| | R: | GGAAGGATCCCTCTGTCCCGAGCGAGACG | 6 |
| CXCL1 110 | F: | GGAAGAATTCGTATGGTCAACACGCACGTG | 7 |
| | R: | GGAAGGATCCCTCTGTCCCGAGCGAGACGAG | 8 |
| CXCL1 90 | F: | GGAAGGATCCCTCTGTCCCGAGCGAGACGAG | 9 |
| | R: | GGAAGGATCCCTCTGTCCCGAGCGAGACGAG | 10 |
| CXCL1 80 | F: | GGAAGAATTCTTGACGCTTCCCTTGGAC | 11 |
| | R: | GGAAGGATCCGACCAGGAGAAACAGGGTT | 12 |
| CXCL1 70 | F: | GGAAGGATCCGACCAGGAGAAACAGGGTT | 13 |
| | R: | GGAAGGATCCACAGGGTTAAAGAATGTAAAAGGG | 14 |
| CXCL1 47 | F: | GGAAGAATTCCCTTGGACATTTTGTGTC | 15 |
| | R: | GGAAGGATCCTGTAAAAGGGCATTATGCC | 16 |
| GPX1 | F: | CTGGTATCTGGGCTTGGTGATGG | 17 |
| | R: | CTGGTATCTGGGCTTGGTGATGG | 18 |
| TNF 150 | F: | GGAAGGATCCTGTAAAAGGGCATTATGCC | 19 |
| | R: | GGAAGGATCCGCTTATGTTTAAAACAAAATAT | 20 |
| GM-CSF | F: | GGAAGAATTCGACCGGCCAGATGAGGCTGGCC | 21 |
| | R: | GGAAGGATCCCTTGAATAAATATGGAATATG | 22 |
| hAct1-GFP | F: | GGAAGCTAGCATGCCTCCTCAGCTTCAAG | 23 |
| | R: | GGAAGTCGACTGCAAGGGAACCACCTGAAG | 24 |
| hDcp1a-GFP | F: | GGAAGAATTCATGGAGGCGCTGAGTCGAGC | 25 |
| | R: | GGAAGTCGACTGTAGGTTGTGGTTGTCTTTGTTC | 26 |
| hIKKi-GFP | F: | GGAAGCTAGCATGCAGAGCACAGCCAATTAC | 27 |
| | R: | GGAAGTCGACTGGACATCAGGAGGTGCTGGG | 28 |
| hTBK1-GFP | F: | GGAAGGTACCATGCAGAGCACTTCTAATC | 29 |
| | R: | GGAAGTCGACTGAAGACAGTCAACGTTGCG | 30 |
| hTIA-1-GFP | F: | GGAAGCTAGCATGGAGGACGAGATGCCC | 31 |
| | R: | GGAAGTCGACTGCTGGGTTTCATACCCTGCCAC | 32 |
| hAct1-RFP | F: | GGAAGCTAGCATGCCTCCTCAGCTTCAAG | 33 |
| | R: | GGAAGTCGACTGCAAGGGAACCACCTGAAG | 34 |
| hIRAK1-RFP | F: | GGAAGCTAGCATGGCCGGGGGGCCGGGCCCG | 35 |
| | R: | GGAAGTCGACTGGCTCTGAAATTCATCACTTTC | 36 |
| hDcp1a-RFP | F: | GGAACTCGAGATGGAGGCGCTGAGTCGAGC | 37 |
| | R: | GGAAGTCGACTGTAGGTTGTGGTTGTCTTTGTTC | 38 |
| V5-Dcp1a | F: | GGAAGCTAGCGCCACCATGGATTACAAGGATGACG ATGACAAGATGGAGGCGCTGAGTCGAGC | 39 |
| | R: | GGAAGAATTCTCATAGGTTGTGGTTGTC | 40 |
| FLAG-hDcp1a | F: | GGAAGCTAGCGCCACCATGGATTACAAGGATGACG ATGACAAGATGGAGGCGCTGAGTCGAGC | 41 |
| | R: | GGAAGAATTCTCATAGGTTGTGGTTGTC | 42 |
| FLAG-hDcp2 | F: | GGAAGCTAGCGCCACCATGGATTACAAGGATGACG ATGACAAGATGGAGACCAAACGGGTGGAG | 43 |
| | R: | GGAAGGATCCTCAAAGGTCCAAGATTTTC | 44 |
| FLAG-hIRAK1 | F: | GGAAGCTAGCGCCACCATGGATTACAAGGATGACG ATGACAAGATGGCCGGGGGGCCGGGCCCG | 45 |
| | R: | GGAAGAATTCTCAGCTCTGAAATTCATCACT | 46 |
| HA-hAct1 | F: | GGAAGCTAGCATGCCTCCTCAGCTTCAAG | 47 |
| | R: | GGAAGAATTCTCACAAGGGAACCACCTGAAG | 48 |

TABLE 2

Selected REMSA probes

| | |
|---|---|
| CXCL 220 | CUGUGUUUGUAUGUCUUGAAAAGAAUGUCAGUUAUUU<br>AUUGAAAGUCGUCUUUCAUAUUGUAUGGUCAACACGC<br>ACGUGUUGACGCUUCCCUUGGACAUUUUGUGUCUAGU<br>UGGUAGGGCAUAAUGCCCUUUUACAUUCUUUAACCCU<br>GUUUCUCCUGGUCUCGUCUCGCUCGGGACAGAGACGU<br>UCAAAGGACUGUUACAAAUGAAGUAAAAAUAAAAG<br>(SEQ ID NO: 49) |
| CXCL120 | GUAUGGUCAACACGCACGUGUUGACGCUUCCCUUGGA<br>CAUUUUGUGUCUAGUUGGUAGGGCAUAAUGGCCUUUU<br>ACAUUCUUUAACCCUGUUUCUCCUGGUCUCGUCUCGC<br>GUCGGACAGAG (SEQ ID NO: 50) |
| CXCL110 | GUAUGGUCAACACGCACGUGUUGACGCUUCCCUUGGA<br>CAUUUUGUGUCUAGUUGGUAGGGCAUAAUGGCCUUUU<br>ACAUUCUUUAACCCUGUUUCUCCUGGUCUCGUCUCGC<br>U (SEQ ID NO: 51) |
| CXCL90 | GUAUGGUCAACACGCACGUGUUGACGCUUCCCUUGGA<br>ACUUUUGUGUCUAGUUGGUAGGGCAUAAUGCCCUUUU<br>ACAUUCUUUAACCCUGUUUCUCCUGGUCUCGUCUCGC<br>U (SEQ ID NO: 52) |
| CXCL1 80 | UUGACGCUUCCCUUGGACAUUUUGUGUCUAGUUGGUA<br>GGGCAUAAUGCCCUUUUACAUUCUUUAACCCUGUUUC<br>CUCUGGUC (SEQ ID NO: 53) |
| CXCL1 70 | UUGACGCUUCCCUUGGACAUUUUGUGUCUAGUUGGUA<br>GGGCAUAAUGCCCUUUUACAUUCUUUAACCCUGUUUC<br>UCCUGGUC (SEQ ID NO: 54) |
| CXCL1 47<br>(SBE WU) | CCUUGGACAUUUUGUGUCUAGUUGGUAGGGCAUAAUG<br>CCCUUUUACA (SEQ ID NO: 55) |
| CXCL1 47<br>(SBE muUanU B) | CCUUGGACAUUUUGUGUCUAGUUGGUAGGGCAUAAUG<br>CCCUUUUACA (SEQ ID NO: 56) |
| CXCL1 47<br>(SBE muUanU C) | CCUUGGACAUUUUGUGUCUAGUUGGUAAAACAUAAUG<br>CCCUUUUACA (SEQ ID NO: 57) |
| CXCL1 47<br>(SBE AGU) | CCUUGGACAUUUUGUGUCUAGUUGGUAGGGCAAGUUG<br>CCCUUUUACA (SEQ ID NO: 58) |
| CXCL1 47<br>(SBE GGG-CCC swap) | CCUUGGACAUUUUGUGUCUAGUUGGUACCCCAUAAUG<br>GGGUUUACA (SEQ ID NO: 59) |
| CXCL1<br>(SUem loop B) | UUGACGCUUCCCUUGGACAUUUUGUGUCUAGUUGGU<br>(SEQ ID NO: 60) |
| CXCL1<br>(SUem loop C) | GUUGGUAGGGCAUAAUGCCCUUUUAC (SEQ ID NO: 61) |

In vitro transcription and cap-labeling: REMSA radiolabeled 3' UTR RNA probes were synthesized from BamHI linearized plasmids (see constructs for in vitro transcription) templates with T7 RNA polymerase using 1 mM GTP, 1 mM ATP, 1 mM CTP, 0.005 mM UTP and 25 µCi of 32P-labeled UTP for 3 hours at 37° C. Probes were DNAse I treated for 20 minutes and then phenol:chloroform extracted. The aqueous phase was passed through a Micro Bio-Spin P30 column according to manufacturer's instructions (BioRad). For in vitro decapping probes were synthetized as above, but using un-labeled 1 mM CTP, DNAse treated and purified. Cap-labeling was performed using the vaccinia capping system (NEB) according to the manufacturer's instructions in the presence of [α-32P] GTP.

For RNase footprinting experiments, cold synthetic transcripts were dephosphorylated with SuperSAP (Affymetrix), purified, and resuspended in nuclease-free water. Dephosphorylated transcripts were end-labeled in the presence of [γ32P] ATP (3000 Ci/mmole; Perkin Elmer Easy Tides) and T4 PNK (NEB) at 20 units/pmole RNA. The transcripts were gel purified on 8% acrylamide (19:1)/7M urea gels and eluted in 10 mM Tris HCl, pH 7.5, 1 mM EDTA, pH 8, 300 mM NaAc, pH 5.5 at 4° C. overnight. Purified RNA was stored in 10 mM Tris HCl, pH 7.5 at −20° C.

RNase Footprinting

End-labeled 32P-labeled CXCL1 SBE RNA was heated to 95° C. and slow cooled to room temperature. The RNA (2.5 nM) was incubated in L30 binding buffer (30 mM Tris HCl, pH 8.0, 75 mM KCl, 5 mM MgCl2, 1 mM DTT, 0.04 µg/µL BSA (NEB), 10% glycerol, and 50 ng/µL yeast tRNA) with or without mouse Act1 SEFIR protein (1.5 µM) at 30° C. for 10 min. Reactions were cooled to room temperature over a 2 min period and then placed at 22° C. for 2-5 min. The indicated amounts of RNase T1, A, or V1 (Ambion) were added to the appropriate samples and incubated at 22° C. for 5 min. Enzymatic reactions were quenched with 30 µl Inactivation/Precipitation buffer (Ambion) and purified according to manufacturer's directions. Samples were resuspended in 10 µL of loading buffer (Ambion), heat-denatured at 95° C. for 5 min, and separated in a denaturing 8% (19:1) polyacrylamide/7M urea gel. The dried gels were visualized with a phosphorimager or on film.

Sequencing ladders were prepared by incubating end-labeled 32P-labeled CXCL1 SBE RNA (2.5 nM) in 1× Sequencing Buffer (Ambion) supplemented with 50 ng/µL yeast tRNA. The RNAs were incubated at 50° C. for 5 min, cooled to 22° C. and the indicated amounts of RNase T1 and A added. The samples were incubated, quenched, and purified as described above. Alkali ladders were prepared by incubating end-labeled 32P-labeled PHGPx SECIS RNA (2.5 nM) in 100 mM NaOH, 2 mM EDTA, pH 8.0, and 2 µg/µL yeast tRNA at 37° C. for 3 min, to which 0.2 M Tris HCl, pH 8.0 (final) was added. The samples were frozen on dry ice and combined with an equal volume of loading buffer.

RNA Electrophoretic Mobility Shift Assay (REMSA): Increasing amounts of purified protein and labeled probes (10 fmol, see in vitro transcription) were combined in the binding buffer for 30 minutes. The final REMSA binding buffer concentrations were 140 mM KCl, 10 mM HEPES pH 7.9, 5% glycerol, 1 mM DTT and 0.33 mg/ml tRNA. The reaction was further supplemented with 15 µg salmon sperm DNA to reduce non-specific interactions from the lysate. Complexes were resolved on either 4% or 6% non-denaturing polyacrylamide gels. The gels were dried and the appearance of complexes was visualized by exposure to BioMax MR film. Dissociation constants (Kd) were determined by quantified the protein-bound fractions using ImageJ software and plotted against protein concentration (nM). Kd values were extracted from plots fitted to a hyperbolic function in Graph PAD Prism software (OriginLab).

Surface Plasmon Resonance: Binding affinity assays were conducted on a Biacore 3000. The biotinylated RNA was immobilized on a streptavidin-coated sensor chip. SA sensor chips was activated and blocked according to standard protocols. RNA was diluted to 1 mM in HBS-EP buffer (10 mM HEPES, pH 7.4, 150 mM NaCl, 3 mM EDTA, 0.005% surfactant P20) heated at 80° C. for 10 min, cooled to room temperature to allow annealing of the stem, diluted 500-fold in running buffer. RNA was injected at a flow rate of 10 µL/min 40 resonance units of RNA were captured on the SA chip. To study the RNA/Act1 interactions, the proteins were diluted in running buffer and injected at the concentrations indicated in the sensorgrams. Binding experiments were carried out at 25° C. and a flow rate of 30 µl/min. Any protein that remained bound after a 3-min dissociation phase was removed by injecting 2 M NaCl for 60 s at 20 µl/min, which regenerated the RNA surface completely. Data were analyzed with BIAcore 3000 evaluation software and curves were fitted with the "1:1 binding with drifting baseline" model.

Decapping assays: Dcp1/Dcp2 complex and Act1 protein were purified from HeLa cells (2×106) either co-transfected with 10 ug of FLAG-tagged Dcp1 and FLAG-tagged Dcp2 (kind gift from Dr. Andersen) or with 10 ug of FLAG-tagged Act1 by using anti-FLAG/M2-beads (Sigma), eluted in 50 ul using 3× FLAG peptide (Sigma) and protein concentrations were estimated by comparison to a Act1 SEFIR protein of known concentration. 10 fmol of [32P] cap-labeled RNA substrate was incubated with the purified Dcp1/Dcp2 complex (100 ng of each protein) and increasing amounts of purified Act1 protein (0, 100 and 300 ng) in decapping buffer (10 mM Tris, pH 7.5, 100 mM KOAc, 2 mM MgOAc, 2 mM DTT) supplemented with fresh 0.5 mM MnCl2 for 30 min at 370 C. The reaction was terminated by addition of 1 ul of 0.5M EDTA. Reaction products were separated and identified by TLC on cellulose sheets developed in 450 mM (NH4)2SO4. 7meGMP and 7meGDP (20 µg) were spotted routinely on TLC plates along with reaction samples to serve as markers that could be visualized by UV shadowing.

Intradermal injection: LSL-HA-Act1 knock-in/UBC-Cre-ERT2 mice were injected with tamoxifen (~5 mg/25 g weight) 14 and 7 days prior to Intradermal experiment. The ears of 8-week-old female mice were injected intradermally with 20 ul of PBS alone or with PBS containing 0.5 mg of recombinant mouse IL-17A in the presence or absence of 5 nmol of either SBE WT aptamer or SBE mutant C aptamer (for sequence see Table 2). Mice were injected daily for 6 consecutive days. Six days after injection, skin tissue was collected for RNA and staining analyses. For H&E and DAB (3,3'-diaminobenzidine, BD phamagen) staining, skin tissue was fixed in 10% formalin and then processed into paraffin blocks. Epidermal thickness was quantified by ImageJ software.

Aptamer design: Aptamers containing sequences of SBE WT and SBE mutant C (see Table 2) were ordered form Integrated DNA Technologies. Three first residues form both 5' and 3' end were methylated (2'-O Methyl RNA bases) in order to enhance stability. For detection, aptamers were further modified at 5' end with either 6-FAM or Atto647 fluorescent dyes.

Histological analysis: Tracheas were collected from LSL-Act1-HA KI Cre-ERT2 mice subjected to intranasal administration of fluorescently-labeled SBE RNA aptamers, snap-frozen in OCT medium and cryosectioned at 5 µm. Frozen tissue sections was fixed and permeabilized with 4% paraformaldehyde solution containing 0.2% Triton X-100 for 10 minutes. Sections were incubated with rabbit anti-HA Ab followed by staining with Alexa Fluor 488-conjugated goat anti-mouse Ab (green) and microscopic analysis.

ELISA assay: Supernatants from cell cultures were collected and measured for the level of mouse cytokines CXCL1 and TNFα using Duoset ELISA kits (R&D system) according to manufacturer's instructions.

RNA-binding assays RIP: The ability of Act1 to bind to RNA in vivo was assessed as described previously (Datta et al., 2008). Briefly, 10×106 Act1−/− MEFs reconstituted by retroviral infection with M2-tagged mouse wild-type Act1 (WT) were left untreated or treated with IL-17 (50 ng/ml) for 1 hour. Cells were trypsinized, washed twice, and resuspended in 10 ml ice-cold PBS. Cells were fixed in 0.1% formaldehyde for 15 min at room temperature, whereupon the cross-linking reaction was stopped with glycine (pH 7; 0.25 M). The cells were then washed twice with ice-cold PBS, resuspended in 2 ml RIPA buffer (50 mM Tris-HCl [pH 7.5], 1% Nonidet P-40, 0.5% sodium deoxycholate, 0.05% SDS, 1 mM EDTA, 150 mM NaCl, and pro-teinase inhibitors), and sonicated. The lysate was centrifuged (15 min, 4 C, 16,000×g), and 1 ml each supernatant was immunoprecipitated overnight at 4° C., using Dynabeads (invitrogen) preincubated with 20 ug anti-M2 or anti-IgG Ab. The beads were washed five times with 1 ml RIPA buffer and resuspended in 150 ul elution buffer (50 mM Tris-Cl [pH 7], 5 mM EDTA, 10 mM DTT, 1% SDS). Cross-linking was reversed by incubation at 70° C. for 45 min, RNA was purified from immunoprecipitates with Trizol (Invitrogen) according to the manufacturer's instructions and treated with RNase-free DNase, the cDNAs were synthesized and 10% (two microliters) of the reverse transcriptase product was subjected to quantitative real-time PCR. Primers used for quantitative real-time PCR are listed in Table 3.

TABLE 3

Primers for real time quantitative PCR.

|  |  |  | SEQ ID NO: |
|---|---|---|---|
| mCXCL1 | F: | CTGGCCACAGGGGCGCCTATC | 62 |
|  | R: | GGACACCTTTTAGCATCTTT | 63 |
| mCSF2 | F: | GGCCTTGGAAGCATGTAGAGG | 64 |
|  | R: | GGAGAACTCGTTAGAGACGACTT | 65 |
| mTNFα | F: | CATCTTCTCAAAATTCGAGTGACAA | 66 |
|  | R: | TGGGAGTAGACAAGGTACAACCC | 67 |
| mGAPDH | F: | GCCTTCCGTGTTCCTACCC | 68 |
|  | R: | TGCCTGCTTCACCACCTTC | 69 |
| mβ-actin | F: | GGTCATCACTATTGGCAACG | 70 |
|  | R: | ACGGATGTCAACGTCACACT | 71 |
| hCXCL1 | F: | AACCGAAGTCATAGCCACAC | 72 |
|  | R: | GTTGGATTTGTCACTGTTCAGC | 73 |
| hCSF2 | F: | CACTGCTGCTGAGATGAATGAAA | 74 |
|  | R: | GTCTGTAGGCAGGTCGGCTC | 75 |
| hTNFα | F: | TCAGCAAGGACAGCAGAG | 76 |
|  | R: | GTATGTGAGAGGAAGAGAACC | 77 |
| hβ-actin | F: | GTCGGTATGGGTCAGAAAG | 78 |
|  | R: | CTCGTTGTAGAAGGTGTGG | 79 |

RIP data analysis: Ct value of each RIP RNA fractions was normalized to the Input RNA fraction Ct value for the same qPCR Assay (AΔt) to account for RNA sample preparation differences. Then the normalized RIP fraction Ct value (ΔCt) was adjusted for the normalized background (anti-IgG) [non-specific (NS) Ab] fraction Ct value (ΔΔCt). The fold enrichment [RIP/non-specific (NS)] was calculated by linear conversion of the ΔΔCt. Below are the formulas used for the calculation: ΔCt [normalized RIP]=Ct [RIP]−(Ct [Input]−Log2 (fraction of the input RNA saved))); ΔΔCt [RIP/NS]= ΔCt [normalized RIP]−ΔCt [normalized NS]; Fold Enrichment=2 (−ΔΔCt [RIP/NS]).

Immunoblot, immunoprecipitation and nuclear fractionation: Cell were harvested and lysed on ice in a lysis buffer containing 0.5% Triton X-100, 20 mM Hepes pH 7.4, 150 mM NaCl, 12.5 mM-glycerophosphate, 1.5 mM MgCl2, 10 mM NaF, 2 mM dithiothreitol, 1 mM sodium orthovanadate, 2 mM EGTA, 20 mM aprotinin, and 1 mM phenylmethylsulfonyl fluoride for 20 minutes, followed by centrifuging at 12,000 rpm for 15 minutes to extract clear lysates. For immunoprecipitation, cell lysates were incubated with 1 µg of antibody and A-sepharose beads at 4 degree overnight. After incubation, the beads were washed four times with lysis buffer and the precipitates were eluted with 2× sample buffer. Elutes and whole cell extracts were resolved on SDS-PAGE followed by immunobloting with antibodies. Nuclear fractionation was performed using NUCLEI EZ PREP kit purchased from Sigma in accordance with the manufacturer's instruction. Nuclear pellets were suspended in 30 µl of nuclear extraction buffer (20 mM HEPES, 400 mM NaCl, 1 mM EDTA, 1 mM EGTA in water, pH 7.9) containing freshly prepared 1 mM DTT and protease inhibitor cocktail. After 1.5 h incubation on ice bath with intermittent vortexing, extracts were centrifuged and supernatant was collected for immunoprecipitation.

Expression and purification of His-IL-17RA SEFIR, His-MBP-mAct1-SEFIR and His-MBP proteins: The cDNA encoding a SEFIR domain-containing fragment of human IL17RA (His-IL-17RA SEFIR, aa residues 351 to 616) was subcloned into a modified pET-28 vector, with a N-terminal 6× His tag and a tobacco etch virus protease (TEV) recognition site (ENLYFQG). The IL17RA SEFIR domain was expressed and purified by double-Nickel-Nitrilotriacetic Acid (Ni-NTA) affinity methods as previously described (Deng et al., 2004). Size exclusion chromatography on a superdex s200 high resolution column was used as a final step for purification. The cDNA encoding a SEFIR domain containing a fragment of mouse Act1 (aa residues 391 to 537) and its deletion mutants of the SEFIR domain, designated SEFIR1 to SEFIR5 (based on the five exons that encode regions of the SEFIR domain: 410 to 439, 440 to 462, 463 to 501, 502 to 526, and 527 to 552) was cloned into a modified pET28b vector that expresses maltose-binding protein (MBP) with an N-terminal 6× His tag and a C-terminal TEV recognition site. Recombinant mAct1-SEFIR or MBP protein was expressed and purified as previously described (Deng et al., 2008). Size exclusion chromatography on a superdex s200 high resolution column was used as a final step for purification.

In vitro kinase assay: Recombinant IKKi and TBK1 (100 nM) was incubated respectively with purified SF2 and Dcp1 (10 nM) in the kinase assay buffer containing 25 mM Tris (pH 7.5), 5 mM β-glycerophosphate, 2 mM DTT, 0.1 mM Na3VO4, 10 mM MgCl2 supplemented with 100 nM ATP and 1 ul [γ-32P]-ATP (PerkinElmer) (10 µCi) at 37° C. for 30 min. The samples were subjected to SDS-PAGE followed by authoradiograph.

mRNA decay assay: Endogenous mRNA half-lives were determined with the use of actinomycin D (5 mg/mL) to inhibit transcription. Pulse-Chase mRNA decay assay in HeLa Tet-off cells were performed as described previously (Datta et al., 2010). Reporter RNA construct for this assay was obtained by cloning CXCL1 220 (720-940) into pTRE2 (Clontech) containing 5'UTR and coding region of CXCL1 as described previously (KCA4; Datta et al., 2010). Total RNA was isolated by TRIzol reagent (Invitrogen) following the manufacturer's instruction, followed by RT-PCR. The values were normalized to the stable β-actin mRNA.

Statistical analyses: Statistical analyses were performed by Mann-Whitney test or by the Student's t test, where appropriate.

Results

IL-17 Induces Distinct Act1-RNPs in the Nucleus and Cytoplasmic Granules

Figure 1:
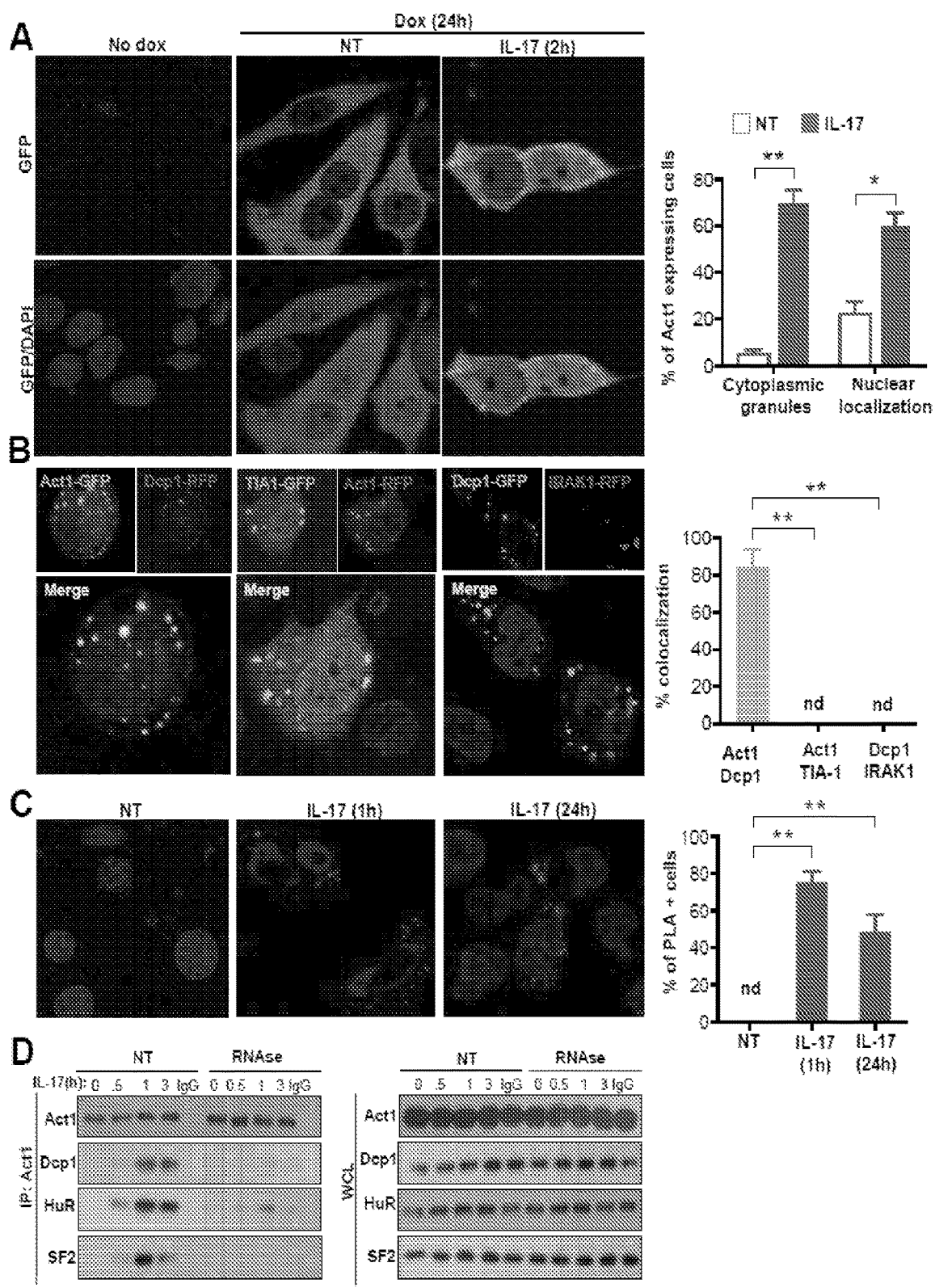
FIG. 1. IL-17 induces distinct Act1-RNPs in the nucleus and cytoplasmic granules. A. Confocal imaging of Act1-GFP in HeLa Tet-On stable cell line induced by doxycycline for 24 hours followed by IL-17 stimulation for 0, 1 or 2 hours. Nuclei stained with DAPI. Bar graph shows the percentages of cells that display Act1 localization in the cytoplasmic granules or nuclear localization with and without IL-17 stimulation. The quantification is based on analysis of over 50 expressing cells with and without IL-17 stimulation followed by two-tailed Student's t-test. Data represent mean±SD; *, $p<0.05$, , $p<0.01$. B. Confocal imaging of HeLa cells co-transfected with GFP- or RPF-tagged expression constructs as indicated. Nuclei stained with DAPI. Bar graph shows the percentages of cells with co-localization of the two expressing proteins (Act1/Dcp1; Act1/TIA1 and Dcp1/IRAK1). The quantification is based on the analysis of over 50 expressing cells, followed by two-tailed Student's t-test. Data represent mean±SD; , $p<0.01$. C. In situ PLA in HeLa cells untreated or treated with IL-17 (50 ng/ml) for 1 hour. Anti-Act1 and Anti-Dcp1 were used as primary mouse antibodies followed by PLA probes. The white/light gray dots indicate the interaction of endogenous Act1 and Dcp1. Nuclei stained with DAPI. Bar graph shows the percentages of PLA positive cells with and without IL-17 stimulation. The quantification is based on the analysis of 50 cells with and without IL-17 stimulation, followed by two-tailed Student's t-test. Data represent mean±SD; , $p<0.01$. D. Lysates from HeLa cells stimulated with IL-17 (50 ng/ml) for the indicated time points, either left untreated or treated with RNase A, were immunoprecipitated (IP) using anti-Act1 followed by Western blot analysis with the indicated antibodies. All above data are representative of at least two independent experiments. E. Confocal imaging of HeLa cells co-transfected with GFP- and RPF-tagged expression constructs as indicated. Nuclei stained with DAPI. Bar graph shows the percentages of cells with co-localization of the two expressing proteins (Act1/Dcp1; Dcp1/HuR and Dcp1/SF2). The quantification is based on the analysis of over 50 expressing cells, followed by two-tailed Student's t-test. Data represent mean±SD; , $p<0.01$. F. In situ PLA assay in HeLa cells transfected with the indicated expression constructs. Primary mouse antibodies against Flag-tag and rabbit antibodies against HA-tag were used. The white/light gray dots indicate the interaction of the two proteins including Dcp1-Flag/Act1-HA, IL-17-RA-Flag/Act1-HA, HuR-Flag/Act1-HA and SF2-Flag/Act1-HA. The co-transfection of IRAK1-Flag and Act1-HA was used as a negative control for PLA assay. Nuclei stained with DAPI. The expression levels of the transfected constructs were also analyzed by western analyses shown below the imaging data. G. Bar graph shows the percentages of PLA positive cells shown in F. The quantification is based on the analysis of 50 cells, followed by two-tailed Student's t-test. Data represent mean±SD; **, $p<0.01$. H. Bar graph shows the percentages of cells with co-localization of Dcp1 with full-length Act1 or Act1 deletion mutants. The quantification is based on the analysis of over 50 expressing cells, followed by two-tailed Student's t-test. Data represent mean±SD; *, $p<0.05$, **, $p<0.01$. I. Act1−/− MEFs reconstituted by retroviral infection with either FLAG-tagged mouse wild-type Act1 (WT) or SEFIR1 deletion mutant were treated with IL-17 (50 ng/ml) for the indicated times. The cell lysates were immunoprecipitated (IP) with anti-FLAG followed by Western blot analysis using antibodies as indicated. Data are representative of two independent experiments.
Figure 1:
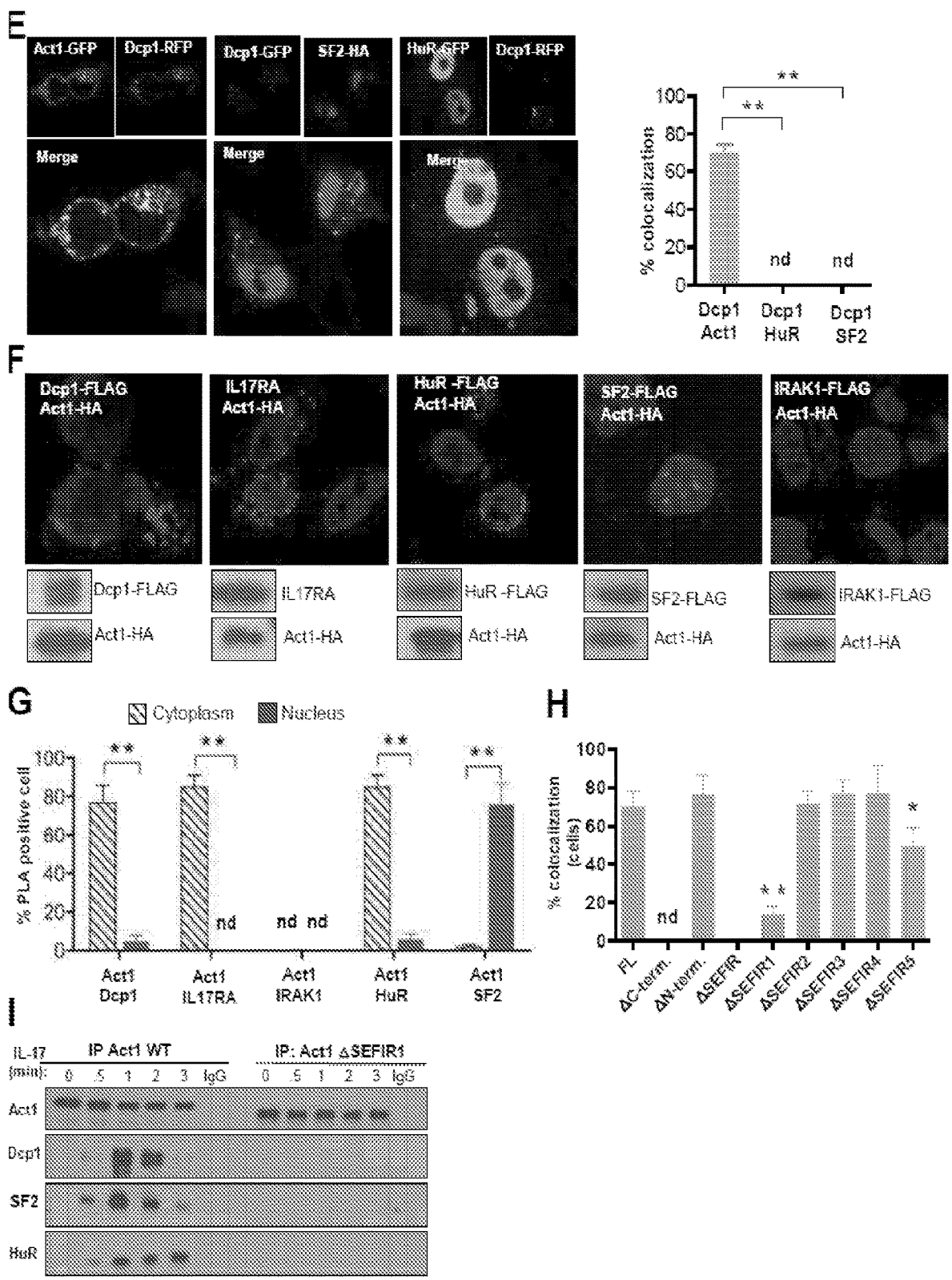

Messenger RNAs that are not engaged in translation can aggregate into cytoplasmic mRNP granules referred to as P-bodies and stress granules (Anderson et al., 2015; Erickson and Lykke-Andersen, 2011). IL-17 stimulation induced the assembly of Act1, the key adaptor of IL-17R, into microscopically visible cytoplasmic granules and nuclear localization [FIG. 1A and (Velichko et al., 2016)]. Act1 was co-localized with Dcp1 decapping enzyme, a component of P-bodies (FIG. 1B); but not with TIA1, a marker for stress granules (FIG. 1B). As a negative control, an unrelated signaling molecule IRAK1, interleukin-1-associated kinase 1, was also co-expressed with Dcp1, which failed to co-localize with Dcp1 decapping enzyme. A strong signal was detected for the interaction between Act1-Dcp1 by in situ Proximity Ligation Assay (PLA, which detects direct protein-protein interaction) in response to IL-17 stimulation, indicating the close proximity of Act1 with Dcp1 (FIG. 1C). We further validated the Act1-Dcp1 interaction by co-immunoprecipitation in response to IL-17 stimulation (FIG. 1D). The fact that RNase pretreatment of the lysates abolished the detection of Act1-Dcp1 interaction suggests that the Act1-Dcp1 interaction is RNA-dependent (FIG. 1D). These results implicate the possible role of IL-17-Act1 axis in mRNA metabolism in the P-bodies.

We examined whether SF2 and HuR are in the Act1-Dcp1 cytoplasmic granules. Interestingly, we found that SF2 and HuR were neither co-localized, nor co-immunoprecipitated with Dcp1 (FIG. 1E). On the other hand, Act1-SF2 and Act1-HuR interaction were indeed detected by PLA in the nucleus and cytoplasmic granules, respectively (FIG. 1F-G). These results indicate that Act1's interaction Dcp1 in the P-bodies is likely independent from the Act1-SF2 and Act1-HuR complexes. Importantly, similar to the Act1-Dcp1 interaction, RNase pretreatment of the lysates abolished the detection of Act1-SF2 and Act1-HuR interaction, suggesting that the Act1's interaction with SF2 and HuR were also RNA-dependent (FIG. 1D). Taken together, these results implicate the IL-17-Act1 axis in mRNA metabolism via formation of distinct Act1-containing RNPs, including Act1-SF2 (RNP1), Act1-Dcp1 (RNP2) and Act1-HuR (RNP3).

SEFIR Domain of Act1 is Required for the Formation of Act1-RNPs

Figure 2:
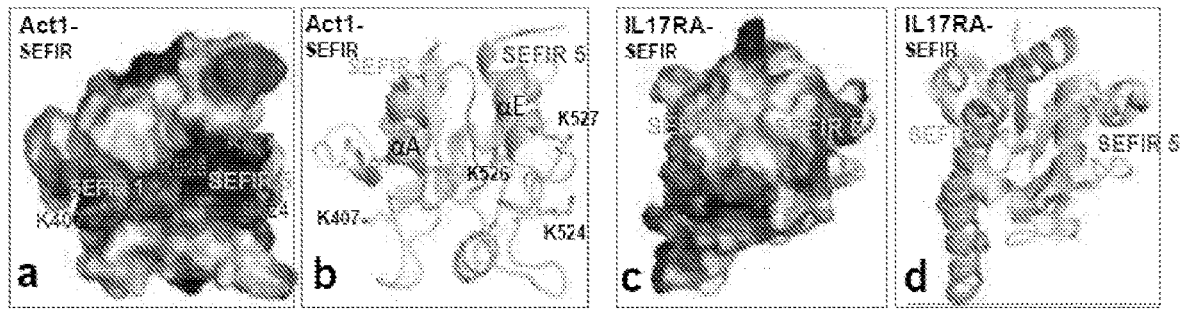
FIG. 2. Act1 directly binds to the CXCL1 3'UTR through the SEFIR domain A. The structure model of Act1-SEFIR was built by SWISS-Model, using the crystal structure of IL-17RA-SEFIR as the template (Zhang et al., 2014) (PDB-code: 4NUX). Surface representation of Act1-SEFIR (a) and IL-17RA-SEFIR (c) are shaded by electrostatic potential. Key secondary structure elements and residues of Act1-SEFIR (b) and IL-17RA-SEFIR (d) are labeled in cartoon representation. B. Binding of purified recombinant His-MBP-Act1 SEFIR (residues 379-538), His-IL-17RA SEFIR (residues 378-536) and His-MBP to the CXCL1 3'UTR (residues 720-940) and Gpx4 3'UTR (residues 775-962) was examined in vitro by REMSA. Radiolabeled RNA probes were incubated with increasing amounts of protein as indicated. Free RNA was separated from RNA-protein complexes by native PAGE. Graph indicates the apparent Kd of CXCL1 3'UTR (720-940, CXCL1 220 as shown in FIG. 3A), which was calculated as the concentration of Act1-SEFIR protein required to achieve 50% binding of the RNA. Data are representative of three independent experiments (mean and s.d.). C. Binding of purified recombinant His-MBP-Act1 SEFIR and ΔSEFIR1, ΔSEFIR2, ΔSEFIR3, ΔSEFIR4 and ΔSEFIR5 to the CXCL1 3'UTR (nt 720-940) as described in (B). D. Table shows the apparent Kds of CXCL1 3'UTR (720-940, CXCL1 220) binding to the indicated proteins in C. Data are representative of three independent experiments (mean and s.d.). E. FLAG-tagged mouse Act1 or SEFIR deletion mutants were transfected into Hela cells with V5-tagged IL-17RA. The cell lysates of the transfected cells were immunoprecipated (IP) using anti-V5 followed by Western blot analyses using the indicated antibodies. Data are representative of two independent experiments. F. Act1−/− MEFs reconstituted by retroviral infection with either FLAG-tagged mouse wild-type Act1 (WT) or SEFIR deletion mutants were treated with IL-17A (50 ng/ml) for the indicated times. The cell lysates were analyzed by Western blotting with the indicated antibodies. G. Act1−/− MEFs reconstituted by retroviral infection with either FLAG-tagged mouse wild-type Act1 (WT) or SEFIR deletion mutants were either left untreated or stimulated with IL-17A (50 ng/ml) for 0, 2, 6 or 24 hours. The mRNA and protein levels were analyzed by RT-PCR (Top) and Elisa (Bottom), respectively. Data are representative of two independent experiments (mean and s.d., *, $p<0.05$, **, $p<0.01$ by Student's t-test). H. Wild-type Act1, SEFIR deletion mutants or empty vector were co-transfected into HeLa Tet-Off cells with pTRE2 (CXCL1 220, nt 720-940, Datta et al., 2010), followed by treatment with doxycycline. RNA samples were prepared from the transfected cells and subjected to RNA blot analysis. Graph indicates the CXCL1 mRNA levels normalized to GAPDH and presented as half-life. Data are representative of two independent experiments. (mean and s.d., *, $p<0.05$ by Student's t-test). I. Binding of purified recombinant His-MBP-Act1 SEFIR and ΔSEFIR1 to the CXCL1 3'UTR (720-940), TNF 3'UTR (1362-1507) and GM-CSF 3'UTR (513-785) was examined by REMSA as in (B). Table indicates the apparent Kds of CXCL1 3'UTR (720-940), TNF 3'UTR (1362-1507) and GM-CSF 3'UTR (513-785), which were calculated as the concentration of His-MBP-Act1 SEFIR and ΔSEFIR1 required to achieve 50% binding of the RNA (quantification see Material and Methods). Data are representative of three independent experiments (mean and s.d.). J. Act1−/− MEFs reconstituted with flag-Act1 were pre-treated with TNF for 1 hour and then treated with IL-17 for 0 and 60 min followed by RNA immunoprecipitation with anti-FLAG and RT-PCR analyses of the indicated mRNAs. The presented are the relative values to levels from IgG immunoprecipitation. K. RNA decay in Act1−/− MEFs reconstituted by retroviral infection with either FLAG-tagged mouse wild-type Act1 (WT) or SEFIR deletion mutants pre-treated with TNF for 1 hour and then treated with Actinomycin D alone (NT) or in the presence of IL-17A (50 ng/ml). The indicated mRNA levels were normalized to GAPDH and presented as decay over time (left) and half-life (right). Data are representative of two independent experiments. (mean and s.d., *, $p<0.05$ by Student's t-test).
Figure 2:
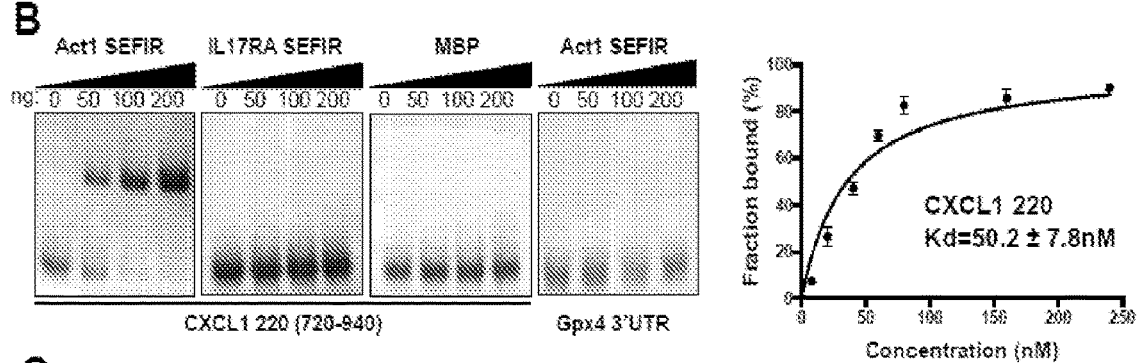
Figure 2:
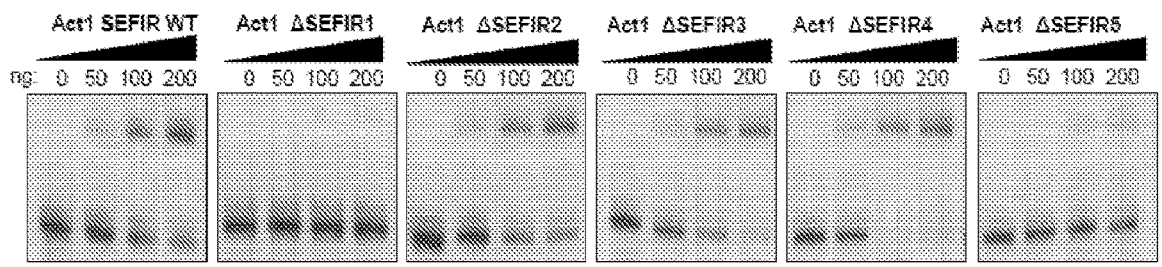
Figure 2:
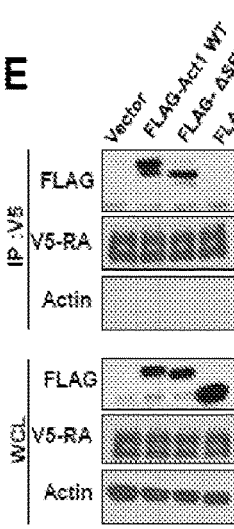
Figure 2:
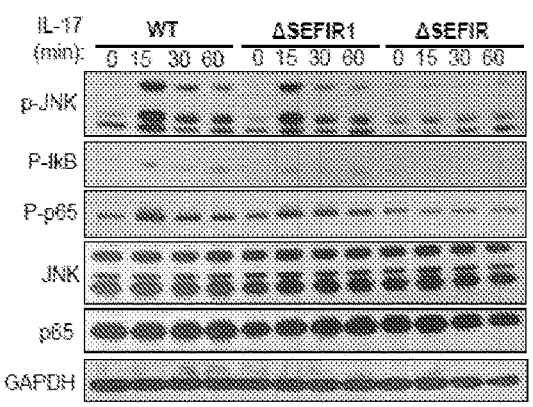
Figure 2:
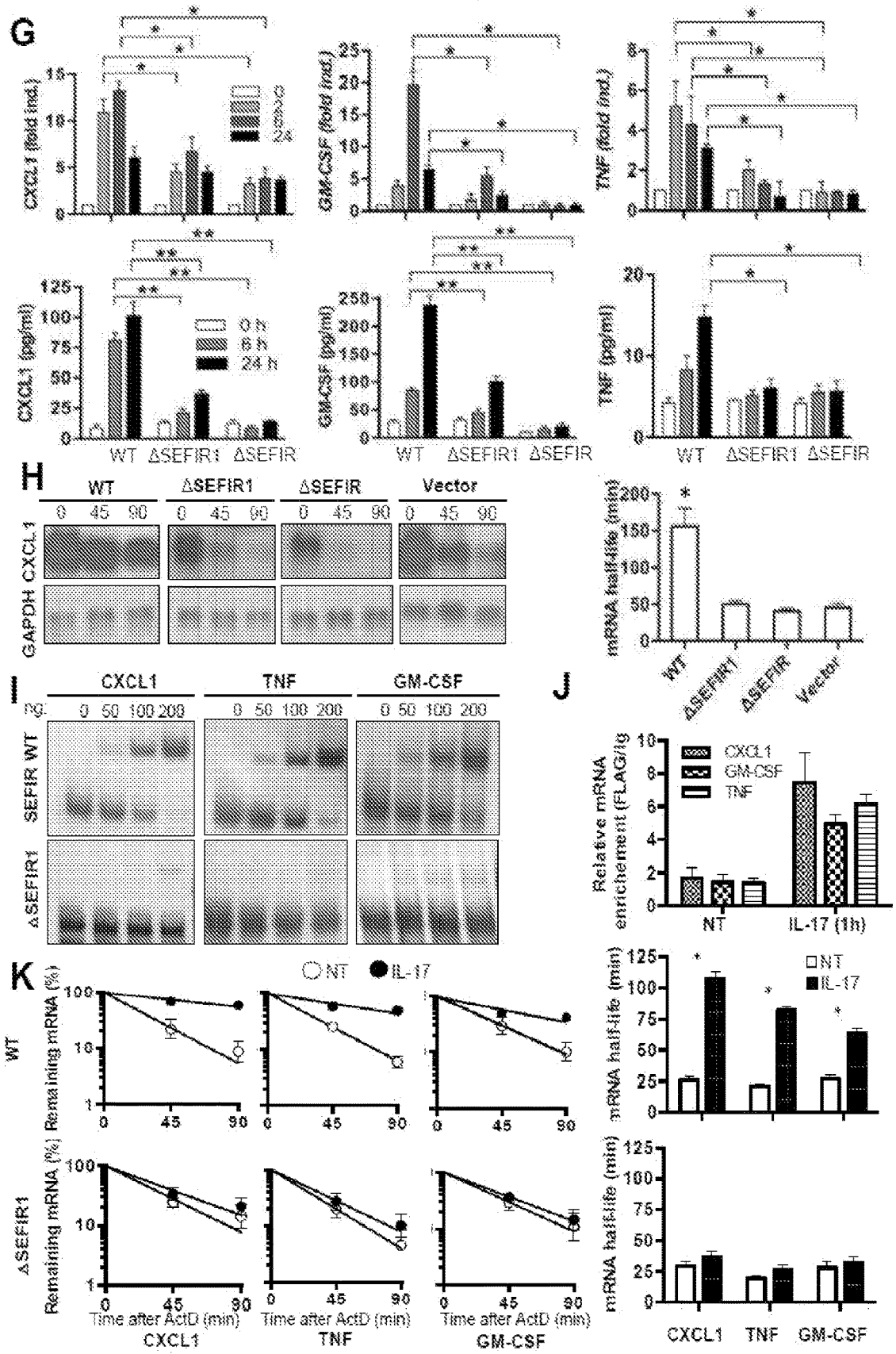

Deletion analysis showed the SEIFR domain of Act1 was necessary and sufficient for Act1 to assemble into granules and co-localize with Dcp1 (FIG. 1H). We then analyzed the internal deletion mutants of the SEFIR domain, designated SEFIR1 to SEFIR5 (based on the five exons that encode regions of the SEFIR domain: 410 to 439, 440 to 462, 463 to 501, 502 to 526, and 527 to 552). Deletion of SEFIR2, 3 or 4 had no impact on Act1's co-localization with Dcp1. Although SEFIR3 (463-501 aa) of Act1 is required for its interaction with IL-17R (Liu et al., 2011), ΔSEFIR3 was still localized to the P-bodies (FIG. 1H). While ΔSEFIR5 showed reduced co-localization with P-bodies, ΔSEFIR1 completely failed to reside in the P-bodies (FIG. 1H and Supple. FIG. 2). Consistently, ΔSEFIR1 also failed to interact with Dcp1 in the co-immunoprecipitation experiment (FIG. 1I). However, both ΔSEFIR1 and ΔSEFIR5 retained their ability to interact with IL-17R (FIG. 2E). We then examined the Act1's SEFIR mutants for their ability to form Act1-SF2 and Act1-HuR RNPs. While deletion of SEFIR1 impaired the interaction with SF2, ΔSEFIR1 also had much reduced binding to HuR (FIG. 1I). These results indicate that the SEFIR domain of Act1 is required for the formation of Act1-RNPs.

Act1 Directly Binds to the CXCL1 3'UTR Through the SEFIR Domain

Since the SEFIR1, and SEFIR5 to a lesser extent, are required for the formation of Act1-RNPs, one question is how these SEFIR subregions are involved in the formation of Act1-RNPs. We modeled the SEFIR domain of Act1 by SWISS-Model, using the crystal structure of IL-17RA-SEFIR as a template. Interestingly, helix aA from SEFIR1 and helix αE from SEFIR5 are located in close proximity in Act1 SEFIR domain forming a positively charged surface (FIG. 2Aa-b). On the other hand, the corresponding helix αA and helix αE from IL-17RA are not located on the same surface and the helix αE is negatively charged (FIG. 2Ac-d). Protein surfaces mediating protein-RNA interactions are often characterized by positive electrostatic potential to complement the negatively charged phosphate groups in the RNA. Thus, it is possible that the SEFIR1+SEFIR5 positively charged surface in Act1 might provide an interaction interface with negatively charged mRNAs. We speculate that Act1 SEFIR may directly bind to IL-17-induced mRNAs, which may then permit Act1-targeted stabilization and translation of the bound mRNAs.

To test such a possibility, we subjected Act1 SEFIR and IL-17RA SEFIR to RNA electrophoretic mobility shift assay (REMSA) on CXCL1 3'UTR, which was shown to be regulated by the IL-17-Act1-axis for stabilization of CXCL1 mRNA (Hartupee et al., 2007). Purified recombinant Act1 SEFIR (rkvfitysmdtamevvkfvnfllvngfqtaidifedrirgidiikwm erylrdktvmiivaispkykqdvegaesqldedehglhtkyihrmmqie-fisqgsmnfrfipvlfpnakkeh vptwlqnthvyswpknkknillrllree; SEQ ID NO:95) or IL-17RA SEFIR was incubated with a radiolabeled RNA probe corresponding to nt 720-940 of the CXCL1 3' UTR (CXCL1 220), which contains IL-17-sensitive motifs, (Datta et al., 2010). The protein-RNA complexes were then separated on a non-denaturing polyacrylamide gel. We found that Act1 SEFIR, but not IL-17RA SEFIR, bound to the CXCL1 probe with Kd=50.2±7.8 nM (FIG. 2B). The binding of Act1 SEFIR to CXCL1 mRNA was specific since the RNA probe corresponding to the GC-rich 3' UTR of Glutathione Peroxidase 4 (GPx4) remained unbound even at high Act1 SEFIR concentrations. While ΔSEFIR2, ΔSEFIR3 and ΔSEFIR4 retained the ability to bind RNA, ΔSEFIR1 and ΔSEFIR5 had much reduced binding to RNA (FIG. 2C-D), suggesting that SEFIR1 and SEFIR5 are indeed involved in direct binding of Act1 to the CXCL1 mRNA. Mutation of the positively charged amino acid residues in SEFIR1 (K407A) and SEFIR5 (K524A, K526A, and K527A) substantially reduced the binding of Act1 SEFIR to RNA, which supports the proposed RNA interaction interface of Act1 SEFIR in FIG. 2Ab. The impaired RNA binding of ΔSEFIR1 and ΔSEFIR5 correlated with their inability to enter the P-bodies and form the RNPs (FIG. 1H), which is consistent with the RNA-dependent Act1's interaction with Dcp1, SF2 and HuR shown in FIG. 1D.

Act1 Mediates mRNA Stabilization of CXCL1, GM-CSF and TNF Via Direct Binding to Their 3'UTRs Consistent with the fact that ΔSEFIR1 still retained its interaction with the IL-17R (FIG. 2E), ΔSEFIR1 was able to mediate IL-17-induced NFkB and JNK activation as wild-type Act1 (FIG. 2F). However, IL-17-induced gene expression, including CXCL1, GM-CSF and TNF, was substantially reduced in MEFs transduced with ΔSEFIR1 compared to wild-type Act1, at both the mRNA and protein levels (FIG. 2G). Since Act1 is necessary for IL-17-mediated stabilization of these otherwise unstable mRNAs of pro-inflammatory genes, we examined whether ΔSEFIR1 might be defective in mediating mRNA stabilization. We transfected HeLa cells stably expressing tetracycline trans-activator protein (HeLa Tet-Off) with a reporter construct pTRE2 CXCL1 containing the region encoding CXCL1 and a truncated 3' UTR (nt 720-940, CXCL1 220) that confers instability and IL-17-Act1-induced stabilization (Datta et al., 2010). CXCL1 mRNA was readily detected and decayed rapidly with a half-life of 30-40 min after transcriptional blockade by the addition of doxycycline (Datta et al., 2010). While transfection of wild-type Act1 extended the CXCL1 mRNA half-life to 2-3 h, ΔSEFIR1 and ΔSEFIR1 failed to stabilize CXCL1 mRNA as did the vector control (FIG. 2H). These results indicate that the impaired RNA binding of ΔSEFIR1 to CXCL1 3' UTR correlated with its inability to stabilize CXCL1 mRNA.

Since ΔSEFIR1 also lost the ability to mediate IL-17-induced expression of GM-CSF and TNF, we examined the possible binding of Act1 SEFIR to their 3' UTRs. Act1 SEFIR but not ΔSEFIR1 bound the GM-CSF 3'UTR (nt 716-1010) and TNF 3'UTR (nt 1362-1507) with similar affinity as the CXCL1 3' UTR (FIG. 2I). To assess RNA binding of Act1 in the cells, we immunoprecipitated Act1 from MEFs untreated or treated with IL-17, followed by RT-PCR analysis. Enriched CXCL1, GM-CSF and TNF mRNAs were detected in Act1 immunoprecipitates compared to that from IgG immunoprecipitation control (FIG. 2J), suggesting IL-17-induced Act1-RNA binding in the cells. To examine the functional impact of Act1-RNA binding, we treated Act1-deficient MEFs reconstituted with wild-type Act1 or ΔSEFIR1 with TNF (for 0.5 h) to promote transcription of inflammatory genes, followed by treatment with actinomycin D (to block transcription) along with IL-17 (to induce mRNA stabilization). The CXCL1, GM-CSF and TNF mRNAs were induced to similar levels in Act1-deficient MEFs reconstituted with wild-type Act1 or ΔSEFIR1 after the initial treatment with TNF. However, the CXCL1, GM-CSF and TNF mRNAs decayed more rapidly in Act1-deficient MEFs reconstituted with ΔSEFIR1 than that with wild-type Act1 (FIG. 2K). The fact that ΔSEFIR1 failed to bind the 3' UTRs of CXCL1, GM-CSF and TNF (FIG. 2I) helps to explain the loss of IL-17-mediated stabilization of those mRNAs (FIG. 2K), implicating the critical role of Act1-RNA binding in mRNA stabilization.

Act1 SEFIR Binds to a Stem-Loop Structure in CXCL1 3'UTR

Figure 3:
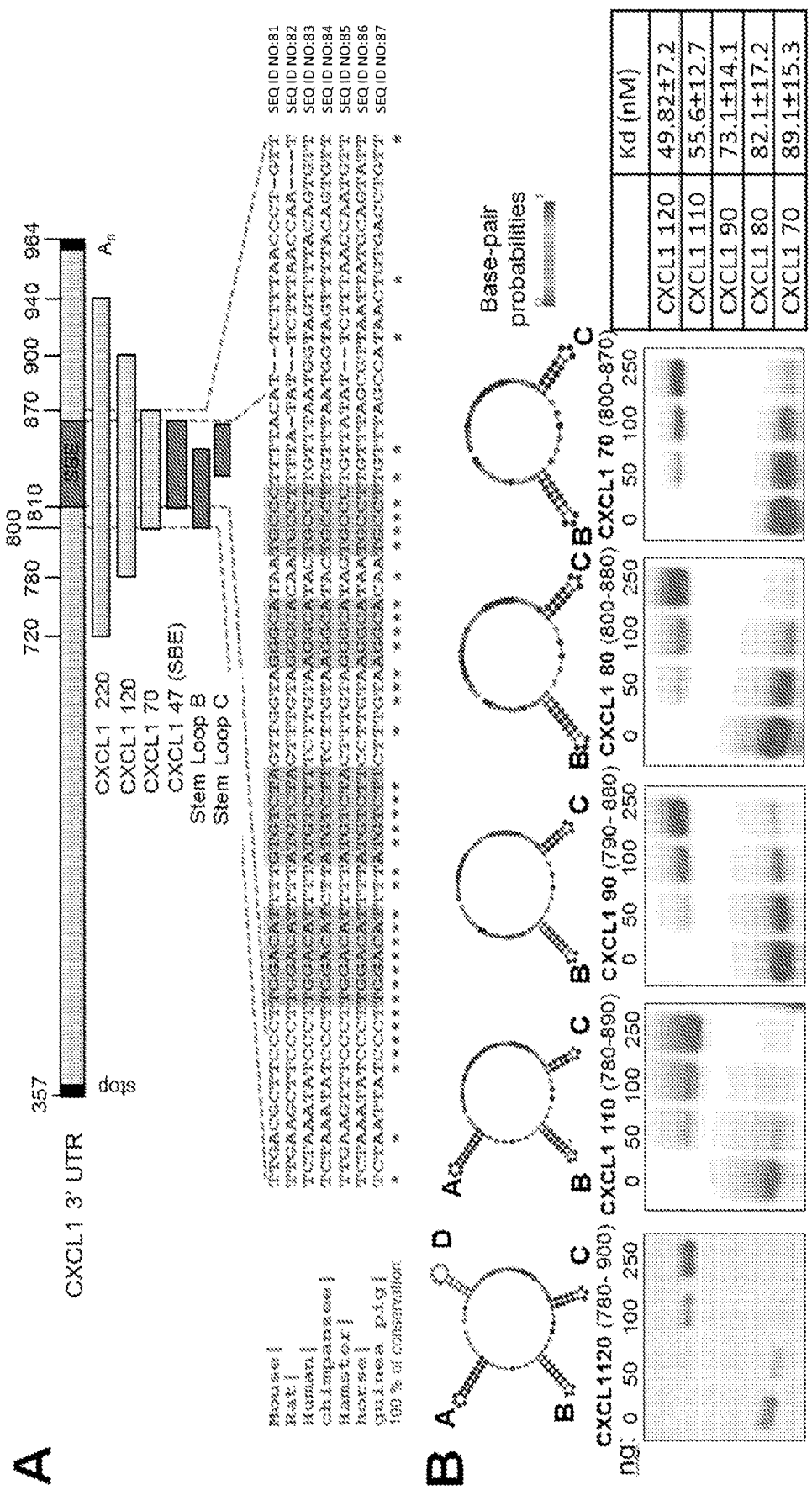
FIG. 3. Act1 SEFIR binds to a stem-loop structure in CXCL1 3'UTR. A. Schematic representation of the mouse CXCL1 3'UTR together with an alignment of the region containing conserved stem-loops in the CXCL1 3'UTRs from indicated species. This alignment includes mouse (SEQ ID NO:81), rat (SEQ ID NO:82), human (SEQ ID NO:83), chimpanzee (SEQ ID NO:84), hamster (SEQ ID NO:85), horse (SEQ ID NO:86) and guinea pig (SEQ ID NO:87). The nucleotides forming conserved stem-loops are indicated with shaded boxes. Mouse CXCL1 sequence is numbered with respect to first nucleotide of the UTR. B. REMSA was performed to examine the binding of purified recombinant His-MBP-Act1 SEFIR to the serial deletion mutants from both ends of CXCL1 220 (720-940) (as indicated in A). Table shows the apparent Kds of the serial deletion mutants CXCL1 120 (780-900), CXCL1 110 (780-890), CXCL1 90 (790-880), CXCL1 80 (800-880), CXCL1 70 (800-870), which were calculated as the concentration of His-MBP-Act1 SEFIR required to achieve 50% binding of the RNA (quantification see Material and Methods). Data are representative of three independent experiments (mean and s.d.). C. Binding of purified recombinant His-MBP-Act1 SEFIR to SEFIR Binding Element (SBE WT, CXCL1 47 as indicated in A) and stem-loop B and stem-loop C disruption mutants (SBE mutant B and SBE mutant C, Table 2 in the Material and Methods) were examined by REMSA. D. Real-time PCR analysis of CXCL1 and GAPDH mRNA in HeLa Tet-Off cells transfected with pTRE2 (CXCL1 220, nt 720-940, Datta et al., 2010), stem-loop B or stem-loop C disruption mutants (SBE mutant B and SBE mutant C, Table 2), were treated with doxycycline alone or together with IL-17 (50 ng/ml) for 0, 45 or 90 min. CXCL1 mRNA levels were normalized to GAPDH and presented as half-life. Data are representative of 2 independent experiments (mean and s.d., *, $p<0.05$ by Student's t-test). E. The 5' end-labeled CXCL1 SBE was incubated in the absence or presence of Act1. The reactions were then partially digested with RNase T1, A, or V1 as indicated. The products were analyzed by denaturing gel electrophoresis. The sequencing (G and C+U) and alkali ladders are shown in the left lanes. The numbers to the left of the gel indicate the positions of nucleotides using the numbering in (F). The bands above C46 are resulted from the remaining sequence in plasmid template after restriction enzyme cutting. The different regions of the SBE are indicated. The gel shown is a representative example from 3 independent experiments. The boxes indicate protected nucleotides in the SBE that were consistently observed. F. The structure of the SEFIR binding element from the mouse CXCL1 mRNA is shown (SEQ ID NO:80). Stars indicate nucleotides that are protected from cleavage by RNase A and V1. G. Binding of purified recombinant His-MBP-Act1 SEFIR to the Stem-loop C and mutants were examined by REMSA.
Figure 3:
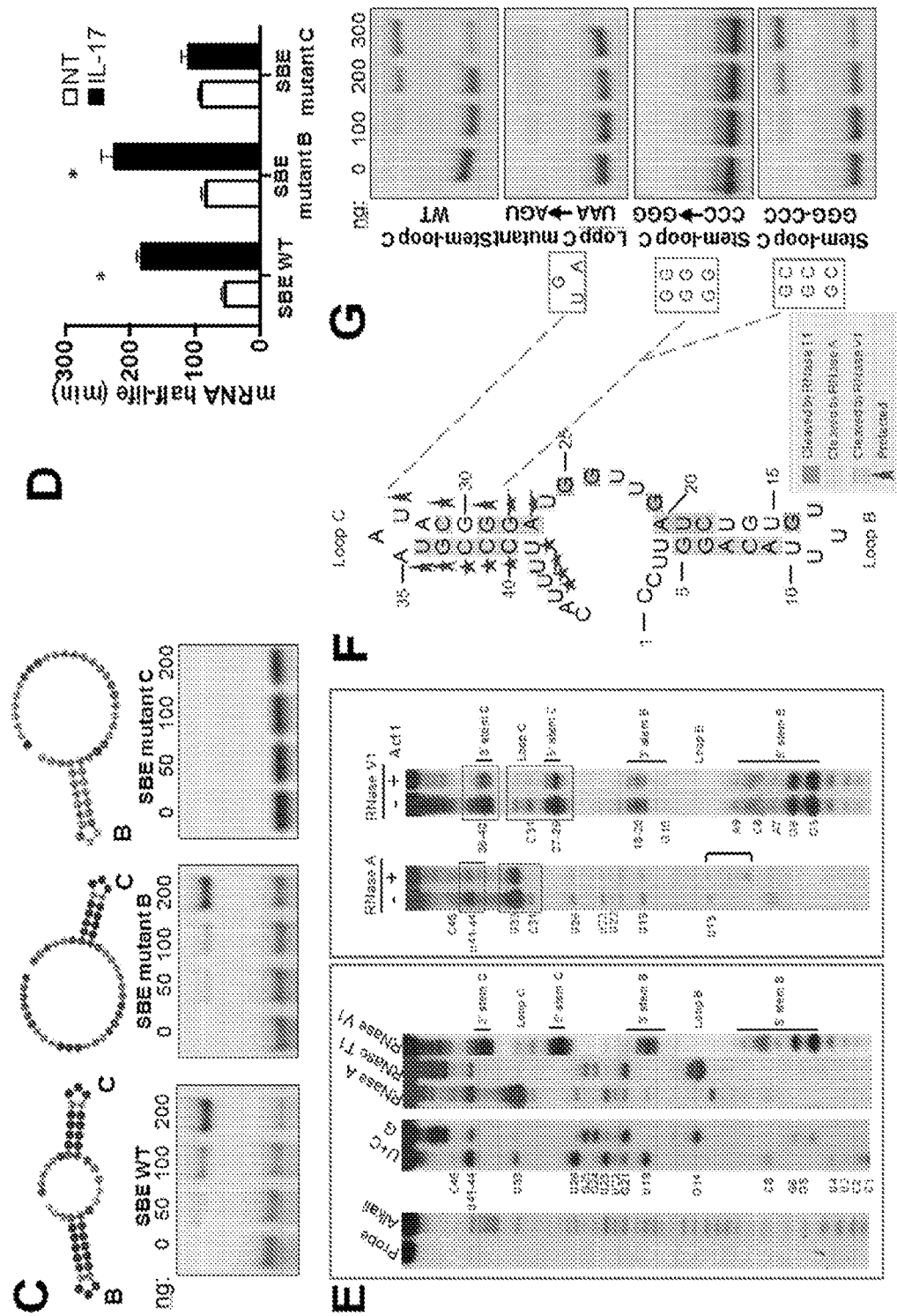

We then aimed to further define the sequences on CXCL1 3' UTR that are recognized and bound by Act1 SEFIR. Act1 SEFIR bound nt 720-940 (CXCL1 220, FIG. 2A) and nt 780-900 (CXCL1 120) of CXCL1 3' UTR with similar affinity (3A-B). Secondary structure prediction (RNAfold web server) indicated that nt 780-900 might form a secondary structure with four stem-loops (named as A-D, FIG. 3B). By generating sequential deletions from both ends, we narrowed down the Act1-binding region to nt 800-870 (CXCL1 70, FIG. 3A-B), which contains an evolutionally conserved region (nt 810-857, CXCL1 47) retaining stem-loop B and C (FIG. 3A). Interestingly, Act1 SEFIR was indeed able to bind to this conserved 47 nt sequence (nt 810-857, CXCL1 47), which was then designated as SEFIR binding element (SBE) (FIGS. 3A and 3C). The binding of Act1 with SBE was confirmed by Surface Plasmon Resonance which revealed a Kd of 59.5 nM.

We then examined the relative importance of stem-loop B and stem-loop C in SBE's binding to Act1 SEFIR. While the disruption of stem-loop B had no impact on Act1 SEFIR's binding, impairment of stem-loop C completely prevented the binding of Act1 SEFIR (FIG. 3C). To test the functional importance of stem-loop C, we disrupted stem-loop B and C respectively in the 3'UTR of CXCL1 of the reporter construct pTRE2 CXCL1 containing the region encoding CXCL1 and a truncated 3' UTR (nt 720-940, CXCL1 220) that confers instability and IL-17-Act1-induced stabilization (Datta et al., 2010). In HeLa Tet-Off cells transfected with pTRE2 CXCL1 or stem-loop B mutant, IL-17 stimulation was able to attenuate CXCL1 mRNA decay after transcriptional blockade by the addition of doxycycline (FIG. 3D). However, IL-17 stimulation failed to attenuate CXCL1 mRNA decay in HeLa Tet-Off cells transfected with stem-loop C mutant (FIG. 3D). Taken together, our structure-function data implicate that Act1 SEFIR's binding to stem-loop C in the 3' UTR of CXCL1 is required for IL-17-induced CXCL1 mRNA stabilization.

In order to directly map the Act1-SEFIR binding site, we performed enzymatic RNA footprinting on the Act1 SEFIR-SBE complex. Nucleotides involved in the Act1-SBE interaction were identified through partial digestion of the SBE RNA, which was performed in the absence or presence of Act1-SEFIR. The native RNA and RNA:protein complexes were then partially digested with different ribonucleases and analyzed by electrophoresis. The cleavage results with the native RNA (FIG. 3E, left panel) are consistent with the predicted structure shown in FIG. 3C. RNase A, which cleaves at single-stranded C and U bases, cleaved at U13, U22, U23, U26, U33 and U41-44 (labeled as yellow in FIG. 3F). RNase T1, which cleaves after single-stranded G bases, cleaved G14, G21, G24 and G25 (labeled as purple in FIG. 3F). RNase V1, which cleaves in double-stranded regions, cleaved at multiple positions in stem B and stem C (labeled as blue in FIG. 3F). Several nucleotides (U19, C31, and U33) were cleaved with both single-stranded and double-stranded nucleases, suggesting that these regions may breathe. When the SBE was incubated with Act1-SEFIR, we observed partial protection of specific nucleotides from cleavage by RNase A (U36, U41-44); and RNase V1 (27-29, C31, 36-40) (boxed in FIG. 3E, right panel). Minor protection between nucleotides 19-23 was occasionally observed but this was not consistent between experiments. Interestingly, bases U10-12 became more accessible to RNase A cleavage which suggests that Act1 binding to stem loopC may cause conformational changes in stem loop B (bracket in FIG. 3E).

Taken together, the footprinting results validated that stem-loop C is the contact site for Act1 SEFIR. Disruption of the stem in stem-loop C (replacing CCC to GGG) abolished the binding of Act1 SEFIR to RNA, whereas replacement of the sequence in the stem of stem-loop C did not alter the binding of Act1 SEFIR, indicating that it is the secondary structure rather than the primary sequence that plays a critical role for Act1 SEFIR's recognition (FIG. 3G). However, the replacement of the entire loop TAA of the stem-loop C with AGU (without affecting the formation of the stem-loop) also abolished the SEFIR binding, demonstrating the importance of loop sequence for Act1 SEFIR-RNA binding (FIG. 3G).

Act1-RNA Binding to 3'UTR Inhibits Decapping

Figure 4:
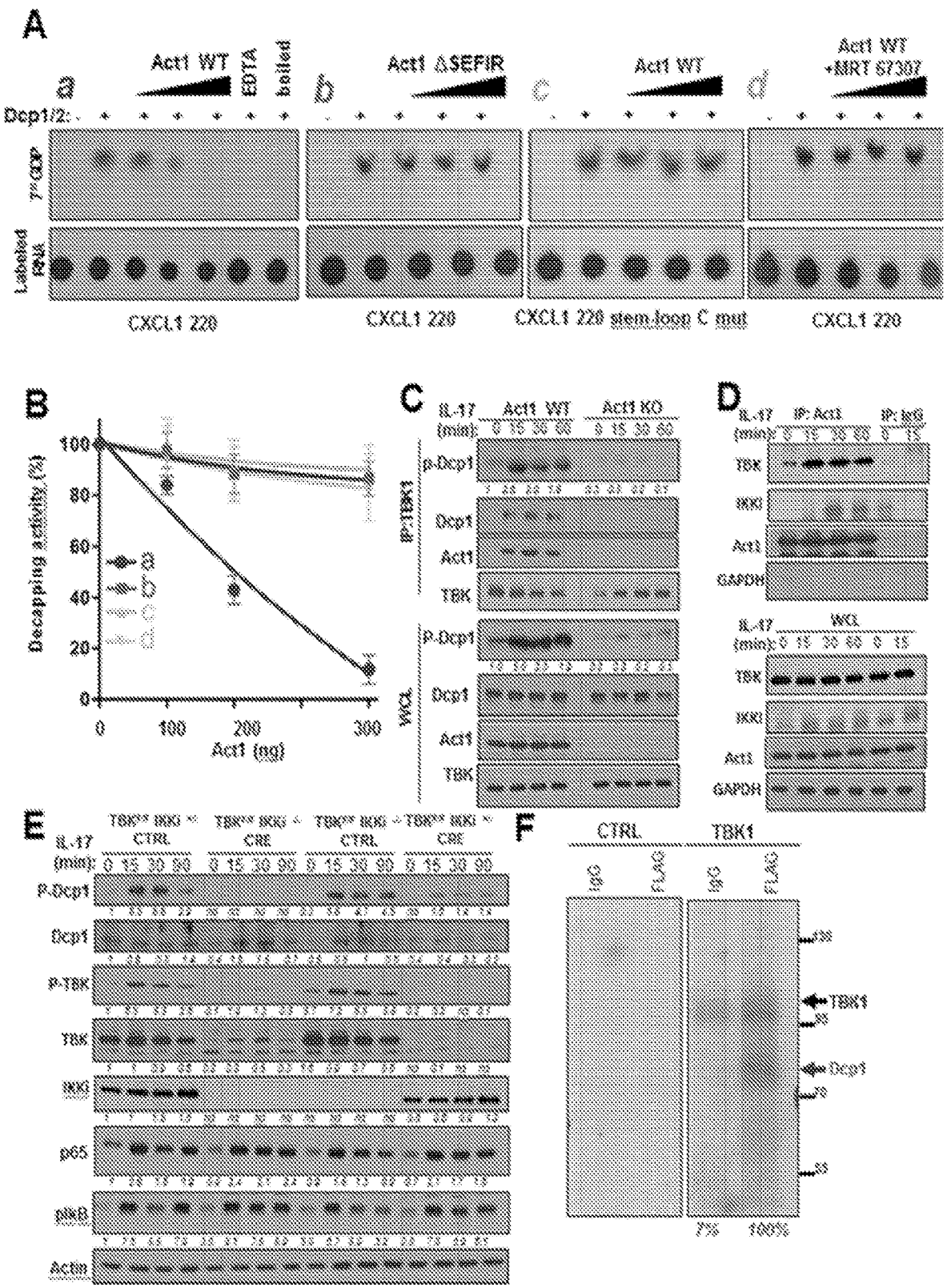
FIG. 4. Act1-RNA binding to 3'UTR inhibits decapping through TBK1-mediated phosphorylation of Dcp1. A. (a-d) Cap (m7GDP) labeled reporter RNAs [CXCL1 220 (a) and mutant without stem-loop C (CXCL1 220-stem-loop C mutant, c)] were subjected to decapping assay using purified Dcp1/Dcp2 with increasing amounts of purified Act1 WT or Act1 ΔSEFIR1 in the presence or absence of TBK1 inhibitor (MRT67307). The purification of proteins were described in Material and Methods. EDTA and boiling were included as negative controls to inactivate Dcp1/Dcp2 enzymatic activity. Radiograms were quantified by densitometry. B. Graph indicates the decapping activity calculated by quantifying the released Cap as a percentage of the amount of Cap catalyzed by purified Dcp1/2. Data are representative of three independent experiments (mean and s.d.). C. Cell lysates from Act1−/−MEFs with and without reconstitution of wild-type Act1 (WT and Act1 KO) were immunoprecipitated (IP) with anti-TBK1 followed by Western blot analysis using antibodies as indicated. Data are representative of two independent experiments. D. Cell lysates from untreated and IL-17-treated HeLa cells were immunoprecipitated (IP) with anti-Act1 followed by Westernblot analysis using antibodies as indicated. Data are representative of two independent experiments. E. Westem blot analysis of lysates from untreated or IL-17A treated mouse kidney epithelial cells (from TBKf/f KKi−/− and TBKf/f IKKi+/− mice) infected with a GFP adenovirus (CTRL) or Cre-GFP adenovirus (Cre). Data are representative of two independent experiments. Western blots were quantified by densitometry using ImageJ. F. In vitro kinase assay of Dcp1 by recombinant TBK1 using Dcp1-immunoprecipitates from HeLa cells transfected with FLAG-tagged Dcp1. G. V5-tagged wild-type Dcp1 (left panel) or S315A mutant (right panel) were transfected into HeLa cells with HA-tagged TBK1 and/or FLAG-tagged Dcp2. The cell lysates were immunoprecipitated (IP) using anti-FLAG followed by Western blot analysis using the indicated antibodies. Data are representative of two independent experiments. Western blots were quantified by densitometry using ImageJ. H. Cell lysates from untreated and IL-17-treated MEFs with or without the presence of TAK1 inhibitor (MRT67307) were immunoprecipitated (IP) with anti-Act1 followed by Western blot analysis using antibodies as indicated. Data are representative of two independent experiments. Western blots were quantified by densitometry using ImageJ. I. The same cells as described in (E) were untreated or stimulated with IL-17A (50 ng/ml) for 0, 2, 6 or 24 hours, as indicated. The mRNA and protein levels were then analyzed by RT-PCR (Top) and Elisa (Bottom), respectively. Data are representative of two independent experiments (mean and s.d., *, $p<0.05$, **, $p<0.01$ by Student's t-test).
Figure 4:
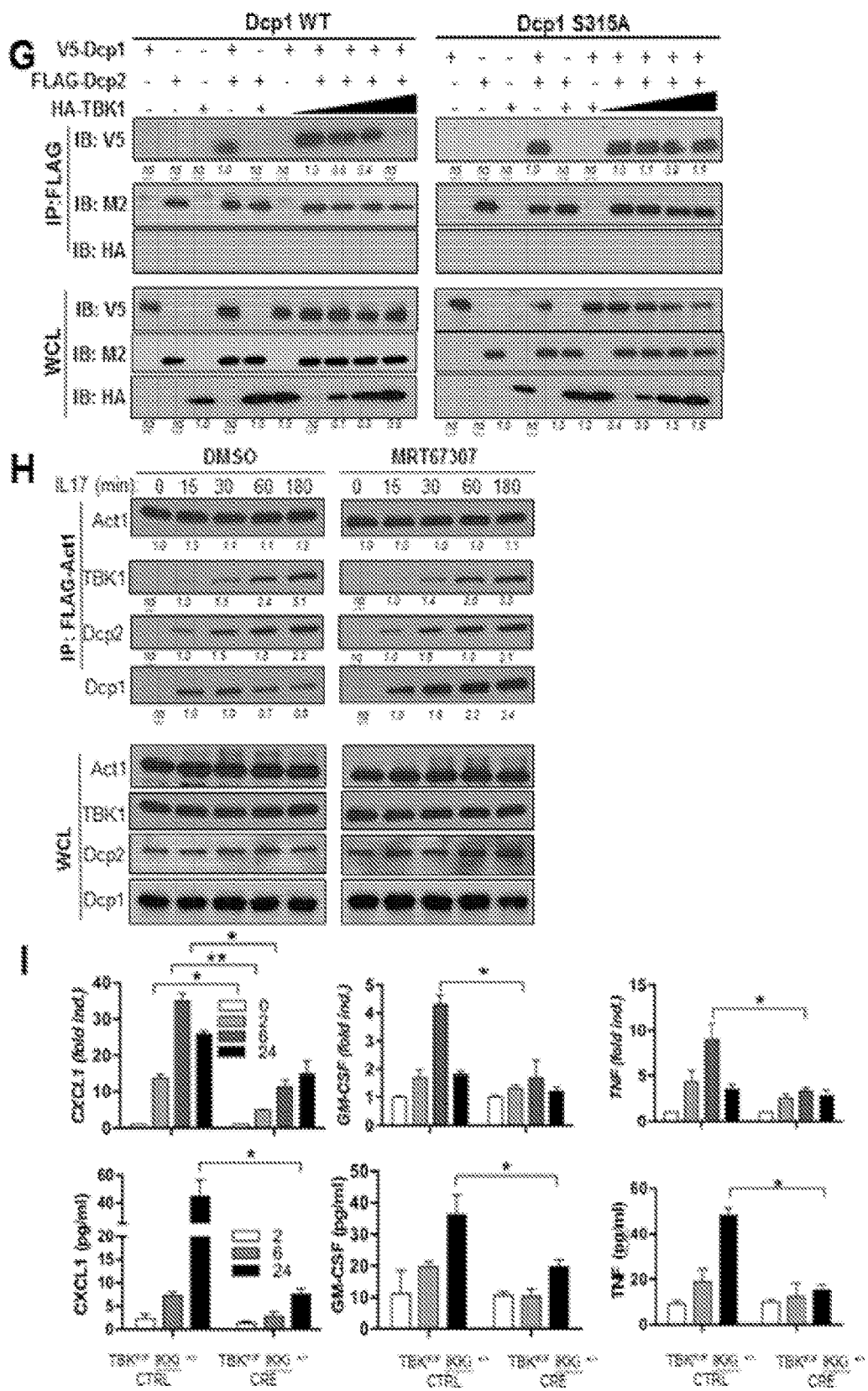

The next question is how Act1-RNA binding in Dcp1-containing P-bodies mediates IL-17-induced stabilization of otherwise unstable mRNAs of pro-inflammatory genes. Notably, the processes of translation and mRNA degradation are actually coupled (Hu et al., 2009; Mukherjee et al., 2012). Initiation of translation usually involves the interaction of translation initiation factors with the 5' terminal m7G cap that is present on most mammalian mRNAs. mRNAs are decapped by the Dcp1/Dcp2 decapping enzymes and then degraded 5' to 3' by the exonuclease Xrn1 (She et al., 2008; Wang et al., 2002). Since both co-immunoprecipitation and in situ PLA showed that Act1 binds to Dcp1, we hypothesized Act1 is specifically bound to its mRNA targets residing in the P-bodies where Act1 attenuates decapping via interaction with Dcp1. To test this hypothesis, we examined whether Act1 binding to Dcp1 will affect decapping activity of Dcp1/Dcp2 complex. Purified Dcp1/Dcp2 and Act1 from transfected HeLa cells were incubated with the capped CXCL1 3'UTR (nt 720-940). There was indeed dose-dependent inhibitory effect of Act1 on decapping efficiency of Dcp1/Dcp2 complex (FIG. 4Aa, 4B). ΔSEFIR1 failed to attenuate decapping, which might be due to its inability to bind CXCL1 3' UTR (FIGS. 4Ab and 4B). To confirm the importance of Act1-RNA binding for the Act1's inhibition of decapping, we disrupted the stem-loop C in cap-labeled fragment of CXCL1 3'UTR (nt 720-940, CXCL1 220) and found that Act1 can no longer block decapping of this mutant reporter transcript (FIGS. 4Ac and 4B).

Act1 Brings TBK1 to Phosphorylate Dcp1 that Dissociates from Dcp2

It was shown that Dcp1 phosphorylation at S315 is required for the inactivation of the decapping activity (Aizer et al., 2013; Rzeczkowski et al., 2011). Using anti-p-S315 antibody, we found that IL-17 treatment indeed induced Dcp1 phosphorylation at S315. IL-17-induced Dcp1 phosphorylation was impaired in Act1-deficient cells (FIG. 4C). Recent studies reported two Act1-interacting kinases: IKKi and TBK1 (Bulek et al., 2011; Qu et al., 2012). Thus, we tested whether these kinases are involved in Act1-mediated regulation of Dcp1. Through immunoprecipitation we confirmed that both IKKi and TBK1 interacted with Act1 upon IL-17 stimulation (FIG. 4D). Interestingly while both IKKi and TBK1 colocalized with Act1, only TBK1 showed colocalization with Dcp1. Consistently, IL-17 stimulation induced the interaction of TBK1 with Dcp1, which was abolished in Act1-deficient cells (FIG. 4C), indicating that IL-17-induced TBK1-Dcp1 interaction is Act1-dependent. While IL-17-induced Dcp1 phosphorylation (but not p-JNK or p-p65) was diminished in TBK1-deficient cells, IKKi deficiency had little effect (FIG. 4E). Recombinant TBK1 was able to phosphorylate Dcp1 in an in vitro kinase assay, implicating that TBK1 might be a direct kinase for Dcp1 (FIG. 4F). Consistently, TBK1 overexpression diminished the interaction between Dcp1 and Dcp2, while TBK1 failed to remove Dcp1 S315A mutant from Dcp2 (FIG. 4G). Interestingly, we observed that IL-17-induced Act1-Dcp1 interaction was enhanced and more sustained in the presence of TBK1 inhibitor, confirming the impact of TBK1 kinase activity on the dissociation of Dcp1 from the Act1-RNP complex (FIG. 4H). Based on these findings, we propose that Act1 brings TBK1 to the mRNA targets in the P-bodies where TBK1 phosphorylates Dcp1, resulting in Dcp1 dissociation from Act1-RNP, inhibition of decapping and stabilization of mRNAs. In support of this, TBK1 inhibitor effectively abolished Act1-mediated inhibition of decapping on cap-labeled fragment of CXCL1 3'UTR (nt 720-940, CXCL1 220) (FIGS. 4Ad and 4B). Western analysis confirmed that TBK1 was indeed co-purified with Act1 used for the decapping assay. Consistently, we found TBK1 deficiency indeed substantially reduced IL-17-induced expression of CXCL1, GM-CSF and TNF at both mRNA and protein levels (FIG. 4I).

Act1 Forms Distinct RNPs with Dcp1/Dcp2, SF2 and HuR

Figure 5:
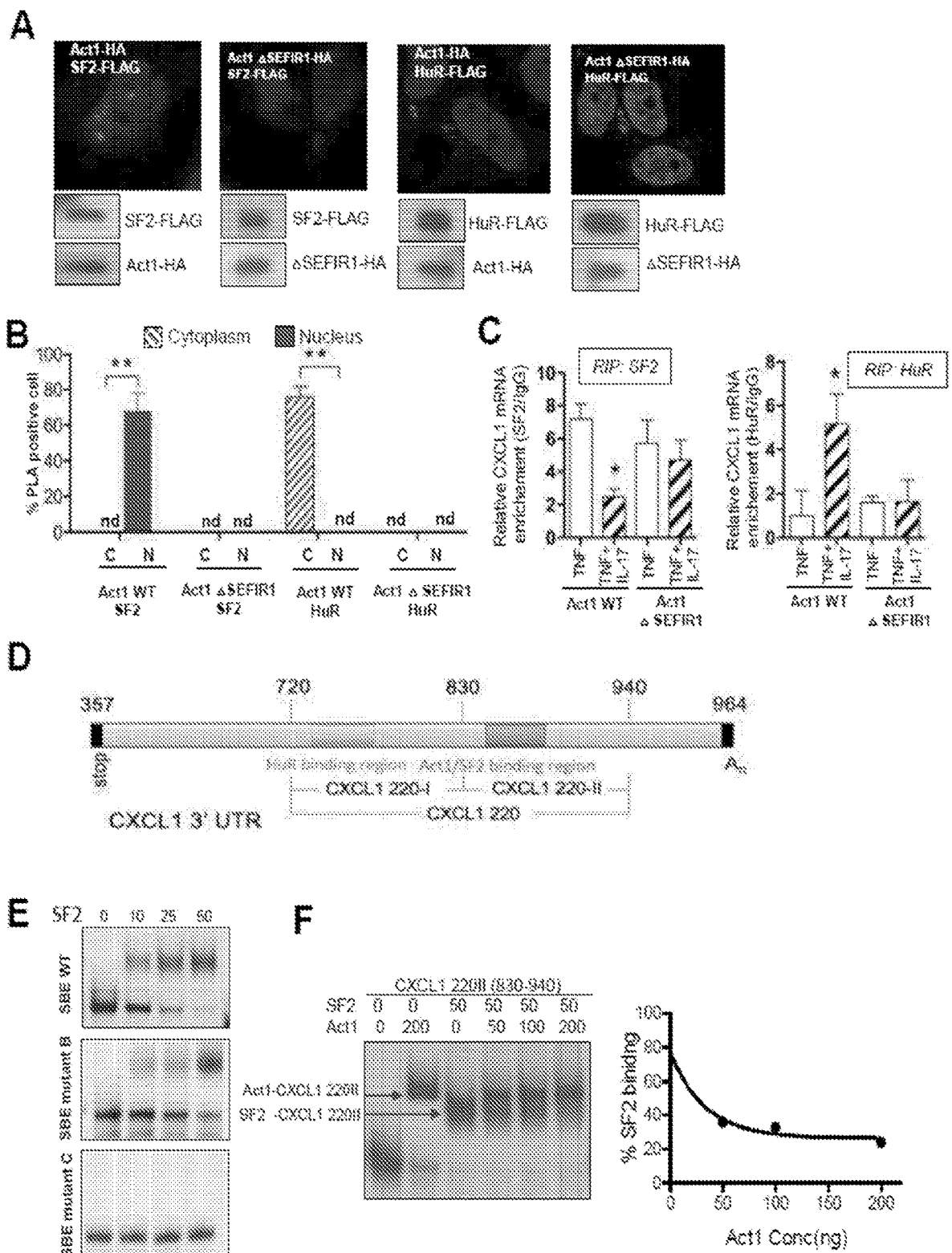
FIG. 5. Act1 forms distinct RNPs with Dcp1/Dcp2, SF2 and HuR. A. Confocal imaging of in situ PLA in HeLa cells transfected with the indicated expression constructs. Primary mouse antibodies against Flag-tag and rabbit antibodies against HA-tag were used. The white/light gray dots indicate the interaction of the two proteins including Act1-HA/SF2-Flag, Act1 ΔSEF-HA/SF1-Flag, Act1-HA/HuR- Flag and Act1-ΔSEF-HA/HuR-Flag. Nuclei stained with DAPI. The expression levels of the transfected constructs were also analyzed by western analyses shown below the imaging data. B. Bar graph shows the percentages of PLA positive cells shown in A. The quantification is based on the analysis of 50 cells, followed by two-tailed Student's t-test. Data represent mean SD; *p<0.05. C. Act1-/- MEFs reconstituted by retroviral infection with either FLAG-tagged mouse wild-type Act1 (WT) or SEFIR1 deletion mutant were pre-treated with TNF for 1 hour and then treated with IL-17 for 0 and 60 min followed by RNA immunoprecipitation with anti-SF2 or anti-HuR, followed by RT-PCR analyses of the indicated mRNAs. The presented are the relative values normalized against IgG control (Material and Methods). D. Schematic representation of the mouse CXCL1 3'UTR. HuR, Act1 and SF2 binding regions are indicated. E. Binding of purified recombinant SF2 to SEFIR Binding Element (SBE WT, CXCL1 47 as indicated in A) and stem-loop B and stem-loop C disruption mutants (SBE mutant B and SBE mutant C, Table 2) were examined by REMSA. F. Act1-SEFIR and SF2 RNA binding competition was performed using probe CXCL1 220 II (containing SF2 and Act1 binding site as indicated in D). Radiolabeled RNA probe was incubated with increasing amounts of Act1-SEFIR with or without co-incubation with purified SF2 as indicated. Free RNA was separated from RNA-protein complexes by native PAGE. Graph indicates the dissociation of SF2-CXCL1 220 II upon incubation with increasing amounts of Act1-SEFIR, which was calculated by quantifying the remaining SF2-CXCL1 220 II complex in the presence of indicated amounts of Act1-SEFIR. Data are representative of three independent experiments (mean and s.d.). G. Cytoplasmic and nuclear fraction lysates from Act1-/- MEFs reconstituted by retroviral infection with either FLAG-tagged mouse wild-type Act1 (WT) or SEFIR1 deletion mutant, stimulated with IL-17 (50 ng/ml) for the indicated times, were immunoprecipitated with anti-FLAG and analyzed by Western blots with the indicated antibodies. The experiments were repeated for two times. H. In vitro kinase assay of purified recombinant IKKi using purified recombinant SF2 as a substrate. I. REMSA was performed to examine the binding of IKKi-phosphorylated SF2 (p-SF2) and non-phosphorylated SF2 (minus IKKi and minus ATP) to SEFIR Binding Element (SBE WT, CXCL1 47 as indicated in FIG. 3A). Graph indicates the apparent Kd of CXCL1 47 (FIG. 3A), which was calculated as the concentration of SF2 protein required to achieve 50% binding of the RNA (Material and Methods). Data are representative of three independent experiments (mean and s.d.). J. Binding of purified recombinant HuR to CXCL1 220-I (containing HuR binding site) and CXCL1 220 II (containing SF2 and Act1 binding site) as indicated in D were examined by REMSA. K. The simultaneous binding of purified recombinant HuR and Act1-SEFIR to CXCL1 3'UTR was examined by REMSA using CXCL1 220 (containing HuR and Act1 binding site as indicated in D) and CXCL1 220 II (containing Act1, but not HuR binding site as indicated in D) as probes. The co-binding Act1-HuR was observed with probe CXCL1-220, but not CXCL-220 II. L. UV-absorbance profile of RNP and polysome complexes separated on a sucrose density gradient into different fractions as indicated. M. Cytoplasmic extracts of Act1-/- MEFs reconstituted by retroviral infection with either FLAG-tagged mouse wild-type Act1 (WT) or SEFIR1 deletion mutant, pre-treated with TNF for 1 hour and then treated with IL-17 for 0 and 90 min, were fractionated through a 10-50% sucrose gradient (as described in L) and analyzed by Western blot analyses with the indicated antibodies. N. CXCL1 and GAPDH mRNAs from translation-active pools and translation-inactive pools from L were analyzed by RT-PCR and normalized to β-actin. Graph shows the ratios of mRNAs from translation-active/ inactive pools. Data are representative of three independent experiments. (mean and s.d., *, p<0.05, **, p<0.01 by Student's t-test). O. Model of Act1-RNP in mRNA stabilization: Act1 directly binds to the mRNAs of inflammatory genes to form multiple RNPs controlling different steps of mRNA metabolism in response to IL-17 stimulation. Upon IL-17 stimulation, Act1 is translocated into the nucleus where Act1 binds to a stem-loop structure in the 3'UTR in the target mRNAs (RNP1). The binding of Act1 competes off SF2 from the mRNAs by bringing IKKi to phosphorylate SF2, preventing SF2-mediated mRNA decay. Act1 then follows the mRNAs to the P-bodies (RNP2) inhibiting Dcp1/2-mediated mRNA decapping by employing TBK1 to phosphorylate Dcp1. Finally, Act1-mRNAs are shifted to the polysomes to facilitate HuR's binding to mRNAs (RNP3) for protein translation.
Figure 5:
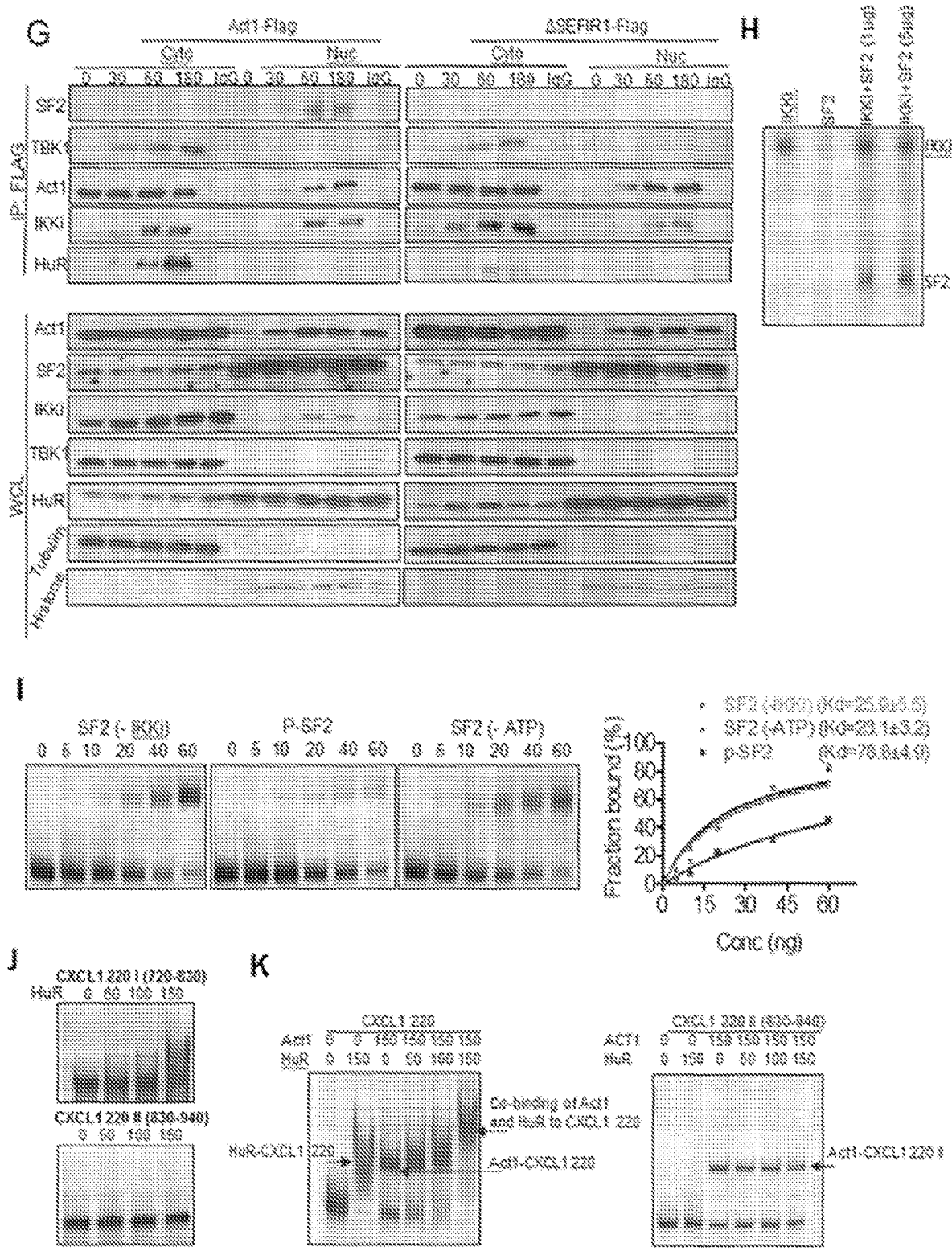
Figure 5:
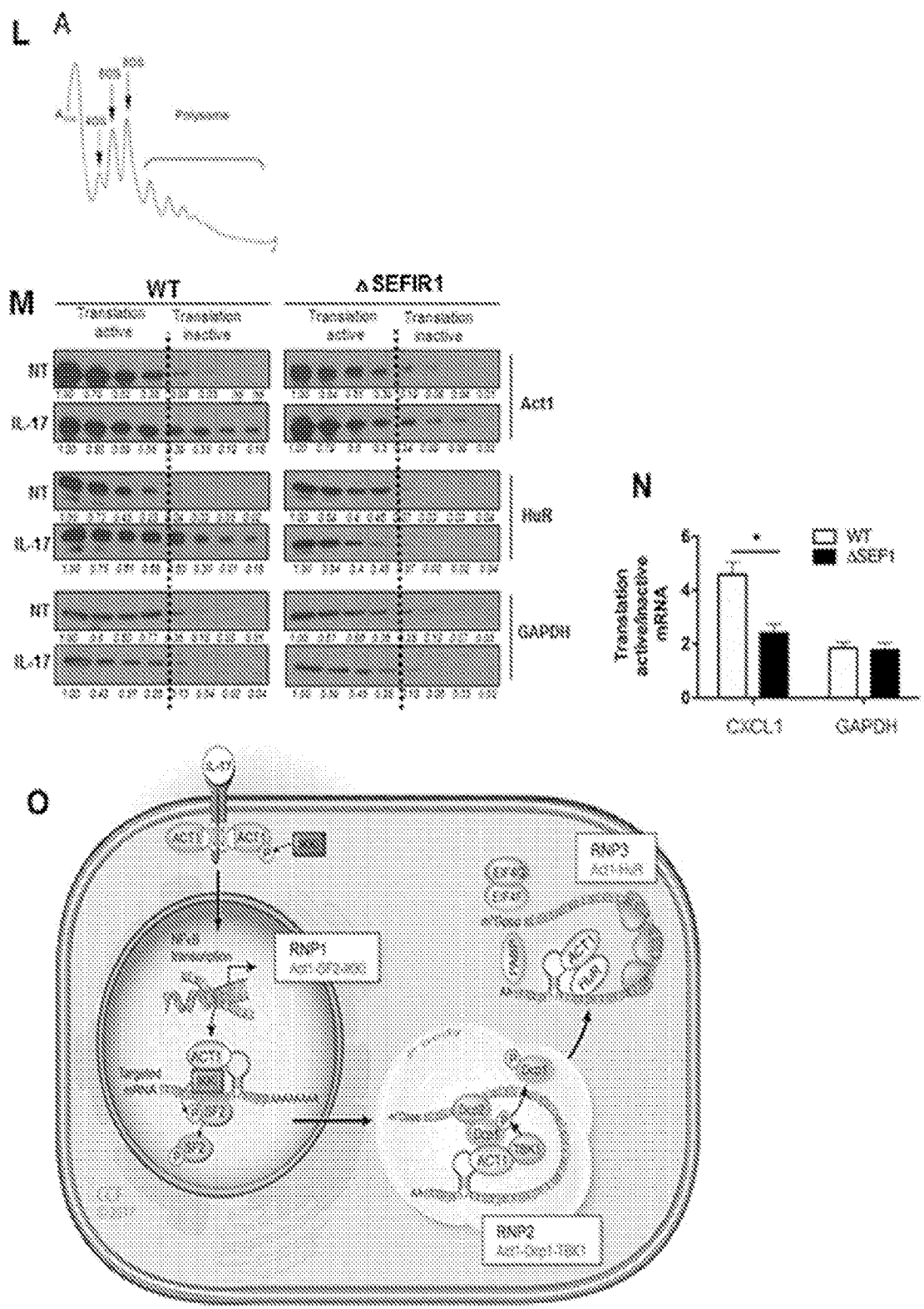

Our results described here have defined an Act1-RNP consisting of Act1-TBK1-Dcp1/2, which was designated as RNP2. While imaging studies indicated that SF2 and HuR were not co-localized with Dcp1 (FIG. 1F), we performed immunoprecipitation experiments to carefully examine the different Act1-RNPs. By co-immunoprecipitation with anti-Dcp1 using lysates from untreated and IL-17-treated Act1-expressing MEFs, we showed that while IL-17 induced Dcp1-Act1-TBK1 interaction in an RNA-dependent manner (sensitive to RNase treatment), SF2 and HuR were not detected in this RNP (RNP2). IL-17-induced Act1-SF2 complex (RNP1) was also sensitive to RNase pretreatment, but Dcp1-TBK1 and HuR were not found in this Act1-SF2-RNP (Supple FIG. 1B). Likewise, we failed to detect Dcp1-TBK1 and SF2 in IL-17-induced Act1-HuR RNP (RNP3). Taken together, these results suggest that the Act1-SF2, Act1-Dcp1/2 and Act1-HuR represent three independent RNPs. Importantly, deletion of SEFIR1 (ΔSEFIR1) abolished the formation of all three RNPs, implicating the importance of Act1's binding to mRNA for the formation of these Act1-RNPs (Supple FIG. 1A-C). In support of this, PLA imaging showed that deletion of SEFIR1 (ΔSEFIR1) also impaired the Act1-SF2 interaction (in the nucleus) and Act1-HuR interaction (in the cytosol) as well (FIG. 5A-B).

SF2 has been shown to mediate decay of cytokine and chemokine mRNA. It was reported that SF2 bound chemokine mRNA (induced by TNF) in the absence of IL-17 stimulation (Sun et al., 2011), whereas the SF2-mRNA interaction was much reduced after stimulation with IL-17 in an Act1-dependent manner (FIG. 5C). Interestingly, we now found that IL-17 failed to reduce SF2's binding to CXCL1 in Act1-deficient cells restored with ΔSEFIR1, suggesting that Act1's RNA binding might be required for the dissociation of SF2 from the mRNAs (FIG. 5C). One important question is how Act1's binding to mRNAs promotes the dissociation of SF2 from the mRNAs. We examined the sequences of CXCL1 required for SF2 binding. Surprisingly, we found that SF2 was able to bind the same region of CXCL1 as Act1: the SEFIR binding element (SBE); and the impairment of stem-loop C completely prevented the binding of SF2 (FIG. 5D-E). Addition of increasing amounts of Act1 to the RNA binding reaction attenuated SF2's binding to SBE (FIG. 5F). Notably, SF2 phosphorylation has been implicated as a mechanism for its dissociation from mRNA targets (Huynh et al., 2009). While both imaging and fractionation experiments indicated that Act1-SF2 RNP1 resides in the nucleus (FIGS. 5A-B and 5G), IKKi (a kinase required for IL-17-mediated mRNA stabilization (Bulek et al., 2011) was translocated into the nucleus and detected in the Act1-SF2 RNP1 in response to IL-17 stimulation (FIG. 5G). Importantly, IKKi indeed was able to phosphorylate SF2 in vitro (FIG. 5H) and incubation of recombinant IKKi with SF2 reduced the ability of SF2 to bind CXCL1 mRNA (FIG. 5I), implicating IKKi in preventing SF2's binding to mRNAs. Whereas IL-17-induced IKKi-SF2 and Act1-SF2 interaction were abolished in Act1-deficient MEFs restored with ΔSEFIR1 (FIG. 5C and FIG. 5G), Act1-IKKi interaction in both cytosol and nucleus was retained in these cells (FIG. 5G). These results suggest that IL-17 induces Act1-IKKi interaction prior to their translocation to the nucleus and Act1's binding to SF2-bound mRNAs in the nucleus allows IKKi to phosphorylate SF2, attenuating SF2's binding to the mRNA targets.

On the other hand, HuR was implicated in shifting target mRNAs to polysomes for protein translation and IL-17 stimulation induced the co-shift of Act1-HuR to the polysomes (Herjan et al., 2013; Tiedje et al., 2012). Notably, IL-17 induced the binding of HuR to CXCL1 in Act1-expressing MEFs, which was abolished in Act1-deficient MEFs restored with ΔSEFIR1, suggesting that Act1's RNA binding might also be required for HuR's recruitment to the target mRNAs (FIG. 5C). We examined the sequences of CXCL1 required for HuR binding and found that HuR bound to CXCL1 220-I (nt 720-830), but not CXCL1 220-II (nt 830-940) (FIGS. 5D and 5J). Interestingly, we found HuR and Act1 can simultaneously bind to CXCL1 220 (nt 720-940) (FIGS. 5D and 5K). Removal of nt 720-829 from CXCL1 220 abolished HuR binding, whereas Act1 binding was retained [CXCL1 220-II (nt 830-940)], indicating that HuR and Act1 have their independent binding sequences on CXCL1 (FIGS. 5D and 5K). These results indicate that besides blocking decapping in RNP2 (Act1l-TBK1-Dcp1/2), Act1-RNA binding has additional functions by forming RNP1 (Act1-SF2) and RNP3 (Act1-HuR). Since HuR is not part of RNP1 (Act1-SF2) (FIG. 5A-C), Act1 may facilitate HuR's binding to CXCL1 in vivo after competing off SF2 from target mRNAs. In support of this, IL-17-induced the co-shift of Act1-HuR to the polysomes (Herjan et al., 2013) was abolished in Act1-deficient MEFs restored with ΔSEFIR1 (FIG. 5L-M). Consistently, the ratio of CXCL1 mRNA in the translation active polysomes over the inactive fractions was substantially reduced in Act1-deficient MEFs restored with ΔSEFIR1 (FIG. 5M-N). Based on these results, we propose the following model for the actions of Act1-RNA binding (FIG. 5O): First, IL-17 induces Act1's binding to the mRNAs (such as CXCL1) in the nucleus (RNP1) preventing SF2-mdiated mRNA decay by competing off SF2's binding to the mRNAs which is further promoted by IKKi-mediated SF2 phosphorylation. Second, Act1 follows the mRNAs to the P-bodies (RNP2) inhibiting Dcp1/2-mediated mRNA decapping by employing TBK1 to phosphorylate Dcp1. Lastly, Act1-mRNAs are shifted to the polysomes by facilitating HuR's binding to mRNAs (RNP3) for protein translation.

Figure 6:
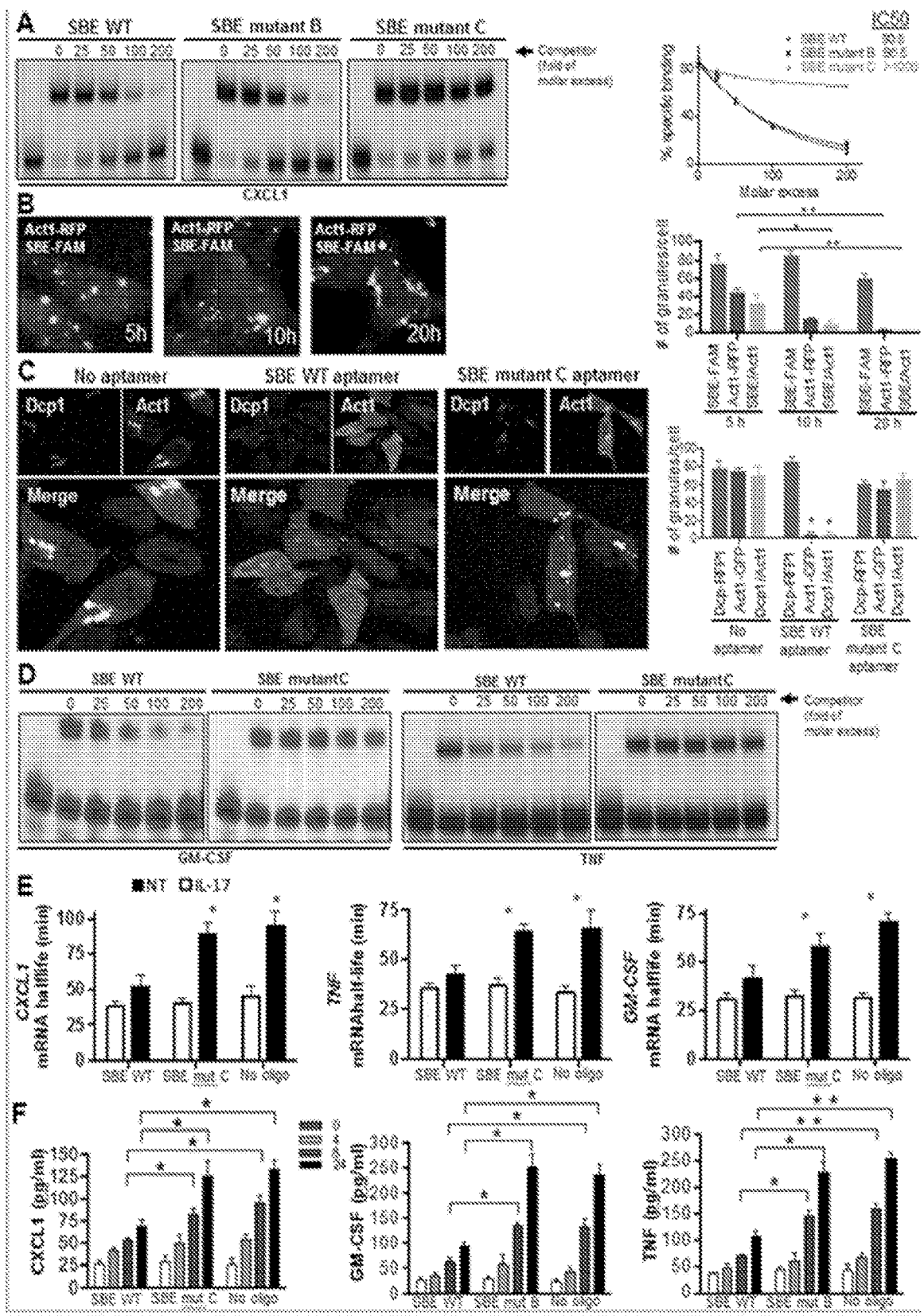
FIG. 6. SBE RNA aptamers abolished IL-17-induced mRNA stabilization of CXCL1, GM-CSF and TNF. A. SBE RNA aptamers were used to compete with CXCL1 220 probe for binding to Act1-SEFIR. The purified recombinant His-MBP-Act1 SEFIR (200 ng) was incubated with the CXCL1 220 in the presence of indicated folds of excess SBE aptamers followed by REMSA. SBE WT (CXCL1 47 as indicated in FIG. 3A), SBE mutant B and SBE mutant C (Table 2) were used in the competition assay. Graph quantifies the remaining Act1-SEFIR-bound CXCL1 220 probe in the presence of indicated concentrations of SBE aptamers. IC50 is calculated as the concentration of aptamers that displace 50% of bound CXCL1 220 probe from the Act1-SEFIR. Data are representative of three independent experiments (mean and s.d.). B. Confocal imaging was used to analyze the localization of RFP-Act1 and fluorescein amidite labeled SBE aptamer (SBE-FAM). HeLa cells were transfected with Act1-RFP, followed by a second transfection with SBE-FAM 24 hours later. Cells were fixed at indicated hours after SBE-FAM transfection and analyzed using confocal microscopy. Nuclei were stained with DAPI. Graph indicates the average numbers of SBE-FAM-positive, Act1-RFP-positive and SBE-FAM/Act1-RFP-double positive granules per cell at 5, 10 and 20 hours after SBE-FAM transfection. The quantification is based on the analysis of 50 expressing cells, followed by two-tailed Student's t-test. Data represent mean SD; *, p<0.05, **, p<0.01. C. Confocal imaging of Dcp1-RFP and Act1-GFP expressing cells transfected with 100 pmoles/ml of unlabeled SBE aptamers. HeLa cells were co-transfected with Dcp1-RFP and Act1-GFP, followed by a second transfection with unlabeled SBE aptamers 24 hours later. Cells were fixed 24 hours after SBE aptamers transfection and analyzed using confocal microscopy. Nuclei were stained with DAPI. Graph indicates the average numbers of Dcp1-RFP-positive, Act1-GFP-positive and Dcp1-RFP/Act1-GFP-double positive granules per cell 24 hours after SBE-FAM transfection. The quantification is based on the analysis of 50 expressing cells, followed by two-tailed Student's t-test. Data represent mean±SD; *, p<0.05. D. SBE RNA aptamers were used to compete with GM-CSF 3'UTR (513-785) and TNF 3'UTR (1362-1507) probes for binding to Act1-SEFIR. The purified recombinant His-MBP-Act1 SEFIR (200 ng) was incubated with the GM-CSF and TNF 3'UTR probes in the presence of indicated folds of excess SBE aptamers followed by REMSA. SBE WT (CXCL1 47 as indicated in FIG. 3A) and SBE mutant C (Table 2) were used in the competition assay. E.

SBE RNA Aptamers Abolished IL-17-induced mRNA Stabilization of CXCL1, GM-CSF and TNF Our results suggest that Act1 directly binds to the 3'UTRs of inflammatory genes, forming Act1-RNPs to inhibit mRNA decay and promote protein translation. Based on these findings, we hypothesized that RNA oligonucleotides corresponding to the SBE (SEFIR Binding Element) might inhibit the effect of Act1 in the defined RNPs and inflammatory gene expression. Interestingly, SBE RNA aptamers with or without mutation in stem-loop B was indeed able to compete off Act1 SEFIR's binding to the CXCL1 3'UTR (FIG. 6A). On the other hand, SBE RNA aptamer with mutated stem-loop C failed to compete off Act1 SEFIR's binding to CXCL1 3'UTR (FIG. 6A). To test the inhibitory effect of SBE RNA aptamers in cell culture and in vivo models, we generated fluorescently-labeled and partially modified SBE RNA aptamers where first three 5' and three 3' nucleotides were methylated (2'-OH). We co-transfected the fluorescent SBE RNA aptamers with SF2-HA or Act1-RFP into HeLa cells. The transfected fluorescent SBE RNA aptamers mainly resided in the cytoplasm and was detected in Act1 granules (FIG. 6B). Interestingly, we observed that the Act1 granules were substantially reduced over time in cells transfected with SBE RNA aptamers, implicating that this SBE RNA aptamers might be disrupting the Act1's co-localization with the P-bodies (FIG. 6B). We indeed found that SBE RNA aptamers, but not SBE aptamers with mutated stem-loop C, abolished the formation of Act1 granules and Act1's co-localization with Dcp1 (FIG. 6C).

These results suggest that SBE RNA aptamers-mediated inhibition of Act1's RNA binding activity may affect other transcripts in addition to CXCL1. In support of this, the SBE RNA aptamers was also able to compete off Act1 SEFIR's binding to the 3' UTRs of GM-CSF and TNF (FIG. 6D and Supple. FIG. 6B suggesting that the binding of SBE RNA aptamers to Act1 SEFIR blocks Act1's binding to the mRNA targets. These results suggest that the SBE RNA aptamers has the potential to be an inhibitory agent for blocking IL-17-induced inflammatory response. We indeed found that transfection of SBE RNA aptamers reduced IL-17-mediated mRNA stabilization and the production of CXCL1, GM-CSF and TNF (FIG. 6E-F).

SBE RNA Aptamers Inhibited IL-17-Dependent Skin Hyperplasia

Secukinumab (anti-IL-17A) showed great efficacy for psoriasis and has been approved by FDA for treatment of psoriasis. Aberrant keratinocyte proliferation and neutrophilic inflammation are well-known hallmarks of pathogenesis of psoriasis. To examine the impact of SBE RNA aptamers on IL-17A-induced epidermal proliferation and inflammation, the ears of WT C57BL/6 female mice were injected intradermally with IL-17A with SBE RNA aptamers or SBE mutant aptamers (mutated stem-loop C as a negative control) for 6 consecutive days. We found that SBE RNA aptamer, but not mutant aptamer substantially reduced IL-17A-dependent epidermal hyperplasia and neutrophil infiltration in the ears (FIG. 7A-C). Likewise, SBE RNA aptamer, but not mutant aptamer greatly diminished IL-17A-induced expression of cxcl1, gm-csf and tnf in the ears (FIG. 7D). Taken together, these data indicate that IL-17A induces keratinocytes proliferation and neutrophil infiltration, resulting in epidermal hyperplasia, which were effectively blocked by SBE RNA aptamers.

The SEFIR domain, a conserved motif present in the cytoplasmic regions of IL-17 receptor subunits and adaptor Act1, mediates the recruitment of Act1 to the receptor upon IL-17 stimulation. Here we have unexpectedly identified SEFIR of Act1 as a direct RNA binding domain, rendering Act1 RNA binding activity to stabilize otherwise unstable mRNAs of the pro-inflammatory genes (CXCL1, TNF and GM-CSF) in response to IL-17 stimulation. We found that Act1 directly binds to the 3'-UTRs of inflammatory mRNAs to form distinct RNPs in several subcellular compartments including P-bodies controlling mRNA metabolism. Structure-function analysis showed that Act1 SEFIR binds to a stem-loop structure (named as SBE) in the CXCL1 3'UTR. RNA aptamers containing SBE abolished Act1's binding to the target mRNAs and attenuated IL-17-mediated mRNA stabilization. The physiologic relevance of the RNA-binding activity of Act1 is illustrated by our discovery that SBE RNA aptamers inhibited IL-17-induced skin inflammation. While the present invention is not limited to any particular mechanism, and an understanding of the mechanism is not necessary to practice the invention, it is believed that this study demonstrates that the receptor-proximal adaptor Act1 directly binds to mRNAs to control the steps of RNA metabolism, which provides a novel molecular mechanism of inflammatory response via receptor-specific mRNA stabilization of select inflammatory genes. Moreover, the discovery of a non-canonical function of Act1 will allow the development of new therapeutic strategies for autoimmune inflammatory diseases.

In addition to mRNAs of inflammatory genes, short half-lives allow dynamic regulation of a wide spectrum of transcripts whose expression also needs to be switched on and off rapidly, including transcription factors, signaling components, and cell cycle proteins (Schoenberg and Maquat, 2012). These unstable mRNAs possess destabilizing sequences in their 3'UTRs (including AU-rich element and Stem-Loops) that are recognized by RNA binding proteins (ARE and SL binding proteins) to mediate the degradation of the mRNAs via deadenylation, decapping, and exonucleolytic degradation (Mino et al., 2015; Schoenberg and Maquat, 2012; Stumpo et al., 2010). While multiple mRNA destabilizing mechanisms have been discovered, it remains unclear how the different classes of mRNAs with short half-lives are stabilized in a cell context and stimulus specific manner. Although ARE binding protein SF2 and HuR were previously implicated in IL-17-induced mRNA stabilization, they cannot explain the receptor-specific mRNA stabilization of select inflammatory genes (Brennan and Steitz, 2001; Herjan et al., 2013). Notably, HuR has a broad range of mRNA targets including transcription factors, signaling components, and cell cycle proteins, whereas IL-17 stimulation does not stabilize all of the HuR mRNA targets (Mitchell and Parker, 2014; Schoenberg and Maquat, 2012; Mukherjee et al., 2011). Likewise, SF2 has been implicated in various aspects RNA metabolism, including RNA splicing, mRNA export, and nonsense-mediated decay (Cao et al., 1997; Krainer et al., 1990; Lemaire et al., 2002; Reed and Cheng, 2005; Sun et al., 2011; Zhong et al., 2009). Therefore, the discovery of Act1 as a direct RNA binding protein is a conceptual advancement for our understanding how short-lived mRNAs can be stabilized in a stimulus specific manner via a receptor-mediated direct mechanism.

In eukaryotes, mRNA decay pathways are initiated by deadenylation carried out by the CCR4-CAF1-NOT deadenylase complex (Chen and Shyu, 2011). An exonuclease complex (the exosome) can degrade mRNAs in a 3'-5' direction post deadenylation; and the Dcp1/Dcp2 decapping enzyme exposes the mRNA to degradation from the 5' end using the exonuclease Xrn1, simultaneously shutting down translation initiation (Arribas-Layton et al., 2013; Franks and Lykke-Andersen, 2008; Schoenberg and Maquat, 2012). Previous studies have shown that the mRNA targeting into decapping involves the formation of translationally repressed mRNP, which can be targeted to P-bodies and stress granules (Anderson et al., 2015; Arribas-Layton et al., 2013; Franks and Lykke-Andersen, 2008). We here found that one of the Act1-containing RNPs is localized in the P-bodies (RNP2, not in the stress granules) and Act1 is able to inhibit the decapping activity of Dcp1/Dcp2 complex by bringing a kinase, TBK1 to phosphorylate Dcp1 and disrupt Dcp1/Dcp2 complex. As a result, Act1-bound mRNAs including CXCL1, TNF and GM-CSF are stabilized and translated. Our findings are consistent with the concepts that the translation and mRNA decay are in competition with each other and the processes of translation and mRNA degradation are coupled. Therefore, we propose that Act1-RNP-mediated inhibition of decapping releases the mRNAs trapped in the P-bodies for return to translation. Supporting the potential role Act1 in linking mRNA stabilization to protein translation, it was previously reported that IL-17 stimulation induced the co-shift of Act1-HuR to the polysomes (Herjan et al., 2013). Importantly, we now found that RNase pretreatment of the lysates abolished the detection of Act1-HuR interaction, suggesting that the Act1's interaction with HuR is RNA-dependent. Consistently, we found HuR and Act1 can simultaneously bind to CXCL1; and IL-17 induced the binding of HuR to CXCL1 was abolished in Act1-deficient cells restored with ΔSEFIR1. These results suggest that Act1's RNA binding is required for HuR's recruitment to the target mRNAs. Based on these findings, we proposed that Act1-bound mRNAs are shifted to the polysomes by facilitating HuR's binding to mRNAs (RNP3) for protein translation. In support of this, we indeed found that IL-17 stimulation induced the co-shift of Act1-HuR to the polysomes was abolished in Act1-deficient cells restored with ΔSEFIR1.

Although cytoplasmic mRNA decay seems to be the dominant pathway for mRNA turnover in eukaryotes, recent studies have implicated regulation of mRNA stability in the nucleus. It has been estimated that only a minor proportion, about 30% of transcripts in eukaryotes, is processed to be mRNA and exported to the cytoplasm (Jackson et al., 2000). While aberrant RNA processing contributes to the trapping the nuclear transcripts in the nucleus, both 3' to 5' and 5' to 3' exoribonucleases have been found in the nucleus (Brannan et al., 2012; Bresson et al., 2017; Gudipati et al., 2012). Therefore, it is conceivable that active intervention to prevent degradation of nuclear transcripts is required for abundant production and translation of mRNAs. In support of this, while SF2 has been shown to mediate mRNA decay, we found Act1 forms an RNP with SF2 in the nucleus (RNP1). IL-17 stimulation induced the dissociation of SF2 from the mRNA targets, which was abolished in Act1-deficient cells restored with ΔSEFIR1, suggesting that Act1's RNA binding is required for preventing SF2-dependent mRNA decay. Interestingly, we found that SF2 was able to bind the same region of CXCL1 as Act1. The addition of increasing amounts of Act1 to the RNA binding reaction attenuated SF2's binding to the target mRNA, suggesting that the two proteins directly compete for binding to the same target mRNA. Additionally, SF2 phosphorylation has been implicated as a mechanism for its dissociation from mRNA targets (Cao et al., 1997; Xiao and Manley, 1997). In support of this, we found that IL-17 induces Act1-IKKi nuclear translocation and Act1's binding to SF2-bound mRNAs in the nucleus allows IKKi to phosphorylate SF2, preventing SF2's binding to the mRNA targets. However, it remains unclear how SF2 mediates mRNA decay. SF2-mediated mRNA decay might be through active recruitment of exonucleases. Alternatively, SF2-bound mRNAs may be simply trapped in the nucleus and are degraded over time. In any case, with the help of IKKi, Act1 binding to mRNAs drives off SF2, resulting in stabilization of mRNAs.

Taken together, while the present invention is not limited to any particular mechanism, we propose the following model for the actions of Act1-RNA binding for IL-17-induced inflammatory response. Upon IL-17 stimulation, multiple signaling pathways (including NFkB and MAPKs) are activated to induce the gene transcription of cytokines and chemokines. Act1 then directly binds the mRNAs of cytokines and chemokines to stabilize these otherwise unstable mRNAs for the production of the pro-inflammatory mediators. Act1's binding to mRNAs of inflammatory genes results in the formation of multiple RNPs controlling different steps of mRNA metabolism. First, Act1 binds to the mRNAs in the nucleus (RNP1) inhibiting SF2-mdiated mRNA degradation by competing off SF2's binding to mRNAs, which was further facilitated by IKKi-mediated SF2 phosphorylation. One of the possible roles of Act1-RNP1 in the nucleus is to protect the degradation and/or trapping of nascent nuclear transcripts. Second, Act1 forms a RNP (RNP2) in the P-bodies blocking Dcp1/2-mediated mRNA decapping by recruiting TBK1 to phosphorylate Dcp1. The Act1-RNP2 may represent an action for how to resolve the competition between mRNA translation and degradation. Finally, Act1-mRNAs are co-shifted with HuR to the polysomes (RNP3) for protein translation. Taken together, the study here provides the first example of a receptor-interacting adaptor molecule, Act1, playing a direct role in mRNA metabolism, orchestrating receptor-mediated selectivity of mRNA stabilization and translation. Additionally, it is exciting to find that SBE RNA aptamers was able to disrupt the co-localization of Act1 with P-bodies.

REFERENCES

Aizer, et al., (2013). The P body protein Dcp1a is hyperphosphorylated during mitosis. PloS One 8, e49783.

Anderson, et al., (2015). Stress granules, P-bodies and cancer. Biochim. Biophys. Acta 1849, 861-870.

Arribas-Layton, et al., (2013). Structural and functional control of the eukaryotic mRNA decapping machinery. Biochim. Biophys. Acta 1829, 580-589.

Brannan, et al. (2012). mRNA decapping factors and the exonuclease Xm2 function in widespread premature termination of RNA polymerase II transcription. Mol. Cell 46, 311-324.

Brennan, et al., (2001). HuR and mRNA stability. Cell. Mol. Life Sci. CMLS 58, 266-277.

Bresson, et al., (2017). Nuclear RNA Decay Pathways Aid Rapid Remodeling of Gene Expression in Yeast. Mol. Cell 65, 787-800.e5.

Bulek, et al. (2011). The inducible kinase IKKi is required for IL-17-dependent signaling associated with neutrophilia and pulmonary inflammation. Nat. Immunol. 12, 844-852.

Cao, et al., (1997). Both phosphorylation and dephosphorylation of ASF/SF2 are required for pre-mRNA splicing in vitro. RNA 3, 1456-1467.

Chang, et al., (2006). Act1 adaptor protein is an immediate and essential signaling component of interleukin-17 receptor. J. Biol. Chem. 281, 35603-35607.

Chen, et al., (2011). Mechanisms of deadenylation-dependent decay. Wiley Interdiscip. Rev. RNA 2, 167-183.

Chesné, et al., (2015). Prime role of IL-17A in neutrophilia and airway smooth muscle contraction in a house dust mite-induced allergic asthma model. J. Allergy Clin. Immunol. 135, 1643-1643.e3.

Cho, et al. (2010). IL-17 is essential for host defense against cutaneous *Staphylococcus aureus* infection in mice. J. Clin. Invest. 120, 1762-1773.

Conti, et al. (2009). Th17 cells and IL-17 receptor signaling are essential for mucosal host defense against oral candidiasis. J. Exp. Med. 206, 299-311.

Cua, et al., (2010). Innate IL-17-producing cells: the sentinels of the immune system. Nat. Rev. Immunol. 10, 479-489.

Datta, et al., (2008). Tristetraprolin regulates CXCL1 (KC) mRNA stability. J. Immunol. Baltim. Md. 1950 180, 2545-2552.

Datta, et al., (2010). IL-17 regulates CXCL1 mRNA stability via an AUUUA/tristetraprolin-independent sequence. J. Immunol. Baltim. Md. 1950 184, 1484-1491.

Deng, et al., (2004). An improved protocol for rapid freezing of protein samples for long-term storage. Acta Crystallogr. D Biol. Crystallogr. 60, 203-204.

Deng, et al., (2008). Structure of the ROC domain from the Parkinson's disease-associated leucine-rich repeat kinase 2 reveals a dimeric GTPase. Proc. Natl. Acad. Sci. U.S. A. 105, 1499-1504.

Erickson, et al., (2011). Cytoplasmic mRNP granules at a glance. J. Cell Sci. 124, 293-297.

Franks, et al., (2008). The control of mRNA decapping and P-body formation. Mol. Cell 32, 605-615.

Gu, et al., (2013). IL-17 family: cytokines, receptors and signaling. Cytokine 64, 477-485.

Gudipati, et al., (2012). Extensive degradation of RNA precursors by the exosome in wild-type cells. Mol. Cell 48, 409-421.

Harrington, et al., (2005). Interleukin 17-producing CD4+ effector T cells develop via a lineage distinct from the T helper type 1 and 2 lineages. Nat. Immunol. 6, 1123-1132.

Hartupee, et al., (2007). IL-17 enhances chemokine gene expression through mRNA stabilization. J. Immunol. Baltim. Md. 1950 179, 4135-4141.

Herjan, et al. (2013). HuR is required for IL-17-induced Act1-mediated CXCL1 and CXCL5 mRNA stabilization. J. Immunol. Baltim. Md. 1950 191, 640-649.

Hu, et al, (2009). Co-translational mRNA decay in Saccharomyces cerevisiae. Nature 461, 225-229.

Huynh, et al., (2009). Allosteric Interactions Direct Binding and Phosphorylation of ASF/SF2 by SRPK1. Biochemistry (Mosc.) 48, 11432-11440.

Jackson, et al., (2000). The balance sheet for transcription: an analysis of nuclear RNA metabolism in mammalian cells. FASEB J. 14, 242-254.

Kang, et al. (2010). Astrocyte-restricted ablation of interleukin-17-induced Act1-mediated signaling ameliorates autoimmune encephalomyelitis. Immunity 32, 414-425.

Kolls, et al. (2010). The role of Th17 cytokines in primary mucosal immunity. Cytokine Growth Factor Rev. 21, 443-448.

Krainer, et al., (1990). The essential pre-mRNA splicing factor SF2 influences 5' splice site selection by activating proximal sites. Cell 62, 35-42.

Lemaire, et al., (2002). Stability of a PKCI-1-related mRNA is controlled by the splicing factor ASF/SF2: a novel function for SR proteins. Genes Dev. 16, 594-607.

Leppek, et al., (2013). Roquin promotes constitutive mRNA decay via a conserved class of stem-loop recognition motifs. Cell 153, 869-881.

Li, et al., (2000). Act1, an NF-kappa B-activating protein. Proc. Natl. Acad. Sci. U.S.A. 97, 10489-10493.

Liu, et al. (2011). A CC' loop decoy peptide blocks the interaction between Act1 and IL-17RA to attenuate IL-17- and IL-25-induced inflammation. Sci. Signal. 4, ra72.

Liu, et al. (2017). The flavonoid cyanidin blocks binding of the cytokine interleukin-17A to the IL-17RA subunit to alleviate inflammation in vivo. Sci Signal 10, eaaf8823.

Milner, et al., (2013). The cup runneth over: lessons from the ever-expanding pool of primary immunodeficiency diseases. Nat. Rev. Immunol. 13, 635-648.

Mino, et al. (2015). Regnase-1 and Roquin Regulate a Common Element in Inflammatory mRNAs by Spatiotemporally Distinct Mechanisms. Cell 161, 1058-1073.

Mitchell, et al., (2014). Principles and properties of eukaryotic mRNPs. Mol. Cell 54, 547-558.

Mukherjee, et al., (2012). Identification of cytoplasmic capping targets reveals a role for cap homeostasis in translation and mRNA stability. Cell Rep. 2, 674-684.

Mukherjee, et al., (2011). Integrative regulatory mapping indicates that the RNA-binding protein HuR couples pre-mRNA processing and mRNA stability. Mol. Cell 43, 327-339.

Novatchkova, et al., (2003). The STIR-domain superfamily in signal transduction, development and immunity. Trends Biochem. Sci. 28, 226-229.

Park, et al. (2005). A distinct lineage of CD4 T cells regulates tissue inflammation by producing interleukin 17. Nat. Immunol. 6, 1133-1141.

Patel, et al., (2013). Effect of IL-17A blockade with secukinumab in autoimmune diseases. Ann. Rheum. Dis. 72 Suppl 2, ii116-ii123.

Qian, et al. (2007). The adaptor Act1 is required for interleukin 17-dependent signaling associated with autoimmune and inflammatory disease. Nat. Immunol. 8, 247-256.

Qu, et al., (2012). TRAF6-Dependent Act1 Phosphorylation by the IκB Kinase-Related Kinases Suppresses Interleukin-17-Induced NF-κB Activation. Mol. Cell. Biol. 32, 3925-3937.

Reed, et al., (2005). TREX, SR proteins and export of mRNA. Curr. Opin. Cell Biol. 17, 269-273.

Ruzankina, et al., (2007). Deletion of the developmentally essential gene ATR in adult mice leads to age-related phenotypes and stem cell loss. Cell Stem Cell 1, 113-126.

Rzeczkowski, et al., (2011). c-Jun N-terminal kinase phosphorylates DCPla to control formation of P bodies. J. Cell Biol. 194, 581-596.

Schoenberg, et al., (2012). Regulation of cytoplasmic mRNA decay. Nat. Rev. Genet. 13, 246-259.

She, et al., (2008). Structural basis of dcp2 recognition and activation by dcp1. Mol. Cell 29, 337-349.

Shen, et al., (2008). Structure-function relationships in the IL-17 receptor: implications for signal transduction and therapy. Cytokine 41, 92-104.

Stoecklin, et al., (2006). ARE-mRNA degradation requires the 5'-3' decay pathway. EMBO Rep. 7, 72-77.

Stumpo, et al., (2010). Inflammation: cytokines and RNA-based regulation. Wiley Interdiscip. Rev. RNA 1, 60-80.

Sun, et al., (2011). Treatment with IL-17 prolongs the half-life of chemokine CXCL1 mRNA via the adaptor TRAF5 and the splicing-regulatory factor SF2 (ASF). Nat. Immunol. 12, 853-860.

Swaidani, et al., (2009). The critical role of epithelial-derived Act1 in IL-17- and IL-25-mediated pulmonary inflammation. J. Immunol. Baltim. Md. 1950 182, 1631-1640.

Tiedje, et al., (2012). The p38/MK2-driven exchange between tristetraprolin and HuR regulates AU-rich element-dependent translation. PLoS Genet. 8, e1002977.

Toy, et al., (2006). Cutting edge: interleukin 17 signals through a heteromeric receptor complex. J. Immunol. Baltim. Md. 1950 177, 36-39.

Velichko, et al., (2016). A Novel Nuclear Function for the Interleukin-17 Signaling Adaptor Protein Act1. PLOS ONE 11, e0163323.

Wang, et al., (2002). The hDcp2 protein is a mammalian mRNA decapping enzyme. Proc. Natl. Acad. Sci. U.S.A. 99, 12663-12668.

Xiao, et al., (1997). Phosphorylation of the ASF/SF2 RS domain affects both protein-protein and protein-RNA interactions and is necessary for splicing. Genes Dev. 11, 334-344.

Zhang, et al., (2014). Structure of the unique SEFIR domain from human interleukin 17 receptor A reveals a composite ligand-binding site containing a conserved α-helix for Act1 binding and IL-17 signaling. Acta Crystallogr. D Biol. Crystallogr. 70, 1476-1483.

Zhong, et al., (2009). SR proteins in Vertical Integration of Gene Expression from Transcription to RNA Processing to Translation. Mol. Cell 35, 1-10.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of treating an IL-17a related disease or condition comprising:
   treating a subject with an IL-17a related disorder or condition with a composition,
   wherein said composition comprises a first nucleic acid sequence, wherein said first nucleic acid sequence comprises an SBE nucleic acid sequence that binds a SEFIR domain of an ACT1 protein, and
   wherein at least a portion of said SBE nucleic acid sequence is from a gene selected from the group consisting of: CXCL1, TNF, GM-CSF, Zc3h12a, Serpinc1, Cyp2d26, C3, H2-Q10, Nfkbiz, lgfbp1, Ccl7, Asb15, Ccl2, Cgn, Cxcl5, G6pc, Cp, Slc27a2, Apoc1, Uox and Bcl3.

2. The method of claim 1, wherein at least a portion of said SBE nucleic acid sequence is from a gene selected from said CXCL1, GM-CSF, and TNF.

3. The method of claim 1, wherein said SBE nucleic acid sequence comprises a sequence shown in SEQ ID NOs:53-61.

4. The method of claim 1, wherein said SBE nucleic acid sequence comprises RNA bases.

5. The method of claim 1, wherein said SBE nucleic acid sequence comprises DNA bases.

6. The method of claim 1, wherein said treating reduces or eliminates at least one symptom related to said IL-17a related disease or condition.

7. The method of claim 1, wherein said IL-17a related disease is selected from the group consisting of: psoriasis, chronic plaque, asthma, an autoimmune disease, an inflammatory condition, rheumatoid arthritis, and multiple sclerosis.

8. The method of claim 1, wherein said SBE nucleic acid sequence comprises, consist of, or consists essentially of: nucleotides 810-857 of said CXCL1 gene, ii) nucleotides 830-856 of said CXCL1 gene, or iii) nucleotides 800-835 of said CXCL1 gene.

9. The method of claim 1, wherein said subject is human.

10. The method of claim 1, wherein said SBE nucleic acid sequence is from a human gene.

11. The method of claim 1, wherein said ACT1 protein is human ACT1 protein.

12. The method of claim 1, wherein said first nucleic acid sequence is between 12 and 70 nucleotides in length.

13. A composition comprising a first nucleic acid sequence, wherein said first nucleic acid sequence comprises an SBE nucleic acid sequence that binds a SEFIR domain of an ACT1 protein,
   wherein at least a portion of said SBE nucleic acid sequence is from a gene selected from the group consisting of: CXCL1, TNF, GM-CSF, Zc3h12a, Serpinc1, Cyp2d26, C3, H2-Q10, Nfkbiz, lgfbp1, Ccl7, Asb15, Ccl2, Cgn, Cxcl5, G6pc, Cp, Slc27a2, Apoc1, Uox and Bcl3, and
   wherein said first nucleic acid sequence comprises modified bases to improve stability in vivo.

14. The composition of claim 13, wherein said SBE nucleic acid sequence is from a gene selected from said CXCL1, GM-CSF, and TNF.

15. The composition of claim 13, wherein said first nucleic acid sequence is no longer than 70 bases and comprises at least: i) nucleotides 830-856 of said CXCL1 gene, or ii) nucleotides 810-857 of said CXCL1 gene.

16. The composition of claim 13, wherein said first nucleic acid sequence is composed of RNA bases.

17. The composition of claim 13, wherein said first nucleic acid is present in said composition at a level that is therapeutic when administered to a subject with an IL-17a related disease or condition.

18. The composition of claim 13, wherein said SBE nucleic acid sequence is from a gene selected from said: zc3h12a, Serpinc1, Cyp2d26, C3, H2-Q10, and Nfkbiz.

19. The composition of claim 13, wherein said SBE nucleic acid sequence is from a gene selected from said: lgfbp1, Ccl7, Asb15, ccl2, asb15, Cgn, and Cxc15.

20. The composition of claim 13, wherein said SBE nucleic acid sequence is from a gene selected from said: g6pc, Cp, slc27a2, Apoc1, Uox, and bcl3.

* * * * *

```
                        SEQUENCE LISTING

<160> NUMBER OF SEQ ID NOS: 129

<210> SEQ ID NO 1
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (14)..(17)
<223> OTHER INFORMATION: n is a, c, g, t or u

<400> SEQUENCE: 1
nnnngnuaau ancnnnn                                                   17

<210> SEQ ID NO 2
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (11)..(11)
<223> OTHER INFORMATION: n is a, c, g, t or u

<400> SEQUENCE: 2
ngnuaauanc n                                                         11

<210> SEQ ID NO 3
<211> LENGTH: 28
<212> TYPE: DNA
<213> ORGANISM: Artificial sequence
<220> FEATURE:
<223> OTHER INFORMATION: Synthetic

<400> SEQUENCE: 3
ggaagaattc ctgtgtttgt atgtcttg                                       28

<210> SEQ ID NO 4
<211> LENGTH: 30
```

<212> TYPE: DNA
<213> ORGANISM: Artificial sequence
<220> FEATURE:
<223> OTHER INFORMATION: Synthetic

<400> SEQUENCE: 4
ggaaggatcc cttttatttt tacttcattt                                                 30

<210> SEQ ID NO 5
<211> LENGTH: 31
<212> TYPE: DNA
<213> ORGANISM: Artificial sequence
<220> FEATURE:
<223> OTHER INFORMATION: Synthetic

<400> SEQUENCE: 5
ggaagaattc gtatggtcaa cacgcacgtg t                                               31

<210> SEQ ID NO 6
<211> LENGTH: 29
<212> TYPE: DNA
<213> ORGANISM: Artificial sequence
<220> FEATURE:
<223> OTHER INFORMATION: Synthetic

<400> SEQUENCE: 6
ggaaggatcc ctctgtcccg agcgagacg                                                  29

<210> SEQ ID NO 7
<211> LENGTH: 30
<212> TYPE: DNA
<213> ORGANISM: Artificial sequence
<220> FEATURE:
<223> OTHER INFORMATION: Synthetic

<400> SEQUENCE: 7
ggaagaattc gtatggtcaa cacgcacgtg                                                 30

<210> SEQ ID NO 8
<211> LENGTH: 31
<212> TYPE: DNA
<213> ORGANISM: Artificial sequence
<220> FEATURE:
<223> OTHER INFORMATION: Synthetic

<400> SEQUENCE: 8
ggaaggatcc ctctgtcccg agcgagacga g                                               31

<210> SEQ ID NO 9
<211> LENGTH: 31
<212> TYPE: DNA
<213> ORGANISM: Artificial sequence
<220> FEATURE:
<223> OTHER INFORMATION: Synthetic

<400> SEQUENCE: 9
ggaaggatcc ctctgtcccg agcgagacga g                                               31

<210> SEQ ID NO 10
<211> LENGTH: 31
<212> TYPE: DNA
<213> ORGANISM: Artificial sequence
<220> FEATURE:
<223> OTHER INFORMATION: Synthetic

<400> SEQUENCE: 10
ggaaggatcc ctctgtcccg agcgagacga g                     31

<210> SEQ ID NO 11
<211> LENGTH: 28
<212> TYPE: DNA
<213> ORGANISM: Artificial sequence
<220> FEATURE:
<223> OTHER INFORMATION: Synthetic

<400> SEQUENCE: 11
ggaagaattc ttgacgcttc ccttggac                        28

<210> SEQ ID NO 12
<211> LENGTH: 29
<212> TYPE: DNA
<213> ORGANISM: Artificial sequence
<220> FEATURE:
<223> OTHER INFORMATION: Synthetic

<400> SEQUENCE: 12
ggaaggatcc gaccaggaga aacagggtt                       29

<210> SEQ ID NO 13
<211> LENGTH: 29
<212> TYPE: DNA
<213> ORGANISM: Artificial sequence
<220> FEATURE:
<223> OTHER INFORMATION: Synthetic

<400> SEQUENCE: 13
ggaaggatcc gaccaggaga aacagggtt                       29

<210> SEQ ID NO 14
<211> LENGTH: 34
<212> TYPE: DNA
<213> ORGANISM: Artificial sequence
<220> FEATURE:
<223> OTHER INFORMATION: Synthetic

<400> SEQUENCE: 14
ggaaggatcc acagggttaa agaatgtaaa aggg                 34

<210> SEQ ID NO 15
<211> LENGTH: 28
<212> TYPE: DNA
<213> ORGANISM: Artificial sequence
<220> FEATURE:
<223> OTHER INFORMATION: Synthetic

<400> SEQUENCE: 15
ggaagaattc ccttggacat tttgtgtc                        28

<210> SEQ ID NO 16
<211> LENGTH: 29
<212> TYPE: DNA
<213> ORGANISM: Artificial sequence
<220> FEATURE:
<223> OTHER INFORMATION: Synthetic

<400> SEQUENCE: 16
ggaaggatcc tgtaaaaggg cattatgcc                       29

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
ctggtatctg ggcttggtga tgg                                            23

<210> SEQ ID NO 18
<211> LENGTH: 23
<212> TYPE: DNA
<213> ORGANISM: Artificial sequence
<220> FEATURE:
<223> OTHER INFORMATION: Synthetic

<400> SEQUENCE: 18
ctggtatctg ggcttggtga tgg                                            23

<210> SEQ ID NO 19
<211> LENGTH: 29
<212> TYPE: DNA
<213> ORGANISM: Artificial sequence
<220> FEATURE:
<223> OTHER INFORMATION: Synthetic

<400> SEQUENCE: 19
ggaaggatcc tgtaaaaggg cattatgcc                                      29

<210> SEQ ID NO 20
<211> LENGTH: 32
<212> TYPE: DNA
<213> ORGANISM: Artificial sequence
<220> FEATURE:
<223> OTHER INFORMATION: Synthetic

<400> SEQUENCE: 20
ggaaggatcc gcttatgttt aaaacaaaat at                                  32

<210> SEQ ID NO 21
<211> LENGTH: 32
<212> TYPE: DNA
<213> ORGANISM: Artificial sequence
<220> FEATURE:
<223> OTHER INFORMATION: Synthetic

<400> SEQUENCE: 21
ggaagaattc gaccggccag atgaggctgg cc                                  32

<210> SEQ ID NO 22
<211> LENGTH: 31
<212> TYPE: DNA
<213> ORGANISM: Artificial sequence
<220> FEATURE:
<223> OTHER INFORMATION: Synthetic

<400> SEQUENCE: 22
ggaaggatcc cttgaataaa tatggaatat g                                   31

<210> SEQ ID NO 23
<211> LENGTH: 29
<212> TYPE: DNA
<213> ORGANISM: Artificial sequence
<220> FEATURE:
<223> OTHER INFORMATION: Synthetic

<400> SEQUENCE: 23
ggaagctagc atgcctcctc agcttcaag                                      29

<210> SEQ ID NO 24
<211> LENGTH: 30
<212> TYPE: DNA
<213> ORGANISM: Artificial sequence
<220> FEATURE:
<223> OTHER INFORMATION: Synthetic

<400> SEQUENCE: 24
ggaagtcgac tgcaagggaa ccacctgaag                                       30

<210> SEQ ID NO 25
<211> LENGTH: 30
<212> TYPE: DNA
<213> ORGANISM: Artificial sequence
<220> FEATURE:
<223> OTHER INFORMATION: Synthetic

<400> SEQUENCE: 25
ggaagaattc atggaggcgc tgagtcgagc                                       30

<210> SEQ ID NO 26
<211> LENGTH: 34
<212> TYPE: DNA
<213> ORGANISM: Artificial sequence
<220> FEATURE:
<223> OTHER INFORMATION: Synthetic

<400> SEQUENCE: 26
ggaagtcgac tgtaggttgt ggttgtcttt gttc                                  34

<210> SEQ ID NO 27
<211> LENGTH: 31
<212> TYPE: DNA
<213> ORGANISM: Artificial sequence
<220> FEATURE:
<223> OTHER INFORMATION: Synthetic

<400> SEQUENCE: 27
ggaagctagc atgcagagca cagccaatta c                                     31

<210> SEQ ID NO 28
<211> LENGTH: 31
<212> TYPE: DNA
<213> ORGANISM: Artificial sequence
<220> FEATURE:
<223> OTHER INFORMATION: Synthetic

<400> SEQUENCE: 28
ggaagtcgac tggacatcag gaggtgctgg g                                     31

<210> SEQ ID NO 29
<211> LENGTH: 29
<212> TYPE: DNA
<213> ORGANISM: Artificial sequence
<220> FEATURE:
<223> OTHER INFORMATION: Synthetic

<400> SEQUENCE: 29
ggaaggtacc atgcagagca cttctaatc                                        29

<210> SEQ ID NO 30
<211> LENGTH: 30
<212> TYPE: DNA
<213> ORGANISM: Artificial sequence
<220> FEATURE:
<223> OTHER INFORMATION: Synthetic -continued

<400> SEQUENCE: 30
ggaagtcgac tgaagacagt caacgttgcg                                        30

<210> SEQ ID NO 31
<211> LENGTH: 28
<212> TYPE: DNA
<213> ORGANISM: Artificial sequence
<220> FEATURE:
<223> OTHER INFORMATION: Synthetic

<400> SEQUENCE: 31
ggaagctagc atggaggacg agatgccc                                          28

<210> SEQ ID NO 32
<211> LENGTH: 33
<212> TYPE: DNA
<213> ORGANISM: Artificial sequence
<220> FEATURE:
<223> OTHER INFORMATION: Synthetic

<400> SEQUENCE: 32
ggaagtcgac tgctgggttt cataccctgc cac                                    33

<210> SEQ ID NO 33
<211> LENGTH: 29
<212> TYPE: DNA
<213> ORGANISM: Artificial sequence
<220> FEATURE:
<223> OTHER INFORMATION: Synthetic

<400> SEQUENCE: 33
ggaagctagc atgcctcctc agcttcaag                                         29

<210> SEQ ID NO 34
<211> LENGTH: 30
<212> TYPE: DNA
<213> ORGANISM: Artificial sequence
<220> FEATURE:
<223> OTHER INFORMATION: Synthetic

<400> SEQUENCE: 34
ggaagtcgac tgcaagggaa ccacctgaag                                        30

<210> SEQ ID NO 35
<211> LENGTH: 31
<212> TYPE: DNA
<213> ORGANISM: Artificial sequence
<220> FEATURE:
<223> OTHER INFORMATION: Synthetic

<400> SEQUENCE: 35
ggaagctagc atggccgggg ggccgggccc g                                      31

<210> SEQ ID NO 36
<211> LENGTH: 33
<212> TYPE: DNA
<213> ORGANISM: Artificial sequence
<220> FEATURE:
<223> OTHER INFORMATION: Synthetic

<400> SEQUENCE: 36
ggaagtcgac tggctctgaa attcatcact ttc                                    33

<210> SEQ ID NO 37

```
<211> LENGTH: 30
<212> TYPE: DNA
<213> ORGANISM: Artificial sequence
<220> FEATURE:
<223> OTHER INFORMATION: Synthetic

<400> SEQUENCE: 37
ggaactcgag atggaggcgc tgagtcgagc                                      30

<210> SEQ ID NO 38
<211> LENGTH: 34
<212> TYPE: DNA
<213> ORGANISM: Artificial sequence
<220> FEATURE:
<223> OTHER INFORMATION: Synthetic

<400> SEQUENCE: 38
ggaagtcgac tgtaggttgt ggttgtcttt gttc                                 34

<210> SEQ ID NO 39
<211> LENGTH: 63
<212> TYPE: DNA
<213> ORGANISM: Artificial sequence
<220> FEATURE:
<223> OTHER INFORMATION: Synthetic

<400> SEQUENCE: 39
ggaagctagc gccaccatgg attacaagga tgacgatgac aagatggagg cgctgagtcg     60
agc                                                                   63

<210> SEQ ID NO 40
<211> LENGTH: 28
<212> TYPE: DNA
<213> ORGANISM: Artificial sequence
<220> FEATURE:
<223> OTHER INFORMATION: Synthetic

<400> SEQUENCE: 40
ggaagaattc tcataggttg tggttgtc                                        28

<210> SEQ ID NO 41
<211> LENGTH: 63
<212> TYPE: DNA
<213> ORGANISM: Artificial sequence
<220> FEATURE:
<223> OTHER INFORMATION: Synthetic

<400> SEQUENCE: 41
ggaagctagc gccaccatgg attacaagga tgacgatgac aagatggagg cgctgagtcg     60
agc                                                                   63

<210> SEQ ID NO 42
<211> LENGTH: 28
<212> TYPE: DNA
<213> ORGANISM: Artificial sequence
<220> FEATURE:
<223> OTHER INFORMATION: Synthetic

<400> SEQUENCE: 42
ggaagaattc tcataggttg tggttgtc                                        28

<210> SEQ ID NO 43
<211> LENGTH: 64
<212> TYPE: DNA
<213> ORGANISM: Artificial sequence
```

<220> FEATURE:
<223> OTHER INFORMATION: Synthetic

<400> SEQUENCE: 43
ggaagctagc gccaccatgg attacaagga tgacgatgac aagatggaga ccaaacgggt    60
ggag                                                                64

<210> SEQ ID NO 44
<211> LENGTH: 29
<212> TYPE: DNA
<213> ORGANISM: Artificial sequence
<220> FEATURE:
<223> OTHER INFORMATION: Synthetic

<400> SEQUENCE: 44
ggaaggatcc tcaaaggtcc aagattttc                                     29

<210> SEQ ID NO 45
<211> LENGTH: 64
<212> TYPE: DNA
<213> ORGANISM: Artificial sequence
<220> FEATURE:
<223> OTHER INFORMATION: Synthetic

<400> SEQUENCE: 45
ggaagctagc gccaccatgg attacaagga tgacgatgac aagatggccg gggggccggg    60
cccg                                                                64

<210> SEQ ID NO 46
<211> LENGTH: 31
<212> TYPE: DNA
<213> ORGANISM: Artificial sequence
<220> FEATURE:
<223> OTHER INFORMATION: Synthetic

<400> SEQUENCE: 46
ggaagaattc tcagctctga aattcatcac t                                  31

<210> SEQ ID NO 47
<211> LENGTH: 29
<212> TYPE: DNA
<213> ORGANISM: Artificial sequence
<220> FEATURE:
<223> OTHER INFORMATION: Synthetic

<400> SEQUENCE: 47
ggaagctagc atgcctcctc agcttcaag                                     29

<210> SEQ ID NO 48
<211> LENGTH: 31
<212> TYPE: DNA
<213> ORGANISM: Artificial sequence
<220> FEATURE:
<223> OTHER INFORMATION: Synthetic

<400> SEQUENCE: 48
ggaagaattc tcacaaggga accacctgaa g                                  31

<210> SEQ ID NO 49
<211> LENGTH: 220
<212> TYPE: RNA
<213> ORGANISM: Artificial sequence
<220> FEATURE:
<223> OTHER INFORMATION: Synthetic

```
<400> SEQUENCE: 49
cuguguuugu augucuugaa aagaauguca guuauuuauu gaaagucguc uuucauauug      60
uauggucaac acgcacgugu ugacgcuucc cuuggacauu uugugucuag uugguagggc     120
auaaugcccu uuuacauucu uuaacccugu uucuccuggu cucgucucgc ucgggacaga    180
gacguucaaa ggacuguuac aaaugaagua aaaauaaaag                            220

<210> SEQ ID NO 50
<211> LENGTH: 234
<212> TYPE: RNA
<213> ORGANISM: Artificial sequence
<220> FEATURE:
<223> OTHER INFORMATION: Synthetic

<400> SEQUENCE: 50
guauggucaa cacgcacgug uugacgcuuc ccuuggacau uuugugucua guugguaggg      60
cauaaugccc uuuuacauuc uuuaacccug uuucuccugg ucucgucucg cucgggacag    120
agguaugguc aacacgcacg uguugacgcu ucccuuggac auuuugoguc uaguggaug     180 ggcauaaugc ccuuuuacau ucuuuaaccc uguuucuccu ggucucgucu cgcu            234

<210> SEQ ID NO 51
<211> LENGTH: 112
<212> TYPE: RNA
<213> ORGANISM: Artificial sequence
<220> FEATURE:
<223> OTHER INFORMATION: Synthetic

<400> SEQUENCE: 51
guauggucaa cacgcacgug uugacgcuuc ccuuggacau uuugugucua guugguaggg      60
cauaaugccc uuuuacauuc uuuaacccug uuucuccugg ucucgucucg cu              112

<210> SEQ ID NO 52
<211> LENGTH: 82
<212> TYPE: RNA
<213> ORGANISM: Artificial sequence
<220> FEATURE:
<223> OTHER INFORMATION: Synthetic

<400> SEQUENCE: 52
uugacgcuuc ccuuggacau uuugugucua guugguaggg cauaaugccc uuuuacauuc      60
uuuaacccug uuucuccugg uc                                                82

<210> SEQ ID NO 53
<211> LENGTH: 82
<212> TYPE: RNA
<213> ORGANISM: Artificial sequence
<220> FEATURE:
<223> OTHER INFORMATION: Synthetic

<400> SEQUENCE: 53
uugacgcuuc ccuuggacau uuugugucua guugguaggg cauaaugccc uuuuacauuc      60
uuuaacccug uuucuccugg uc                                                82

<210> SEQ ID NO 54
<211> LENGTH: 47
<212> TYPE: RNA
<213> ORGANISM: Artificial sequence
<220> FEATURE:
<223> OTHER INFORMATION: Synthetic

<400> SEQUENCE: 54
```
ccuuggacau uuugugucua guugguaggg cauaaugccc uuuuaca          47

<210> SEQ ID NO 55
<211> LENGTH: 47
<212> TYPE: RNA
<213> ORGANISM: Artificial sequence
<220> FEATURE:
<223> OTHER INFORMATION: Synthetic

<400> SEQUENCE: 55
ccuuggacau uuugugucua guugguaggg cauaaugccc uuuuaca          47

<210> SEQ ID NO 56
<211> LENGTH: 47
<212> TYPE: RNA
<213> ORGANISM: Artificial sequence
<220> FEATURE:
<223> OTHER INFORMATION: Synthetic

<400> SEQUENCE: 56
ccuuggacau uuugugucua guugguaaaa cauaaugccc uuuuaca          47

<210> SEQ ID NO 57
<211> LENGTH: 47
<212> TYPE: RNA
<213> ORGANISM: Artificial sequence
<220> FEATURE:
<223> OTHER INFORMATION: Synthetic

<400> SEQUENCE: 57
ccuuggacau uuugugucua guugguaggg caaguugccc uuuuaca          47

<210> SEQ ID NO 58
<211> LENGTH: 47
<212> TYPE: RNA
<213> ORGANISM: Artificial sequence
<220> FEATURE:
<223> OTHER INFORMATION: Synthetic

<400> SEQUENCE: 58
ccuuggacau uuugugucua guugguaccc cauaaugggg uuuuaca          47

<210> SEQ ID NO 59
<211> LENGTH: 36
<212> TYPE: RNA
<213> ORGANISM: Artificial sequence
<220> FEATURE:
<223> OTHER INFORMATION: Synthetic

<400> SEQUENCE: 59
uugacgcuuc ccuuggacau uuugugucua guuggu          36

<210> SEQ ID NO 60
<211> LENGTH: 26
<212> TYPE: RNA
<213> ORGANISM: Artificial sequence
<220> FEATURE:
<223> OTHER INFORMATION: Synthetic

<400> SEQUENCE: 60
guugguaggg cauaaugccc uuuuac          26

<210> SEQ ID NO 61
<211> LENGTH: 220
<212> TYPE: RNA

<213> ORGANISM: Artificial sequence
<220> FEATURE:
<223> OTHER INFORMATION: Synthetic

<400> SEQUENCE: 61
cuguguuugu augucuugaa agaauguca guuauuuauu gaaagucguc uuucauauug          60
uauggucaac acgcacgugu ugacgcuucc cuuggacauu uugugucuag uugguagggc        120
auaaugcccu uuuacauucu uuaacccugu uucuccuggu cucgucucgc ucgggacaga       180
gacguucaaa ggacuguuac aaaugaagua aaauaaaag                              220

<210> SEQ ID NO 62
<211> LENGTH: 21
<212> TYPE: DNA
<213> ORGANISM: Artificial sequence
<220> FEATURE:
<223> OTHER INFORMATION: Synthetic

<400> SEQUENCE: 62
ctggccacag gggcgcctat c                                                  21

<210> SEQ ID NO 63
<211> LENGTH: 20
<212> TYPE: DNA
<213> ORGANISM: Artificial sequence
<220> FEATURE:
<223> OTHER INFORMATION: Synthetic

<400> SEQUENCE: 63
ggacaccttt tagcatcttt                                                    20

<210> SEQ ID NO 64
<211> LENGTH: 21
<212> TYPE: DNA
<213> ORGANISM: Artificial sequence
<220> FEATURE:
<223> OTHER INFORMATION: Synthetic

<400> SEQUENCE: 64
ggccttggaa gcatgtagag g                                                  21

<210> SEQ ID NO 65
<211> LENGTH: 23
<212> TYPE: DNA
<213> ORGANISM: Artificial sequence
<220> FEATURE:
<223> OTHER INFORMATION: Synthetic

<400> SEQUENCE: 65
ggagaactcg ttagagacga ctt                                                23

<210> SEQ ID NO 66
<211> LENGTH: 25
<212> TYPE: DNA
<213> ORGANISM: Artificial sequence
<220> FEATURE:
<223> OTHER INFORMATION: Synthetic

<400> SEQUENCE: 66
catcttctca aaattcgagt gacaa                                              25

<210> SEQ ID NO 67
<211> LENGTH: 23
<212> TYPE: DNA
<213> ORGANISM: Artificial sequence

```
<220> FEATURE:
<223> OTHER INFORMATION: Synthetic

<400> SEQUENCE: 67
tgggagtaga caaggtacaa ccc                                              23

<210> SEQ ID NO 68
<211> LENGTH: 19
<212> TYPE: DNA
<213> ORGANISM: Artificial sequence
<220> FEATURE:
<223> OTHER INFORMATION: Synthetic

<400> SEQUENCE: 68
gccttccgtg ttcctaccc                                                   19

<210> SEQ ID NO 69
<211> LENGTH: 19
<212> TYPE: DNA
<213> ORGANISM: Artificial sequence
<220> FEATURE:
<223> OTHER INFORMATION: Synthetic

<400> SEQUENCE: 69
tgcctgcttc accaccttc                                                   19

<210> SEQ ID NO 70
<211> LENGTH: 20
<212> TYPE: DNA
<213> ORGANISM: Artificial sequence
<220> FEATURE:
<223> OTHER INFORMATION: Synthetic

<400> SEQUENCE: 70
ggtcatcact attggcaacg                                                  20

<210> SEQ ID NO 71
<211> LENGTH: 20
<212> TYPE: DNA
<213> ORGANISM: Artificial sequence
<220> FEATURE:
<223> OTHER INFORMATION: Synthetic

<400> SEQUENCE: 71
acggatgtca acgtcacact                                                  20

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
aaccgaagtc atagccacac                                                  20

<210> SEQ ID NO 73
<211> LENGTH: 22
<212> TYPE: DNA
<213> ORGANISM: Artificial sequence
<220> FEATURE:
<223> OTHER INFORMATION: Synthetic

<400> SEQUENCE: 73
gttggatttg tcactgttca gc                                               22
```

<210> SEQ ID NO 74
<211> LENGTH: 23
<212> TYPE: DNA
<213> ORGANISM: Artificial sequence
<220> FEATURE:
<223> OTHER INFORMATION: Synthetic

<400> SEQUENCE: 74
cactgctgct gagatgaatg aaa                                               23

<210> SEQ ID NO 75
<211> LENGTH: 20
<212> TYPE: DNA
<213> ORGANISM: Artificial sequence
<220> FEATURE:
<223> OTHER INFORMATION: Synthetic

<400> SEQUENCE: 75
gtctgtaggc aggtcggctc                                                   20

<210> SEQ ID NO 76
<211> LENGTH: 18
<212> TYPE: DNA
<213> ORGANISM: Artificial sequence
<220> FEATURE:
<223> OTHER INFORMATION: Synthetic

<400> SEQUENCE: 76
tcagcaagga cagcagag                                                     18

<210> SEQ ID NO 77
<211> LENGTH: 21
<212> TYPE: DNA
<213> ORGANISM: Artificial sequence
<220> FEATURE:
<223> OTHER INFORMATION: Synthetic

<400> SEQUENCE: 77
gtatgtgaga ggaagagaac c                                                 21

<210> SEQ ID NO 78
<211> LENGTH: 19
<212> TYPE: DNA
<213> ORGANISM: Artificial sequence
<220> FEATURE:
<223> OTHER INFORMATION: Synthetic

<400> SEQUENCE: 78
gtcggtatgg gtcagaaag                                                    19

<210> SEQ ID NO 79
<211> LENGTH: 19
<212> TYPE: DNA
<213> ORGANISM: Artificial sequence
<220> FEATURE:
<223> OTHER INFORMATION: Synthetic

<400> SEQUENCE: 79
ctcgttgtag aaggtgtgg                                                    19

<210> SEQ ID NO 80
<211> LENGTH: 46
<212> TYPE: RNA
<213> ORGANISM: Mus musculus

<400> SEQUENCE: 80

```
ccuuggacau uuugugucua guugguaggg cauaaugccc uuuuac        46
```

<210> SEQ ID NO 81
<211> LENGTH: 72
<212> TYPE: DNA
<213> ORGANISM: Mus musculus

<400> SEQUENCE: 81

```
ttgacgcttc ccttggacat tttgtgtcta gttggtaggg cataatgccc ttttacattc    60
tttaaccctg tt                                                       72
```

<210> SEQ ID NO 82
<211> LENGTH: 69
<212> TYPE: DNA
<213> ORGANISM: Rat norvegicus

<400> SEQUENCE: 82

```
ttgaagcttc ccttggacat tttatgtcta gtttgtaggg cacaatgcct tttatattct    60
ttaaccaat                                                           69
```

<210> SEQ ID NO 83
<211> LENGTH: 75
<212> TYPE: DNA
<213> ORGANISM: Homo sapiens

<400> SEQUENCE: 83

```
tctaaatatc ccttggacat tttatgtctt tcttgtaagg catactgcct tgtttaatgg    60
tagttttaca gtgtt                                                    75
```

<210> SEQ ID NO 84
<211> LENGTH: 75
<212> TYPE: DNA
<213> ORGANISM: Pan troglodytes

<400> SEQUENCE: 84

```
tctaaatatc ccttggacat cttatgtctt tcttgtaagg catactgcct tgtttaatgg    60
tagttttaca gtgtt                                                    75
```

<210> SEQ ID NO 85
<211> LENGTH: 73
<212> TYPE: DNA
<213> ORGANISM: Mesocricetus auratus

<400> SEQUENCE: 85

```
ttgaagtttc ccttggacat tttatgtcta ctttgtaggg catagtgccc tgttatattc    60
tttaaccaat gtt                                                      73
```

<210> SEQ ID NO 86
<211> LENGTH: 75
<212> TYPE: DNA
<213> ORGANISM: Equus ferus caballus

<400> SEQUENCE: 86

```
tctaaatatc ccttggacat tttatgtctt ccttgtaagg cataatgcct tgtttagcgt    60
taattatgca gtatt                                                    75
```

<210> SEQ ID NO 87
<211> LENGTH: 75
<212> TYPE: DNA

<213> ORGANISM: Cavia porcellus

<400> SEQUENCE: 87

```
tctaattatc ccttggacat tttatgtctt ctttgtaagg cacaatgcct tgtttagcca    60
taactgtgac ctgtt                                                    75
```

<210> SEQ ID NO 88
<211> LENGTH: 24
<212> TYPE: RNA
<213> ORGANISM: Artificial sequence
<220> FEATURE:
<223> OTHER INFORMATION: Synthetic

<400> SEQUENCE: 88

```
guugguaggg cauaaugccc uuuu                                          24
```

<210> SEQ ID NO 89
<211> LENGTH: 47
<212> TYPE: RNA
<213> ORGANISM: Artificial sequence
<220> FEATURE:
<223> OTHER INFORMATION: Synthetic

<400> SEQUENCE: 89

```
ccuuggacau uugugucua guugguaggg cauaaugccc uuuuaca                  47
```

<210> SEQ ID NO 90
<211> LENGTH: 44
<212> TYPE: RNA
<213> ORGANISM: Artificial sequence
<220> FEATURE:
<223> OTHER INFORMATION: Synthetic

<400> SEQUENCE: 90

```
uugugucua guggguaccc cauaaugggg uuuuacauuc uuua                     44
```

<210> SEQ ID NO 91
<211> LENGTH: 37
<212> TYPE: RNA
<213> ORGANISM: Artificial sequence
<220> FEATURE:
<223> OTHER INFORMATION: Synthetic

<400> SEQUENCE: 91

```
uuuucucucu aguggguaag gcauaaugcc auuuuac                            37
```

<210> SEQ ID NO 92
<211> LENGTH: 37
<212> TYPE: RNA
<213> ORGANISM: Artificial sequence
<220> FEATURE:
<223> OTHER INFORMATION: Synthetic

<400> SEQUENCE: 92

```
uugccuccuc uuuuuaugc uuaaagcaaa auauuua                             37
```

<210> SEQ ID NO 93
<211> LENGTH: 48
<212> TYPE: RNA
<213> ORGANISM: Artificial sequence
<220> FEATURE:
<223> OTHER INFORMATION: Synthetic

<400> SEQUENCE: 93

```
uuuauugaua auuuauauaa auaaccuuaa agguaaaaua ugauugau                48
```

```
<210> SEQ ID NO 94
<211> LENGTH: 47
<212> TYPE: RNA
<213> ORGANISM: Artificial sequence
<220> FEATURE:
<223> OTHER INFORMATION: Synthetic

<400> SEQUENCE: 94
ccuuggacau uuuguauaua guugguaggg cauaaugccc uuuuaca                     47

<210> SEQ ID NO 95
<211> LENGTH: 147
<212> TYPE: PRT
<213> ORGANISM: Homo sapiens

<400> SEQUENCE: 95
```

Arg Lys Val Phe Ile Thr Tyr Ser Met Asp Thr Ala Met Glu Val Val
1               5                   10                  15

Lys Phe Val Asn Phe Leu Leu Val Asn Gly Phe Gln Thr Ala Ile Asp
            20                  25                  30

Ile Phe Glu Asp Arg Ile Arg Gly Ile Asp Ile Lys Trp Met Glu
        35                  40                  45

Arg Tyr Leu Arg Asp Lys Thr Val Met Ile Ile Val Ala Ile Ser Pro
    50                  55                  60

Lys Tyr Lys Gln Asp Val Glu Gly Ala Glu Ser Gln Leu Asp Glu Asp
65                  70                  75                  80

Glu His Gly Leu His Thr Lys Tyr Ile His Arg Met Met Gln Ile Glu
                85                  90                  95

Phe Ile Ser Gln Gly Ser Met Asn Phe Arg Phe Ile Pro Val Leu Phe
            100                 105                 110

Pro Asn Ala Lys Lys Glu His Val Pro Thr Trp Leu Gln Asn Thr His
        115                 120                 125

Val Tyr Ser Trp Pro Lys Asn Lys Lys Asn Ile Leu Leu Arg Leu Leu
    130                 135                 140

Arg Glu Glu
145

```
<210> SEQ ID NO 96
<211> LENGTH: 25
<212> TYPE: DNA
<213> ORGANISM: Homo sapiens

<400> SEQUENCE: 96
cttttgctta tgtttaaaac aaaat                                             25

<210> SEQ ID NO 97
<211> LENGTH: 23
<212> TYPE: DNA
<213> ORGANISM: Homo sapiens

<400> SEQUENCE: 97
agtaaacttt aagttaattt aug                                               23

<210> SEQ ID NO 98
<211> LENGTH: 23
<212> TYPE: DNA
<213> ORGANISM: Homo sapiens

<400> SEQUENCE: 98
```

```
ctgaccctga tacaggcatg gca                                           23
```

<210> SEQ ID NO 99
<211> LENGTH: 40
<212> TYPE: RNA
<213> ORGANISM: Artificial sequence
<220> FEATURE:
<223> OTHER INFORMATION: Synthetic

<400> SEQUENCE: 99

```
gauaauuuaa auaaguaaac uuuaaguuaa uuuaugauug                         40
```

<210> SEQ ID NO 100
<211> LENGTH: 35
<212> TYPE: RNA
<213> ORGANISM: Artificial sequence
<220> FEATURE:
<223> OTHER INFORMATION: Synthetic

<400> SEQUENCE: 100

```
aucgccgcuu uugauaauca acugggcuga acacu                              35
```

<210> SEQ ID NO 101
<211> LENGTH: 50
<212> TYPE: RNA
<213> ORGANISM: Artificial sequence
<220> FEATURE:
<223> OTHER INFORMATION: Synthetic

<400> SEQUENCE: 101

```
gacccugaua caggcauggc agaagaaugg gaauauuuua uacugacaga              50
```

<210> SEQ ID NO 102
<211> LENGTH: 47
<212> TYPE: RNA
<213> ORGANISM: Artificial sequence
<220> FEATURE:
<223> OTHER INFORMATION: Synthetic

<400> SEQUENCE: 102

```
ucucuaccuu guugccuccu cuuuugcuua uguuuaaaac aaaauau                 47
```

<210> SEQ ID NO 103
<211> LENGTH: 11
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(7)
<223> OTHER INFORMATION: N = A or U

<400> SEQUENCE: 103

```
aagannnucu u                                                        11
```

<210> SEQ ID NO 104
<211> LENGTH: 152
<212> TYPE: RNA
<213> ORGANISM: Artificial sequence
<220> FEATURE:
<223> OTHER INFORMATION: Synthetic

<400> SEQUENCE: 104

```
ggaagagaac accucuuuau ggcuuacccu cuagaauuuc uaauuuaugu guucuguuga   60
aauuuuuguu uuuuuaccuu uauugaaaca acaaaaaguc aguauugaaa cauaucuucc  120
```

```
uguuuucugu ugucaaauga ugauaaugug cc                                   152

<210> SEQ ID NO 105
<211> LENGTH: 316
<212> TYPE: RNA
<213> ORGANISM: Artificial sequence
<220> FEATURE:
<223> OTHER INFORMATION: Synthetic

<400> SEQUENCE: 105
gagcuguacc cagagagucc ugugcugaau guggacucaa ucccuagggc uggcagaaag     60
ggaacagaaa gguuuuugag uacggcuaua gccuggacuu uccuguuguc uacaccaaug   120
cccaacugcc ugccuuaggg uagugcuaag aggaucuccu guccaucagc caggacaguc   180
agcucucucc uuucagggcc aaucccccagc ccuuuuguug agccaggccu cucucaccuc   240
uccuacucac uuaaagcccg ccugacagaa accacggcca cauuugguuc uaagaaaccc   300
ucugucauuc gcuccc                                                     316

<210> SEQ ID NO 106
<211> LENGTH: 257
<212> TYPE: RNA
<213> ORGANISM: Artificial sequence
<220> FEATURE:
<223> OTHER INFORMATION: Synthetic

<400> SEQUENCE: 106
cccucuguca uucgcuccca cauucugaug agcaaccgcu ucccuauuua uuuauuuauu     60
uguuuguuug uuuuauucau uggucuaauu uauucaaagg gggcaagaag uagcagguguc   120 uguaaaagag ccaguuuuu aauagcuaug gaaucaauuc aauuuggacu ggugugcucu   180
cuuuaaauca aguccuuuaa uuaagacuga aauauauaa gcucagauua uuuaaauggg   240
aauauuuaua aaugagc                                                    257

<210> SEQ ID NO 107
<211> LENGTH: 105
<212> TYPE: RNA
<213> ORGANISM: Artificial sequence
<220> FEATURE:
<223> OTHER INFORMATION: Synthetic

<400> SEQUENCE: 107
cauguauuug uuugcauagg ugaucucauu uaaccucuc aaccaccuuu cagauaacug     60
uuauuuauaa ucacuuuuuu ccacauaagg aaacuggguu ccugc                     105

<210> SEQ ID NO 108
<211> LENGTH: 222
<212> TYPE: RNA
<213> ORGANISM: Artificial sequence
<220> FEATURE:
<223> OTHER INFORMATION: Synthetic

<400> SEQUENCE: 108
cacagaggca aaggagaaa aucauguuga aacaaaccga aaauggacau ugagauacua     60
ucauuaacau uaggaccuua gaauuuggg uauuguaauc ugaaguaugg uauuacaaaa   120
caaacaaaca aacaaaaaac ccauguguua aaauacucag ugcuaaacau ggcuuaaucu   180
uauuuuaucu ucuuuccuca auauaggagg gaagauuuuu cc                        222

<210> SEQ ID NO 109
```

```
<211> LENGTH: 143
<212> TYPE: RNA
<213> ORGANISM: Artificial sequence
<220> FEATURE:
<223> OTHER INFORMATION: Synthetic

<400> SEQUENCE: 109
ggaacuuaaa uaaugugaaa cuggauuaaa cuuaaucuaa auggaaccac ucuaucaagu      60
auuauaccuu uuuuagaguu gauacuacag uuuguuagua ugaggcauuu guuugaacug     120
auaaagauga gugagcaugc ccc                                            143

<210> SEQ ID NO 110
<211> LENGTH: 267
<212> TYPE: RNA
<213> ORGANISM: Artificial sequence
<220> FEATURE:
<223> OTHER INFORMATION: Synthetic

<400> SEQUENCE: 110
caccugcagu guguauugag ucugcuggac uccaggaccu agacagagcu cucuaaaucu      60
gauccaggga ucuuagcuaa cggaaacaac uccuuggaaa accucguuug uaccucucuc     120
cgaaauauuu auuaccucug uaccucagu ucccauucua uuuauucacu gagcuucucu     180
gugaacuauu uagaaagaag cccaauauua uaauuuuaca guauuauua uuuuuaaccu     240 guguuuaagc uguuuccauu ggggaca                                        267

<210> SEQ ID NO 111
<211> LENGTH: 231
<212> TYPE: RNA
<213> ORGANISM: Artificial sequence
<220> FEATURE:
<223> OTHER INFORMATION: Synthetic

<400> SEQUENCE: 111
cucuuugacc aauuaauuau ucuuucugac uaauuagcca agacugugau ugcggggpuug     60 uaucggggg uggggggacag ccaagcggcu gacugaacuc agauuguagc uuguaccuuu    120
acuucacuga ccaauaagaa acauucagag cugcagugac cccgggaggu gcugcugaug    180
ggaggagaug ucuacacucc gggccagcgc uuuaacagca ggccagacag c             231

<210> SEQ ID NO 112
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 112
nnnnnnnnnn nnagauaaua ucunnnnnnn nnnnn                                36

<210> SEQ ID NO 113
<211> LENGTH: 36
<212> TYPE: RNA
<213> ORGANISM: Artificial sequence
<220> FEATURE:
<223> OTHER INFORMATION: Synthetic
```

```
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 113
nnnnnnnnnn nncgauaaua ucgnnnnnnn nnnnnn                              36

<210> SEQ ID NO 114
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 114
nnnnnnnnnn nnagcuaaug ucunnnnnnn nnnnnn                              36

<210> SEQ ID NO 115
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 115
nnnnnnnnnn nncgcuaaua gcgnnnnnnn nnnnnn                              36

<210> SEQ ID NO 116
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 116
nnnnnnnnnn nnugauaaua ucannnnnnn nnnnnn                              36

<210> SEQ ID NO 117
<211> LENGTH: 36
<212> TYPE: RNA
<213> ORGANISM: Artificial sequence
<220> FEATURE:
```

<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 117
nnnnnnnnnn nnuguuaaua acannnnnnn nnnnnn                        36

<210> SEQ ID NO 118
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 118
nnnnnnnnnn nngauaaua uccnnnnnnn nnnnnn                         36

<210> SEQ ID NO 119
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 119
nnnnnnnnnn nnagguaaua ccunnnnnnn nnnnnn                        36

<210> SEQ ID NO 120
<211> LENGTH: 36
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 120
nnnnnnnnnn nnggguaaua cccnnnnnnn nnnnnn                        36

<210> SEQ ID NO 121
<211> LENGTH: 36
<212> TYPE: RNA
<213> ORGANISM: Artificial sequence

```
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, c, g, or u
<220> FEATURE:
<221> NAME/KEY: misc_feature
<222> LOCATION: (24)..(36)
<223> OTHER INFORMATION: n is a, c, g, or u

<400> SEQUENCE: 121
nnnnnnnnnn nnaguuaaua acunnnnnnn nnnnnn                                    36

<210> SEQ ID NO 122
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 122
nnnnnnnnnn naagaaaauc uunnnnnnnn n                                         31

<210> SEQ ID NO 123
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 123
nnnnnnnnnn naagaauauc uunnnnnnnn n                                         31

<210> SEQ ID NO 124
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 124
nnnnnnnnnn naagaaauuc uunnnnnnnn n                                         31

<210> SEQ ID NO 125
<211> LENGTH: 31
<212> TYPE: RNA
```

```
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 125
nnnnnnnnnn naagaauuuc uunnnnnnnn n          31

<210> SEQ ID NO 126
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 126
nnnnnnnnnn naagauaauc uunnnnnnnn n          31

<210> SEQ ID NO 127
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 127
nnnnnnnnnn naagauauuc uunnnnnnnn n          31

<210> SEQ ID NO 128
<211> LENGTH: 31
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 128
nnnnnnnnnn naagauuauc uunnnnnnnn n          31

<210> SEQ ID NO 129
<211> LENGTH: 31
```

```
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (23)..(31)
<223> OTHER INFORMATION: n is a, c, g, or u

<400> SEQUENCE: 129
nnnnnnnnnn naagauuuuc uunnnnnnnn n                          31
```